US012790628B2

(12) United States Patent
Ghislieri et al.

(10) Patent No.: US 12,790,628 B2
(45) **Date of Patent: *Nov. 10, 2026**

(54) METHOD FOR PRODUCTION OF 4-CYANO BENZOIC ACID OR SALTS THEREOF

(71) Applicant: BASF SE, Ludwigshafen am Rhein (DE)

(72) Inventors: Diego Ghislieri, Ludwigshafen (DE); Christian Willrodt, Ludwigshafen (DE); Christopher Koradin, Ludwigshafen (DE); Stefan Seemayer, Ludwigshafen (DE); Doreen Schachtschabel, Ludwigshafen (DE); Kai-Uwe Baldenius, Mannheim (DE); Roland Goetz, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 603 days.

This patent is subject to a terminal disclaimer.

(21) Appl. No.: 17/424,824

(22) PCT Filed: Jan. 20, 2020

(86) PCT No.: PCT/EP2020/051288

§ 371 (c)(1),
(2) Date: Jul. 21, 2021

(87) PCT Pub. No.: WO2020/152104

PCT Pub. Date: Jul. 30, 2020

(65) Prior Publication Data

US 2022/0017931 A1 Jan. 20, 2022

(30) Foreign Application Priority Data

Jan. 22, 2019 (EP) .................................... 19153038
Nov. 18, 2019 (EP) .................................... 19209627
Jan. 17, 2020 (EP) .................................... 20152502

(51) Int. Cl.
*C12P 7/40* (2006.01)
*C12N 9/78* (2006.01)
*C12P 13/00* (2006.01)

(52) U.S. Cl.
CPC .............. *C12P 13/002* (2013.01); *C12N 9/78* (2013.01); *C12Y 305/05001* (2013.01)

(58) Field of Classification Search
None
See application file for complete search history.

(56) References Cited

U.S. PATENT DOCUMENTS 5,565,350 A 10/1996 Kmiec
6,433,211 B1 8/2002 Hiroshi et al.
12,486,221 B2 * 12/2025 Vogt ...................... C07C 259/18

FOREIGN PATENT DOCUMENTS

CN 107641622 A 1/2018
DE 69314280 T2 2/1998
WO 0015815 A1 3/2000
WO 2003000840 A2 1/2003
WO 2009059096 A1 5/2009

OTHER PUBLICATIONS

Vergne-Vaxelaire et al., Adv. Synth. Catal. 355:1763-1779, 2013 (Year: 2013).*
Singh et al., Curr. Protein Pept. Sci. 18:1-11, 2017 (Year: 2017).*
Zhang et al., Structure 26:1474-1485, 2018 (Year: 2018).*
Zhang et al., Process Biochemistry 75:152-156, 2018 (Year: 2018).*
Chen et al., J. Microbiol. Biotechnol. 25:1660-1669, 2015 (Year: 2015).*
International Search Report and Written Opinion for corresponding PCT/EP2020/051288 mailed Jul. 20, 2020, 34 Pages.
Davis, E.W. et al., "Full Aliphatic nitrilase", Dec. 20, 2017 (Dec. 20, 2017), Retrieved from the Internet: URL:https://www.uniprot.org/uniprot/A0A1B9T6T9.txt?version=7 XP055694476 retrieved on May 12, 2020.
Hug, L.A et al., "Full=Nitrilase, EC=3.5.5.1", Dec. 5, 2018 (Dec. 5, 2018), Retrieved from the Internet: URL:https://www.uniprot.org/uniprot/A0A0T5ZRV8.txt?version=8 XP055694479 [retrieved on May 12, 2020].
Anonymous, "carbon-nitrogen hydrolase family protein [Tepidicaulis marinus]", Jun. 10, 2016 (Jun. 10, 2016), Retrieved from the Internet: URL:https://www.ncbi.nlm.nih.gov/protein/WP_052379230 XP055694526 [retrieved on May 12, 2020].
Copeland, A. et al., "Full=Nitrilase, EC=3.5.5.1", Jan. 16, 2019 (Jan. 16, 2019), Retrieved from the Internet: URL:https://www.uniprot.org/uniprot/A5VE02.txt?version=54 XP055694527 [retrieved on May 12, 2020].
Woodcraft, B.J., "Full=Aliphatic nitrilase", Dec. 20, 2017 (Dec. 20, 2017), Retrieved from the Internet: URL:https://www.uniprot.org/uniprot/A0A1E4YHA6.txt?version=7 XP055694528 [retrieved on May 12, 2020].
Zhou, G. et al., "Full=Aliphatic nitrilase", Jan. 16, 2019 (Jan. 16, 2019), Retrieved from the Internet: URL:https://www.uniprot.org/uniprot/A0A0C1IV51.txt?version=14 XP055694530 [retrieved on May 12, 2020].
Antunes, A. et al., "Full=Nitrilase protein, EC=3.5.5.7", Jan. 16, 2019 (Jan. 16, 2019), Retrieved from the Internet: URL:https://www.uniprot.org/uniprot/U2E2P4.txt?version=20 XP055694531 [retrieved on May 12, 2020].
"Use of nitrilase as biocatalyst for preparing p-cyanobenzoic acid for selectively hydrolyzing terephthalonitrile", Database WPI, Week 201815, Thomson Scientific, retrieved from STN Database accession No. 2018-10365V, XP002799015, Jan. 30, 2018, 2 pages.

(Continued)

*Primary Examiner* — David Steadman
(74) *Attorney, Agent, or Firm* — Armstrong Teasdale LLP

(57) ABSTRACT

Described herein are methods for the production of 4-cyano benzoic acid or salts thereof from terephthalonitrile using nitrilase as catalyst. Also described herein are compositions including 4-cyano benzoic acid.

25 Claims, 1 Drawing Sheet

Figure 1:
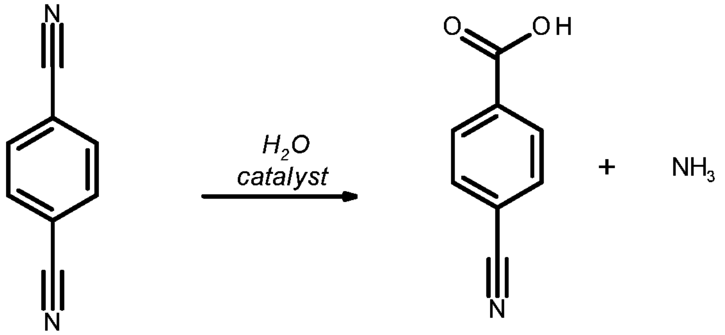

Specification includes a Sequence Listing.

(56) References Cited

OTHER PUBLICATIONS

Bengis-Garber, et al., "Bacteria in organic synthesis: Selective conversion of 1, 3-dicyanobenezene into 3-cyanobenzoic acid", Tetrahedron Letters, vol. 29, Issue 21, 1988, pp. 2589-2590.
Crosby, et al., "Regioselective hydrolysis of aromatic dinitriles using a whole cell catalyst", Journal of the Chemical Society, Perkin Transactions 1, Issue 13, 1994, pp. 1679-1687.
Gong, et al., "Nitrilases in nitrile biocatalysis: Recent progress and forthcoming research", Microbial Cell Factories, vol. 11, Issue 1, Article No. 142, Oct. 30, 2012, 18 pages.
J. Goa, "A Micro Biuret Method for Protein Determination Determination of Total Protein in Cerebrospinal Fluid", Scandinavian Journal of Clinical and Laboratory Investigation, vol. 5, Issue 3, 1953, pp. 218-222.
Kobayashi, et al., "Regiospecific hydrolysis of dinitrile compounds by nitrilase from Rhodococcus rhodochrous J1", Applied Microbiology and Biotechnology, vol. 29, Issue 2, Sep. 1988, pp. 231-233.
Lowry, et al., "Protein measurement with the Folin phenol reagent", Journal of Biological Chemistry, vol. 193, Issue 1, Nov. 1, 1951, pp. 265-275.
Bradford, et al., "A rapid and sensitive method for the quantitation of microgram quantities of protein utilizing the principle of protein-dye binding", Analytical Biochemistry, vol. 72, Issue 1-2, May 7, 1976, pp. 248-254.
Martínková, et al., "Biotransformations of Aromatic Dinitriles Using Rhodococcus-Equi Cells", Biotechnology Letters, vol. 17, Issue 11, Nov. 1995, pp. 1219-1222.
Meinkoth, et al., "Hybridization of nucleic acids immobilized on solid supports", Analytical Biochemistry, vol. 138, Issue 2, May 1, 1984, pp. 267-284.
Needleman, et al., "A general method applicable to the search for similarities in the amino acid sequence of two proteins", Journal of Molecular Biology, vol. 48, Issue 3, Mar. 28, 1970, pp. 443-453.
Šnajdrová, et al., "Nitrile biotransformation by Aspergillus niger", Journal of Molecular Catalysis B: Enzymatic, vol. 29, Issue 1-6, Jun. 21, 2004, pp. 227-232.
Stueckler, et al., "Nicotinamide-independent asymmetric bioreduction of Cdouble bondC-bonds via disproportionation of enones catalyzed by enoate reductases", Tetrahedron, vol. 66, Issue 3, Jan. 16, 2010, pp. 663-667.

* cited by examiner

SEQUENCE LISTING

```
<160> NUMBER OF SEQ ID NOS: 115

<210> SEQ ID NO 1
<211> LENGTH: 1062
<212> TYPE: DNA
<213> ORGANISM: Comamonas testosteroni

<400> SEQUENCE: 1

atgaaaaatt atcctacagt caaggtagca gcagtgcaag ctgctcctgt atttatgaat      60

ctagaggcaa cagtagataa aacttgtaag ttaatagcag aagcagcatc tatgggcgcc     120

aaggttatcg gcttcccaga agcatttatt cccggctatc catattggat ttggacatca     180

aatatggact tcactggaat gatgtgggcc gtccttttca agaatgcgat tgaaatccca     240

agcaaagaag ttcaacaaat tagtgatgct gcaaaaaaga atggagttta cgtttgcgtt     300

tctgtatcag agaaagataa tgcctcgcta tatttgacgc aattgtggtt tgacccgaat     360

ggtaatttga ttggcaagca caggaaattc aagcccacta gtagtgaaag agctgtatgg     420

ggagatgggg atggaagcat ggctcccgta tttaaaacag agtatgggaa tcttgggggga     480

ctccagtgct gggaacatgc tctcccatta aacattgcgg cgatgggctc attgaacgaa     540

caggtacatg ttgcttcctg gccagccttc gtccctaaag gcgcagtatc atccagagta     600

tcatccagcg tctgtgcgtc tactaatgcg atgcatcaga tcattagtca gttttacgcg     660

atcagcaatc aggtatatgt aattatgtca accaatctcg ttggccaaga catgattgac     720

atgattggga aagatgaatt ttccaaaaac tttctaccgc ttggttctgg aaacacagcg     780

attatttcta acaccggtga gattttggca tcaattccac aagacgcgga gggaattgct     840

gttgcagaga ttgaccttaa ccaaataatt tatggaaagt ggttactgga tcccgccggt     900

cattactcta ctcccggctt cttaagtttg acatttgatc agtctgaaca tgtacccgta     960

aaaaaaatag gtgagcagac aaaccatttc atctcttatg aagacttaca tgaagataaa    1020

atggatatgc taacgattcc gccgaggcgc gtagccacag cg                       1062


<210> SEQ ID NO 2
<211> LENGTH: 354
<212> TYPE: PRT
<213> ORGANISM: Comamonas testosteroni

<400> SEQUENCE: 2

Met Lys Asn Tyr Pro Thr Val Lys Val Ala Ala Val Gln Ala Ala Pro
1               5                   10                  15

Val Phe Met Asn Leu Glu Ala Thr Val Asp Lys Thr Cys Lys Leu Ile
```

```
            20                  25                  30

Ala Glu Ala Ala Ser Met Gly Ala Lys Val Ile Gly Phe Pro Glu Ala
        35                  40                  45

Phe Ile Pro Gly Tyr Pro Tyr Trp Ile Trp Thr Ser Asn Met Asp Phe
    50                  55                  60

Thr Gly Met Met Trp Ala Val Leu Phe Lys Asn Ala Ile Glu Ile Pro
65                  70                  75                  80

Ser Lys Glu Val Gln Gln Ile Ser Asp Ala Ala Lys Lys Asn Gly Val
                85                  90                  95

Tyr Val Cys Val Ser Val Ser Glu Lys Asp Asn Ala Ser Leu Tyr Leu
            100                 105                 110

Thr Gln Leu Trp Phe Asp Pro Asn Gly Asn Leu Ile Gly Lys His Arg
        115                 120                 125

Lys Phe Lys Pro Thr Ser Ser Glu Arg Ala Val Trp Gly Asp Gly Asp
    130                 135                 140

Gly Ser Met Ala Pro Val Phe Lys Thr Glu Tyr Gly Asn Leu Gly Gly
145                 150                 155                 160

Leu Gln Cys Trp Glu His Ala Leu Pro Leu Asn Ile Ala Ala Met Gly
                165                 170                 175

Ser Leu Asn Glu Gln Val His Val Ala Ser Trp Pro Ala Phe Val Pro
            180                 185                 190

Lys Gly Ala Val Ser Ser Arg Val Ser Ser Ser Val Cys Ala Ser Thr
        195                 200                 205

Asn Ala Met His Gln Ile Ile Ser Gln Phe Tyr Ala Ile Ser Asn Gln
    210                 215                 220

Val Tyr Val Ile Met Ser Thr Asn Leu Val Gly Gln Asp Met Ile Asp
225                 230                 235                 240

Met Ile Gly Lys Asp Glu Phe Ser Lys Asn Phe Leu Pro Leu Gly Ser
                245                 250                 255

Gly Asn Thr Ala Ile Ile Ser Asn Thr Gly Glu Ile Leu Ala Ser Ile
            260                 265                 270

Pro Gln Asp Ala Glu Gly Ile Ala Val Ala Glu Ile Asp Leu Asn Gln
        275                 280                 285

Ile Ile Tyr Gly Lys Trp Leu Leu Asp Pro Ala Gly His Tyr Ser Thr
    290                 295                 300

Pro Gly Phe Leu Ser Leu Thr Phe Asp Gln Ser Glu His Val Pro Val
305                 310                 315                 320

Lys Lys Ile Gly Glu Gln Thr Asn His Phe Ile Ser Tyr Glu Asp Leu
                325                 330                 335

His Glu Asp Lys Met Asp Met Leu Thr Ile Pro Pro Arg Arg Val Ala
            340                 345                 350

Thr Ala
```

<210> SEQ ID NO 3
<211> LENGTH: 990
<212> TYPE: DNA
<213> ORGANISM: Unknown
<220> FEATURE:
<223> OTHER INFORMATION: Unknown prokaryotic organism

<400> SEQUENCE: 3

```
atgaaggtgg ttaaagcagc agcagttcag attagcccgg ttctgtatag tcgcgaagcc      60

accgttgaaa aagttgttaa aaagattcac gagctgggcc agctgggtgt gcagtttgca     120

acctttccgg aaaccgttgt tccgtattat ccgtatttta gtgcagttca gaccggtatt     180
```

```
gaactgctga gtggcaccga acatctgcgc ctgctggatc aggccgtgac cgttccgagt    240

ccggcaaccg atgcaattgg tgaagccgcc cgcaaagccg gtatggttgt gagtattggt    300

gttaatgaac gtgatggtgg caccctgtat aatacccagc tgctgtttga tgcagatggt    360

accctgattc agcgtcgtcg taaaattacc ccgacccatt ttgaacgcat gatttggggt    420

cagggtgacg gtagcggtct gcgtgcagtt gatagtaaag ttggtcgcat tggtcagctg    480

gcatgttttg aacataataa tccgctggcc cgctatgcac tgattgcaga tggtgaacag    540

attcatagcg caatgtatcc gggcagtgcc tttggtgaag gttttgcaca gcgtatggaa    600

attaatattc gtcagcatgc actggaaagt ggcgcatttg tggtgaatgc aaccgcatgg    660

ctggatgcag atcagcaggc acagattatt aaggataccg gttgtggtat tggtccgatt    720

agcggcggtt gttttaccac cattgtggca ccggatggta tgctgatggc cgaaccgctg    780

cgtagtggcg aaggcgaagt gattgttgat ctggatttta ccctgattga tcgccgcaaa    840

atgctgatgg atagcgcagg ccattataat cgtccggaac tgctgagcct gatgattgat    900

cgcaccgcaa ccgcccatgt tcatgaacgc gccgcacatc cggtgagtgg tgccgaacag    960

ggcccggaag atttgcgcac cccggccgct                                     990


<210> SEQ ID NO 4
<211> LENGTH: 330
<212> TYPE: PRT
<213> ORGANISM: Unknown
<220> FEATURE:
<223> OTHER INFORMATION: Unknown prokaryotic organism

<400> SEQUENCE: 4

Met Lys Val Val Lys Ala Ala Ala Val Gln Ile Ser Pro Val Leu Tyr
1               5                   10                  15

Ser Arg Glu Ala Thr Val Glu Lys Val Val Lys Lys Ile His Glu Leu
            20                  25                  30

Gly Gln Leu Gly Val Gln Phe Ala Thr Phe Pro Glu Thr Val Val Pro
        35                  40                  45

Tyr Tyr Pro Tyr Phe Ser Ala Val Gln Thr Gly Ile Glu Leu Leu Ser
    50                  55                  60

Gly Thr Glu His Leu Arg Leu Leu Asp Gln Ala Val Thr Val Pro Ser
65                  70                  75                  80

Pro Ala Thr Asp Ala Ile Gly Glu Ala Ala Arg Lys Ala Gly Met Val
                85                  90                  95

Val Ser Ile Gly Val Asn Glu Arg Asp Gly Gly Thr Leu Tyr Asn Thr
            100                 105                 110

Gln Leu Leu Phe Asp Ala Asp Gly Thr Leu Ile Gln Arg Arg Arg Lys
        115                 120                 125

Ile Thr Pro Thr His Phe Glu Arg Met Ile Trp Gly Gln Gly Asp Gly
    130                 135                 140

Ser Gly Leu Arg Ala Val Asp Ser Lys Val Gly Arg Ile Gly Gln Leu
145                 150                 155                 160

Ala Cys Phe Glu His Asn Asn Pro Leu Ala Arg Tyr Ala Leu Ile Ala
                165                 170                 175

Asp Gly Glu Gln Ile His Ser Ala Met Tyr Pro Gly Ser Ala Phe Gly
            180                 185                 190

Glu Gly Phe Ala Gln Arg Met Glu Ile Asn Ile Arg Gln His Ala Leu
        195                 200                 205

Glu Ser Gly Ala Phe Val Val Asn Ala Thr Ala Trp Leu Asp Ala Asp
```

```
    210                 215                 220

Gln Gln Ala Gln Ile Ile Lys Asp Thr Gly Cys Gly Ile Gly Pro Ile
225                 230                 235                 240

Ser Gly Gly Cys Phe Thr Thr Ile Val Ala Pro Asp Gly Met Leu Met
                245                 250                 255

Ala Glu Pro Leu Arg Ser Gly Glu Gly Glu Val Ile Val Asp Leu Asp
            260                 265                 270

Phe Thr Leu Ile Asp Arg Arg Lys Met Leu Met Asp Ser Ala Gly His
        275                 280                 285

Tyr Asn Arg Pro Glu Leu Leu Ser Leu Met Ile Asp Arg Thr Ala Thr
    290                 295                 300

Ala His Val His Glu Arg Ala Ala His Pro Val Ser Gly Ala Glu Gln
305                 310                 315                 320

Gly Pro Glu Asp Leu Arg Thr Pro Ala Ala
                325                 330


<210> SEQ ID NO 5
<211> LENGTH: 1041
<212> TYPE: DNA
<213> ORGANISM: Agrobacterium rubi

<400> SEQUENCE: 5

atggaaaaga gtaagaccgt gcgtgccgcc gccgcccaga ttgctcctga tctgaccagt      60

cgcgataata ccctggcacg cgttctggat accattcatg aagcagccgg caaaggtgca     120

gaactgattg tgtttccgga aacctttgtg ccgtggtatc cgtattttag ttttgttctg     180

ccgccggttc tgagtggccg tgaacatctg cgtctgtatg aagaagcagt taccgttccg     240

agtgccacca ccgatgcagt ggccaccgca gcacgcgaac atggtattgt ggtggcactg     300

ggtgtgaatg aacgtgatca tggcaccctg tataataccc agctggtgtt tgatgcagat     360

ggcgccctgg tgctgaaacg tcgcaaaatt accccgacct ttcatgaacg tatgatttgg     420

ggccagggtg acgcaagtgg cctgaaagtg gtggatagcc aggttggccg cattggtgca     480

ctggcctgct gggaacatta taatccgctg gcacgttatg ccctgatggc ccagcatgaa     540

gaaattcatg ttgcccagtt tccgggcagc atggtgggcc cgatttttgc agatcagatg     600

gaagtgacca ttcgtcatca tgcactggaa agtggttgtt ttgtggttaa tgccaccggt     660

tggctgaccg atgaacagat tcgtagtatt accccggatg aaaatctgca aaaagcactg     720

cgcggtggct gcatgaccgc cattattagt ccggaaggta aacatctggc accgccgatg     780

accgaaggtg aaggcattct ggtggcagat ttggatatga gcctgattct gaaacgtaaa     840

cgtatgatgg atagtgtggg tcattatgcc cgcccggaac tgctgcatct ggttattgat     900

aatcgtccgg ccattaccat ggtgaccgcc catccgtttc tggaaaccgc accgaccggt     960

agtaataccg atggccatca gaccagcgcc tttgatggca atccggatca gcgcgccgca    1020

attctgcgcc gtcaggcagg c                                               1041


<210> SEQ ID NO 6
<211> LENGTH: 347
<212> TYPE: PRT
<213> ORGANISM: Agrobacterium rubi

<400> SEQUENCE: 6

Met Glu Lys Ser Lys Thr Val Arg Ala Ala Ala Ala Gln Ile Ala Pro
1               5                   10                  15

Asp Leu Thr Ser Arg Asp Asn Thr Leu Ala Arg Val Leu Asp Thr Ile
```

```
            20                  25                  30

His Glu Ala Ala Gly Lys Gly Ala Glu Leu Ile Val Phe Pro Glu Thr
        35                  40                  45

Phe Val Pro Trp Tyr Pro Tyr Phe Ser Phe Val Leu Pro Pro Val Leu
    50                  55                  60

Ser Gly Arg Glu His Leu Arg Leu Tyr Glu Glu Ala Val Thr Val Pro
65                  70                  75                  80

Ser Ala Thr Thr Asp Ala Val Ala Thr Ala Ala Arg Glu His Gly Ile
                85                  90                  95

Val Val Ala Leu Gly Val Asn Glu Arg Asp His Gly Thr Leu Tyr Asn
            100                 105                 110

Thr Gln Leu Val Phe Asp Ala Asp Gly Ala Leu Val Leu Lys Arg Arg
        115                 120                 125

Lys Ile Thr Pro Thr Phe His Glu Arg Met Ile Trp Gly Gln Gly Asp
    130                 135                 140

Ala Ser Gly Leu Lys Val Val Asp Ser Gln Val Gly Arg Ile Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Val Ala Gln Phe Pro Gly Ser Met Val
            180                 185                 190

Gly Pro Ile Phe Ala Asp Gln Met Glu Val Thr Ile Arg His His Ala
        195                 200                 205

Leu Glu Ser Gly Cys Phe Val Val Asn Ala Thr Gly Trp Leu Thr Asp
    210                 215                 220

Glu Gln Ile Arg Ser Ile Thr Pro Asp Glu Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Met Thr Glu Gly Glu Gly Ile Leu Val Ala Asp Leu Asp
            260                 265                 270

Met Ser Leu Ile Leu Lys Arg Lys Arg Met Met Asp Ser Val Gly His
        275                 280                 285

Tyr Ala Arg Pro Glu Leu Leu His Leu Val Ile Asp Asn Arg Pro Ala
    290                 295                 300

Ile Thr Met Val Thr Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345
```

<210> SEQ ID NO 7
<211> LENGTH: 1158
<212> TYPE: DNA
<213> ORGANISM: Candidatus Dadabacteria
<220> FEATURE:
<223> OTHER INFORMATION: Candidatus Dadabacteria bacterium CSP1-2

<400> SEQUENCE: 7

```
atgggtcagg tgctgggtgg tcgtgaacag gttcgtgccg ccgtggttca ggcaagtccg      60

gtttttatga ataagaaagg ttgtctggaa aaggcctgcg atctgattca taaagcaggt     120

aaagaaggcg cagaaattgt ggtgtttccg gaaacctgga ttccgaccta tccgtattgg     180

ggtatgggtt gggataccgc agcagcagca tttgccgatg ttcatgccga tctgcaagat     240
```

```
aatagcctgg tggttggcag caaagatacc gatattctgg gtaaagcagc ccgcgatgcc    300

ggtgcctatg ttgttatggg ctgcaatgaa ctggatgatc gcattggcag ccgtaccctg    360

tttaatagtc tggtttatat tggcaaagac ggccgtgtta tgggtcgtca tcgtaaactg    420

attccgagtt atattgaacg catttggtgg ggtcgcggtg acgcccgtga tctgaaagtt    480

tttgataccg atatcggccg cattggtggt cagatttgtt gggaaaatca tattgttaac    540

atcaccgcct ggtttattgc ccagggcgtt gatattcatg ttgcagtttg gccgggtctg    600

tggaattgtg gtgccgcaca gggtgaaagt tttatctatg caggccatga tattaataag    660

tgcgatctga tcccggccac ccgcgaacgc gcctttaccg gtcagtgctt tgttctgagc    720

gcaaataata ttctgcgcat ggatgaaatt ccggatgatt ttccgtttaa aaataagatg    780

acctacgcag gtccgggtca gggtgaattt gttggctggg catgtggtgg tagtcatatt    840

gttgcaccga ccagcgaata tattgtgccg ccgacctttg atgttgaaac cattctgtat    900

gcagatttga atgccaaata tattaaggtt gtgaagagcg ttttcgatag tctgggccat    960

tatacccgct gggatctggt gagtctgacc aaacagccgc agccgtatga accgctggca   1020

ggcgaacgcc cgatggcaat gccggaagaa cgtattgaac aggttgccga tgcagtggcc   1080

cgtgagttta atctggatgt tgaaaaagtt gataagatcg tgcgtcaggt taccaccccg   1140

catcgtcagc gcgcagcc                                                 1158
```

```
<210> SEQ ID NO 8
<211> LENGTH: 386
<212> TYPE: PRT
<213> ORGANISM: Candidatus Dadabacteria
<220> FEATURE:
<223> OTHER INFORMATION: Candidatus Dadabacteria bacterium CSP1-2

<400> SEQUENCE: 8

Met Gly Gln Val Leu Gly Gly Arg Glu Gln Val Arg Ala Ala Val Val
1               5                   10                  15

Gln Ala Ser Pro Val Phe Met Asn Lys Lys Gly Cys Leu Glu Lys Ala
            20                  25                  30

Cys Asp Leu Ile His Lys Ala Gly Lys Glu Gly Ala Glu Ile Val Val
        35                  40                  45

Phe Pro Glu Thr Trp Ile Pro Thr Tyr Pro Tyr Trp Gly Met Gly Trp
    50                  55                  60

Asp Thr Ala Ala Ala Ala Phe Ala Asp Val His Ala Asp Leu Gln Asp
65                  70                  75                  80

Asn Ser Leu Val Val Gly Ser Lys Asp Thr Asp Ile Leu Gly Lys Ala
                85                  90                  95

Ala Arg Asp Ala Gly Ala Tyr Val Val Met Gly Cys Asn Glu Leu Asp
            100                 105                 110

Asp Arg Ile Gly Ser Arg Thr Leu Phe Asn Ser Leu Val Tyr Ile Gly
        115                 120                 125

Lys Asp Gly Arg Val Met Gly Arg His Arg Lys Leu Ile Pro Ser Tyr
    130                 135                 140

Ile Glu Arg Ile Trp Trp Gly Arg Gly Asp Ala Arg Asp Leu Lys Val
145                 150                 155                 160

Phe Asp Thr Asp Ile Gly Arg Ile Gly Gly Gln Ile Cys Trp Glu Asn
                165                 170                 175

His Ile Val Asn Ile Thr Ala Trp Phe Ile Ala Gln Gly Val Asp Ile
            180                 185                 190
```

His Val Ala Val Trp Pro Gly Leu Trp Asn Cys Gly Ala Ala Gln Gly
195 200 205

Glu Ser Phe Ile Tyr Ala Gly His Asp Ile Asn Lys Cys Asp Leu Ile
210 215 220

Pro Ala Thr Arg Glu Arg Ala Phe Thr Gly Gln Cys Phe Val Leu Ser
225 230 235 240

Ala Asn Asn Ile Leu Arg Met Asp Glu Ile Pro Asp Asp Phe Pro Phe
245 250 255

Lys Asn Lys Met Thr Tyr Ala Gly Pro Gly Gln Gly Glu Phe Val Gly
260 265 270

Trp Ala Cys Gly Gly Ser His Ile Val Ala Pro Thr Ser Glu Tyr Ile
275 280 285

Val Pro Pro Thr Phe Asp Val Glu Thr Ile Leu Tyr Ala Asp Leu Asn
290 295 300

Ala Lys Tyr Ile Lys Val Val Lys Ser Val Phe Asp Ser Leu Gly His
305 310 315 320

Tyr Thr Arg Trp Asp Leu Val Ser Leu Thr Lys Gln Pro Gln Pro Tyr
325 330 335

Glu Pro Leu Ala Gly Glu Arg Pro Met Ala Met Pro Glu Glu Arg Ile
340 345 350

Glu Gln Val Ala Asp Ala Val Ala Arg Glu Phe Asn Leu Asp Val Glu
355 360 365

Lys Val Asp Lys Ile Val Arg Gln Val Thr Thr Pro His Arg Gln Arg
370 375 380

Ala Ala
385

<210> SEQ ID NO 9
<211> LENGTH: 972
<212> TYPE: DNA
<213> ORGANISM: Tepidicaulis marinus

<400> SEQUENCE: 9
atgacccgcg tggcggcgat tcagatggaa gcgaaagtgg cggatctgaa ctttaacatt 60
gatcaggcga gccgcctgat tgatgaagcg ggcagcaaag gcgcggaaat tattgcgctg 120
ccggaatttt ttaccacccg cattgtgtat gatgaacgcc tgtttgaatg cagcctgccg 180
ccggaaaacc cggcgctgga tatgctgaaa gcgaaagcgg cgaaatatgg cgcgatgatt 240
ggcggcagct atctggaaat gcgcgatggc gatgtgtata acacctatac cctggtggaa 300
ccggatggca ccgtgcatcg ccatgataaa gatcgcccga ccatggtgga aaacgcgttt 360
tataccggcg gcagcgatga tggctatttt gaaaccgcga tgggcccggt gggcaccgcg 420
gtgtgctggg aactgattcg caccgcgacc gtgcgccgcc tggcgggcaa agtgggcctg 480
atgatgaccg gcagccattg gtggagcgcg ccgggctgga acttttggaa aagctttgaa 540
cgccgctttc ataaagcgaa cggcaaagcg atggaaatta ccccgccgcg ctttgcgagc 600
ctggtgggcg cgccgctgct gcatgcgggc cataccggca tgctggaagg cggctttctg 660
gtgctgccgg gcacccgcat tagcgtgccg acccgcaccc agctgatggg cgaaacccag 720
attattgatg gcgaaggcgc ggtggtggcg cgccgccatt ataccgaagg cgcgggcatt 780
gtgggcggcg aaattgaact gggcgcgacc agcccgaaaa aagcgccgcc ggatcgcttt 840
tggattccga acctggaagg ctttccgaaa gcgctgtggc tgcatcagaa cccggcgggc 900
gcgagcgtgt atcgctgggc gaaacgcacc ggccgcctga aaacctatga ttttagccgc 960
aacgcgcgcc cg 972

<210> SEQ ID NO 10
<211> LENGTH: 324
<212> TYPE: PRT
<213> ORGANISM: Tepidicaulis marinus

<400> SEQUENCE: 10

Met Thr Arg Val Ala Ala Ile Gln Met Glu Ala Lys Val Ala Asp Leu
1 5 10 15

Asn Phe Asn Ile Asp Gln Ala Ser Arg Leu Ile Asp Glu Ala Gly Ser
20 25 30

Lys Gly Ala Glu Ile Ile Ala Leu Pro Glu Phe Phe Thr Thr Arg Ile
35 40 45

Val Tyr Asp Glu Arg Leu Phe Glu Cys Ser Leu Pro Pro Glu Asn Pro
50 55 60

Ala Leu Asp Met Leu Lys Ala Lys Ala Ala Lys Tyr Gly Ala Met Ile
65 70 75 80

Gly Gly Ser Tyr Leu Glu Met Arg Asp Gly Asp Val Tyr Asn Thr Tyr
85 90 95

Thr Leu Val Glu Pro Asp Gly Thr Val His Arg His Asp Lys Asp Arg
100 105 110

Pro Thr Met Val Glu Asn Ala Phe Tyr Thr Gly Gly Ser Asp Asp Gly
115 120 125

Tyr Phe Glu Thr Ala Met Gly Pro Val Gly Thr Ala Val Cys Trp Glu
130 135 140

Leu Ile Arg Thr Ala Thr Val Arg Arg Leu Ala Gly Lys Val Gly Leu
145 150 155 160

Met Met Thr Gly Ser His Trp Trp Ser Ala Pro Gly Trp Asn Phe Trp
165 170 175

Lys Ser Phe Glu Arg Arg Phe His Lys Ala Asn Gly Lys Ala Met Glu
180 185 190

Ile Thr Pro Pro Arg Phe Ala Ser Leu Val Gly Ala Pro Leu Leu His
195 200 205

Ala Gly His Thr Gly Met Leu Glu Gly Gly Phe Leu Val Leu Pro Gly
210 215 220

Thr Arg Ile Ser Val Pro Thr Arg Thr Gln Leu Met Gly Glu Thr Gln
225 230 235 240

Ile Ile Asp Gly Glu Gly Ala Val Val Ala Arg Arg His Tyr Thr Glu
245 250 255

Gly Ala Gly Ile Val Gly Gly Glu Ile Glu Leu Gly Ala Thr Ser Pro
260 265 270

Lys Lys Ala Pro Pro Asp Arg Phe Trp Ile Pro Asn Leu Glu Gly Phe
275 280 285

Pro Lys Ala Leu Trp Leu His Gln Asn Pro Ala Gly Ala Ser Val Tyr
290 295 300

Arg Trp Ala Lys Arg Thr Gly Arg Leu Lys Thr Tyr Asp Phe Ser Arg
305 310 315 320

Asn Ala Arg Pro

<210> SEQ ID NO 11
<211> LENGTH: 1059
<212> TYPE: DNA
<213> ORGANISM: Sphingomonas wittichii
<220> FEATURE:
<223> OTHER INFORMATION: Sphingomonas wittichii RW1

<400> SEQUENCE: 11

```
atgaacgaag gtttccagaa agttcgtgtt gctgctgctc agatctctcc ggctttcctg     60

gaccgtgaag gttctaccga aatcgcttgc cactggatcg ctgaagctgc tcgtggtggt    120

gctgaactgc tgtctttcgg tgaagcttgg ctgccggctt acccgttctg gatcttcatg    180

ggttctccga tctactctgc tcagttctct cgtcgtctgt acgaaaacgc tgttgaaatc    240

ccgtctgcta ccaccgaccg tctgtgcgaa gctgctcgta aagctggtat ccacgttgtt    300

atgggtctga ccgaactgtg ggtggttct ctgtacctgg ctcagctgtt catcaacgac    360

cgtggtgaaa tcgttggtca ccgtcgtaaa ctgaaaccga cccactggga acgtgctatc    420

tggggtgaag gtgacggttc tgacttcttc gttgttccga cctctatcgg tcgtctgggt    480

gctctgaact gctgggaaca cctgcagccg ctgaacctgt tcgctatgaa cgctttcggt    540

gaacagatcc acgttgctgc ttggccggct ttcgctatct acaaccgtgt tgacccgtct    600

ttcaccaacg aagctaacct ggctgcttct cgtgcttacg ctatggctac ccagaccttc    660

gttatccaca cctctgctgt tgttgacgac gctaccgttg aactgctgtg cgacgacgac    720

gacaaacgtc tgctgctgga atctggtggt ggtcagtgcg ctgttatcaa cccgctgggt    780

gctatcatct ctaccccgct gtcttctacc gctcagggtc tggttttcgc tgactgcgac    840

ttcggtgtta tcgcttctgc taaaatgtct aacgacccgg ctggtcacta ccagcgtggt    900

gacgttttcc aggttcactt caacccggct ccgcgtcgtc cgctggttcc gcgtgctgct    960

atcgctgctg acccgaccac cgctgcttct gaagacctgc cgaacatcaa acacccgccg   1020

ttctctccgg ctgttaaact gccgatcgtt gttgacgac                          1059
```

<210> SEQ ID NO 12
<211> LENGTH: 353
<212> TYPE: PRT
<213> ORGANISM: Sphingomonas wittichii
<220> FEATURE:
<223> OTHER INFORMATION: Sphingomonas wittichii RW1

<400> SEQUENCE: 12

```
Met Asn Glu Gly Phe Gln Lys Val Arg Val Ala Ala Ala Gln Ile Ser
1               5                   10                  15

Pro Ala Phe Leu Asp Arg Glu Gly Ser Thr Glu Ile Ala Cys His Trp
            20                  25                  30

Ile Ala Glu Ala Ala Arg Gly Gly Ala Glu Leu Leu Ser Phe Gly Glu
        35                  40                  45

Ala Trp Leu Pro Ala Tyr Pro Phe Trp Ile Phe Met Gly Ser Pro Ile
    50                  55                  60

Tyr Ser Ala Gln Phe Ser Arg Arg Leu Tyr Glu Asn Ala Val Glu Ile
65                  70                  75                  80

Pro Ser Ala Thr Thr Asp Arg Leu Cys Glu Ala Ala Arg Lys Ala Gly
                85                  90                  95

Ile His Val Val Met Gly Leu Thr Glu Leu Trp Gly Gly Ser Leu Tyr
            100                 105                 110

Leu Ala Gln Leu Phe Ile Asn Asp Arg Gly Glu Ile Val Gly His Arg
        115                 120                 125

Arg Lys Leu Lys Pro Thr His Trp Glu Arg Ala Ile Trp Gly Glu Gly
    130                 135                 140

Asp Gly Ser Asp Phe Phe Val Val Pro Thr Ser Ile Gly Arg Leu Gly
145                 150                 155                 160
```

```
Ala Leu Asn Cys Trp Glu His Leu Gln Pro Leu Asn Leu Phe Ala Met
                165                 170                 175

Asn Ala Phe Gly Glu Gln Ile His Val Ala Ala Trp Pro Ala Phe Ala
            180                 185                 190

Ile Tyr Asn Arg Val Asp Pro Ser Phe Thr Asn Glu Ala Asn Leu Ala
        195                 200                 205

Ala Ser Arg Ala Tyr Ala Met Ala Thr Gln Thr Phe Val Ile His Thr
    210                 215                 220

Ser Ala Val Val Asp Asp Ala Thr Val Glu Leu Leu Cys Asp Asp Asp
225                 230                 235                 240

Asp Lys Arg Leu Leu Leu Glu Ser Gly Gly Gly Gln Cys Ala Val Ile
                245                 250                 255

Asn Pro Leu Gly Ala Ile Ile Ser Thr Pro Leu Ser Ser Thr Ala Gln
            260                 265                 270

Gly Leu Val Phe Ala Asp Cys Asp Phe Gly Val Ile Ala Ser Ala Lys
        275                 280                 285

Met Ser Asn Asp Pro Ala Gly His Tyr Gln Arg Gly Asp Val Phe Gln
    290                 295                 300

Val His Phe Asn Pro Ala Pro Arg Arg Pro Leu Val Pro Arg Ala Ala
305                 310                 315                 320

Ile Ala Ala Asp Pro Thr Thr Ala Ala Ser Glu Asp Leu Pro Asn Ile
                325                 330                 335

Lys His Pro Pro Phe Ser Pro Ala Val Lys Leu Pro Ile Val Val Asp
            340                 345                 350

Asp


<210> SEQ ID NO 13
<211> LENGTH: 1062
<212> TYPE: DNA
<213> ORGANISM: Rhizobium sp.
<220> FEATURE:
<223> OTHER INFORMATION: Rhizobium sp. YK2

<400> SEQUENCE: 13

atggaaaaca aatctatcgt tcgtgctgct gctgttcaga tcgctccgga cctgacctct      60

cgtgaaaaaa ccctggctcg tgttctggaa gctatccacg aagctgctgg taaaggtgct     120

gaactggctg ttttcccgga aaccttcgtt ccgtggtacc cgtacttctc tttcgttctg     180

ccgccggttc tgtctggtaa agaacacgtt cgtctgtacg acgaagctgt taccgttccg     240

tctgctgcta ccgaagctat cgctaccgct gctcgtaacc acggtatcgt tgttgttctg     300

ggtgttaacg aacgtgacca cggttctctg tacaacaccc agctggtttt caacgctgac     360

ggtaccctga tcctgaaacg tcgtaaaatc accccgacct tccacgaacg tatgatctgg     420

ggtcagggtg acgcttctgg tctgaccgtt gttgaatctc acgttggtcg tatcggtgct     480

ctggcttgct gggaacacta caacccgctg gctcgttacg ctctgatggc tcagcacgaa     540

gaaatccacg ttgctcagtt cccgggttct atggttggtc cgatcttcgc tgaacagatc     600

gaagttacca tccgtcacca cgctctggaa tctggttgct tcgttgttaa cgctaccggt     660

tggctgaccg acgaacagat cgcttctatc accccggacc agaacctgca gaaagctctg     720

cgtggtggtt gcatgaccgc tatcatctct ccggaaggta aacacctggc tccgccgctg     780

accgaaggtg aaggtatcct gatcgctgac ctggacatgt ctctgatcac caaacgtaaa     840

cgtatgatgg actctgttgg tcactacgct cgtccggaac tgctgcacct ggttatcgac     900

ggtcgtgcta ccgctccgat ggttgcttct gaatcttctt tcgaaaaccg taacccgtct     960
```

cagaccgctt ctccgcgttc taactctgac ggtcaccacg acaacgcttc ttctgaccgt 1020
gacccggacc agcgtgttgc tgttctgcgt tctcaggctt ct 1062

<210> SEQ ID NO 14
<211> LENGTH: 354
<212> TYPE: PRT
<213> ORGANISM: Rhizobium sp.
<220> FEATURE:
<223> OTHER INFORMATION: Rhizobium sp. YK2

<400> SEQUENCE: 14

```
Met Glu Asn Lys Ser Ile Val Arg Ala Ala Ala Val Gln Ile Ala Pro
1               5                   10                  15

Asp Leu Thr Ser Arg Glu Lys Thr Leu Ala Arg Val Leu Glu Ala Ile
            20                  25                  30

His Glu Ala Ala Gly Lys Gly Ala Glu Leu Ala Val Phe Pro Glu Thr
        35                  40                  45

Phe Val Pro Trp Tyr Pro Tyr Phe Ser Phe Val Leu Pro Pro Val Leu
    50                  55                  60

Ser Gly Lys Glu His Val Arg Leu Tyr Asp Glu Ala Val Thr Val Pro
65                  70                  75                  80

Ser Ala Ala Thr Glu Ala Ile Ala Thr Ala Ala Arg Asn His Gly Ile
                85                  90                  95

Val Val Val Leu Gly Val Asn Glu Arg Asp His Gly Ser Leu Tyr Asn
            100                 105                 110

Thr Gln Leu Val Phe Asn Ala Asp Gly Thr Leu Ile Leu Lys Arg Arg
        115                 120                 125

Lys Ile Thr Pro Thr Phe His Glu Arg Met Ile Trp Gly Gln Gly Asp
    130                 135                 140

Ala Ser Gly Leu Thr Val Val Glu Ser His Val Gly Arg Ile Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Val Ala Gln Phe Pro Gly Ser Met Val
            180                 185                 190

Gly Pro Ile Phe Ala Glu Gln Ile Glu Val Thr Ile Arg His His Ala
        195                 200                 205

Leu Glu Ser Gly Cys Phe Val Val Asn Ala Thr Gly Trp Leu Thr Asp
    210                 215                 220

Glu Gln Ile Ala Ser Ile Thr Pro Asp Gln Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Leu Thr Glu Gly Glu Gly Ile Leu Ile Ala Asp Leu Asp
            260                 265                 270

Met Ser Leu Ile Thr Lys Arg Lys Arg Met Met Asp Ser Val Gly His
        275                 280                 285

Tyr Ala Arg Pro Glu Leu Leu His Leu Val Ile Asp Gly Arg Ala Thr
    290                 295                 300

Ala Pro Met Val Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
```

340 345 350

Ala Ser

<210> SEQ ID NO 15
<211> LENGTH: 996
<212> TYPE: DNA
<213> ORGANISM: Synechococcus sp.
<220> FEATURE:
<223> OTHER INFORMATION: Synechococcus sp. CC9605

<400> SEQUENCE: 15
atgaccaccg tgaaagtggc ggcggcgcag attcgcccgg tgctgtttag cctggatggc 60
agcctgcaga aagtgctgga tgcgatggcg gaagcggcgg cgcagggcgt ggaactgatt 120
gtgtttccgg aaacctttct gccgtattat ccgtatttta gctttgtgga accgccggtg 180
ctgatgggcc gcagccatct ggcgctgtat gaacaggcgg tggtggtgcc gggcccggtg 240
accgatgcgg tggcggcggc ggcgagccag tatggcatgc aggtgctgct gggcgtgaac 300
gaacgcgatg gcggcaccct gtataacacc cagctgctgt ttaacagctg cggcgaactg 360
gtgctgaaac gccgcaaaat taccccgacc tatcatgaac gcatggtgtg gggccagggc 420
gatggcagcg gcctgaaagt ggtgcagacc ccgctggcgc gcgtgggcgc gctggcgtgc 480
tgggaacatt ataacccgct ggcgcgctat gcgctgatgg cgcagggcga agaaattcat 540
tgcgcgcagt ttccgggcag cctggtgggc ccgattttta ccgaacagac cgcggtgacc 600
atgcgccatc atgcgctgga agcgggctgc tttgtgattt gcagcaccgg ctggctgcat 660
ccggatgatt atgcgagcat taccagcgaa agcggcctgc ataaagcgtt tcagggcggc 720
tgccataccg cggtgattag cccggaaggc cgctatctgg cgggcccgct gccggatggc 780
gaaggcctgg cgattgcgga tctggatctg gcgctgatta ccaaacgcaa acgcatgatg 840
gatagcgtgg gccattatag ccgcccggaa ctgctgagcc tgcagattaa cagcagcccg 900
gcggtgccgg tgcagaacat gagcaccgcg agcgtgccgc tggaaccggc gaccgcgacc 960
gatgcgctga gcagcatgga agcgctgaac catgtg 996

<210> SEQ ID NO 16
<211> LENGTH: 332
<212> TYPE: PRT
<213> ORGANISM: Synechococcus sp.
<220> FEATURE:
<223> OTHER INFORMATION: Synechococcus sp. CC9605

<400> SEQUENCE: 16

Met Thr Thr Val Lys Val Ala Ala Ala Gln Ile Arg Pro Val Leu Phe
1 5 10 15

Ser Leu Asp Gly Ser Leu Gln Lys Val Leu Asp Ala Met Ala Glu Ala
20 25 30

Ala Ala Gln Gly Val Glu Leu Ile Val Phe Pro Glu Thr Phe Leu Pro
35 40 45

Tyr Tyr Pro Tyr Phe Ser Phe Val Glu Pro Pro Val Leu Met Gly Arg
50 55 60

Ser His Leu Ala Leu Tyr Glu Gln Ala Val Val Val Pro Gly Pro Val
65 70 75 80

Thr Asp Ala Val Ala Ala Ala Ala Ser Gln Tyr Gly Met Gln Val Leu
85 90 95

Leu Gly Val Asn Glu Arg Asp Gly Gly Thr Leu Tyr Asn Thr Gln Leu
100 105 110

```
Leu Phe Asn Ser Cys Gly Glu Leu Val Leu Lys Arg Arg Lys Ile Thr
        115                 120                 125

Pro Thr Tyr His Glu Arg Met Val Trp Gly Gln Gly Asp Gly Ser Gly
    130                 135                 140

Leu Lys Val Val Gln Thr Pro Leu Ala Arg Val Gly Ala Leu Ala Cys
145                 150                 155                 160

Trp Glu His Tyr Asn Pro Leu Ala Arg Tyr Ala Leu Met Ala Gln Gly
                165                 170                 175

Glu Glu Ile His Cys Ala Gln Phe Pro Gly Ser Leu Val Gly Pro Ile
            180                 185                 190

Phe Thr Glu Gln Thr Ala Val Thr Met Arg His His Ala Leu Glu Ala
        195                 200                 205

Gly Cys Phe Val Ile Cys Ser Thr Gly Trp Leu His Pro Asp Asp Tyr
    210                 215                 220

Ala Ser Ile Thr Ser Glu Ser Gly Leu His Lys Ala Phe Gln Gly Gly
225                 230                 235                 240

Cys His Thr Ala Val Ile Ser Pro Glu Gly Arg Tyr Leu Ala Gly Pro
                245                 250                 255

Leu Pro Asp Gly Glu Gly Leu Ala Ile Ala Asp Leu Asp Leu Ala Leu
            260                 265                 270

Ile Thr Lys Arg Lys Arg Met Met Asp Ser Val Gly His Tyr Ser Arg
        275                 280                 285

Pro Glu Leu Leu Ser Leu Gln Ile Asn Ser Ser Pro Ala Val Pro Val
    290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330
```

<210> SEQ ID NO 17

<400> SEQUENCE: 17

000

<210> SEQ ID NO 18

<400> SEQUENCE: 18

000

<210> SEQ ID NO 19
<211> LENGTH: 969
<212> TYPE: DNA
<213> ORGANISM: Flavihumibacter solisilvae

<400> SEQUENCE: 19

```
atgagccata gtaccaataa taacagcagc accgttgttc gtgcagcagc cgtgcagatt      60

agcccggttc tgtatagtcg cgaaggcacc acccagaaag tggtgaatac cattcgtgaa     120

ctgggtaaac agggcgtgca gtttgcagtg tttccggaaa cctttattcc gtattatccg     180

tattttagtt tcgttcagcc gccgtatatg caggcagaac agcatctgaa actgatggaa     240

gaagcagtga ccgttccgag tgccaccacc gatgcaattg gcgaagccgc ccgtgaagcc     300

ggtattgttg ttagtattgg cgtgaatgaa cgtgatggtg gtagtctgta taatacccag     360

ctgctgtttg atgccgatgg taccctgatt cagcgccgtc gcaaaattac cccgacctat     420

catgaacgca tggtttgggg tcagggcgat ggtagcggcc tgcgcgctgt ggatagtaaa     480
```

```
gcaggccgta ttggccagct ggcatgttgg gaacattata atccgctggc ccgttatgca    540

atgattgccg atggtgaaca gattcatgca gcaatgtatc cgggcagcag ctttggcgaa    600

ctgtttagcc agcagattga agttagtgtt cgtcagcatg ccctggaaag tgccgccttt    660

gttgttagta gcaccgcatg gctggatgcc gatcagcagg cccagattat gaaagatacc    720

ggcagcccga ttggtccgat tagcggtggt aattttaccg ccattattgc cccggatggt    780

accattattg gcgaaccgat tcgtagcggc gaaggctttg tgattgcaga tttggatttt    840

aatctgattg agaaacgcaa acgtctgatg gatctgaaag gccattataa tcgcccggaa    900

ctgctgagtc tgctgattga tcgcaccccg gccgaatatg ttcaggaagt gaataagagt    960

gttagcgaa                                                            969
```

<210> SEQ ID NO 20
<211> LENGTH: 323
<212> TYPE: PRT
<213> ORGANISM: Flavihumibacter solisilvae

<400> SEQUENCE: 20

```
Met Ser His Ser Thr Asn Asn Asn Ser Ser Thr Val Val Arg Ala Ala
1               5                   10                  15

Ala Val Gln Ile Ser Pro Val Leu Tyr Ser Arg Glu Gly Thr Thr Gln
            20                  25                  30

Lys Val Val Asn Thr Ile Arg Glu Leu Gly Lys Gln Gly Val Gln Phe
        35                  40                  45

Ala Val Phe Pro Glu Thr Phe Ile Pro Tyr Tyr Pro Tyr Phe Ser Phe
    50                  55                  60

Val Gln Pro Pro Tyr Met Gln Ala Glu Gln His Leu Lys Leu Met Glu
65                  70                  75                  80

Glu Ala Val Thr Val Pro Ser Ala Thr Thr Asp Ala Ile Gly Glu Ala
                85                  90                  95

Ala Arg Glu Ala Gly Ile Val Val Ser Ile Gly Val Asn Glu Arg Asp
            100                 105                 110

Gly Gly Ser Leu Tyr Asn Thr Gln Leu Leu Phe Asp Ala Asp Gly Thr
        115                 120                 125

Leu Ile Gln Arg Arg Arg Lys Ile Thr Pro Thr Tyr His Glu Arg Met
    130                 135                 140

Val Trp Gly Gln Gly Asp Gly Ser Gly Leu Arg Ala Val Asp Ser Lys
145                 150                 155                 160

Ala Gly Arg Ile Gly Gln Leu Ala Cys Trp Glu His Tyr Asn Pro Leu
                165                 170                 175

Ala Arg Tyr Ala Met Ile Ala Asp Gly Glu Gln Ile His Ala Ala Met
            180                 185                 190

Tyr Pro Gly Ser Ser Phe Gly Glu Leu Phe Ser Gln Gln Ile Glu Val
        195                 200                 205

Ser Val Arg Gln His Ala Leu Glu Ser Ala Ala Phe Val Val Ser Ser
    210                 215                 220

Thr Ala Trp Leu Asp Ala Asp Gln Gln Ala Gln Ile Met Lys Asp Thr
225                 230                 235                 240

Gly Ser Pro Ile Gly Pro Ile Ser Gly Gly Asn Phe Thr Ala Ile Ile
                245                 250                 255

Ala Pro Asp Gly Thr Ile Ile Gly Glu Pro Ile Arg Ser Gly Glu Gly
            260                 265                 270

Phe Val Ile Ala Asp Leu Asp Phe Asn Leu Ile Glu Lys Arg Lys Arg
```

```
        275                 280                 285

Leu Met Asp Leu Lys Gly His Tyr Asn Arg Pro Glu Leu Leu Ser Leu
    290                 295                 300

Leu Ile Asp Arg Thr Pro Ala Glu Tyr Val Gln Glu Val Asn Lys Ser
305                 310                 315                 320

Val Ser Glu


<210> SEQ ID NO 21
<211> LENGTH: 1035
<212> TYPE: DNA
<213> ORGANISM: Salinisphaera shabanensis
<220> FEATURE:
<223> OTHER INFORMATION: Salinisphaera shabanensis E1L3A

<400> SEQUENCE: 21

atgacccagt ctcagatcgt taaagttgct gctgttcagc tgcagccggt tctggactct     60

gctgacggta ccgttgaacg tgttctggac gaaatcgctg ctgctgctgc tgacggtgct    120

cagctggttg ttttcccgga aaccgctgtt ccgtactacc cgtactggtc tttcgttatg    180

gctccgatgg acatgggtgc tcgtcaccgt gctctgtacg accactctcc gaccgttccg    240

ggtccggtta ccgacgctgt tgctgctgct gctcgtaccc acgaaatcgt tgttgttctg    300

ggtgttaacg aacgtgacca cggtaccctg tacaactgcc agctggtttt cgacggtaac    360

ggtgaaatcg ctctgaaacg tcgtaaaatc accccgacct accacgaacg tatggtttgg    420

ggtcagggtg acggttctgg tctgcacgct gttgacaccg ctgttggtcg tgttggtgct    480

ctggcttgct gggaacacta caacccgctg gctcgttacg ctctgatggc tgaccacgaa    540

cagatccact gctctcagtt cccgggttct ctggttggtc cgatcttcgc tgaacagcag    600

gaagttaccc tgcgtcacca cgctctggaa tctggttgct tcgttgttaa cgctaccgct    660

tggctggacg ctgaccaggt tgcttctgtt accgaagacc cggctctgca gaaaggtctg    720

ttcggtggtt gctacaccgc tatcatcgct ccggacggtt ctcacgttgt tgctccgctg    780

ctggacggtc cgggtcgtct ggttgctgac atcgacctgt ctctgatcac caaacgtaaa    840

cgtatgatgg actctgttgg tcactacgct cgtccggaac tgctgtctct gcgtatcgac    900

cgtcgttctc acgctgctca gcacgctgac gctgctccgg gtgttggtgc tgtttctgaa    960

ttcgaagaac cggaccacgg tgaaccggaa ccgtacgctg cttaccgtga cgctatcgct   1020

cgttcttcta ccggt                                                     1035


<210> SEQ ID NO 22
<211> LENGTH: 345
<212> TYPE: PRT
<213> ORGANISM: Salinisphaera shabanensis
<220> FEATURE:
<223> OTHER INFORMATION: Salinisphaera shabanensis E1L3A

<400> SEQUENCE: 22

Met Thr Gln Ser Gln Ile Val Lys Val Ala Ala Val Gln Leu Gln Pro
1               5                   10                  15

Val Leu Asp Ser Ala Asp Gly Thr Val Glu Arg Val Leu Asp Glu Ile
            20                  25                  30

Ala Ala Ala Ala Ala Asp Gly Ala Gln Leu Val Val Phe Pro Glu Thr
        35                  40                  45

Ala Val Pro Tyr Tyr Pro Tyr Trp Ser Phe Val Met Ala Pro Met Asp
    50                  55                  60

Met Gly Ala Arg His Arg Ala Leu Tyr Asp His Ser Pro Thr Val Pro
```

```
65                  70                  75                  80

Gly Pro Val Thr Asp Ala Val Ala Ala Ala Ala Arg Thr His Glu Ile
                85                  90                  95

Val Val Val Leu Gly Val Asn Glu Arg Asp His Gly Thr Leu Tyr Asn
            100                 105                 110

Cys Gln Leu Val Phe Asp Gly Asn Gly Glu Ile Ala Leu Lys Arg Arg
        115                 120                 125

Lys Ile Thr Pro Thr Tyr His Glu Arg Met Val Trp Gly Gln Gly Asp
    130                 135                 140

Gly Ser Gly Leu His Ala Val Asp Thr Ala Val Gly Arg Val Gly Ala
145                 150                 155                 160

Leu Ala Cys Trp Glu His Tyr Asn Pro Leu Ala Arg Tyr Ala Leu Met
                165                 170                 175

Ala Asp His Glu Gln Ile His Cys Ser Gln Phe Pro Gly Ser Leu Val
            180                 185                 190

Gly Pro Ile Phe Ala Glu Gln Gln Glu Val Thr Leu Arg His His Ala
        195                 200                 205

Leu Glu Ser Gly Cys Phe Val Val Asn Ala Thr Ala Trp Leu Asp Ala
    210                 215                 220

Asp Gln Val Ala Ser Val Thr Glu Asp Pro Ala Leu Gln Lys Gly Leu
225                 230                 235                 240

Phe Gly Gly Cys Tyr Thr Ala Ile Ile Ala Pro Asp Gly Ser His Val
                245                 250                 255

Val Ala Pro Leu Leu Asp Gly Pro Gly Arg Leu Val Ala Asp Ile Asp
            260                 265                 270

Leu Ser Leu Ile Thr Lys Arg Lys Arg Met Met Asp Ser Val Gly His
        275                 280                 285

Tyr Ala Arg Pro Glu Leu Leu Ser Leu Arg Ile Asp Arg Arg Ser His
    290                 295                 300

Ala Ala Gln His Ala Asp Ala Ala Pro Gly Val Gly Ala Val Ser Glu
305                 310                 315                 320

Phe Glu Glu Pro Asp His Gly Glu Pro Glu Pro Tyr Ala Ala Tyr Arg
                325                 330                 335

Asp Ala Ile Ala Arg Ser Ser Thr Gly
            340                 345
```

<210> SEQ ID NO 23
<211> LENGTH: 954
<212> TYPE: DNA
<213> ORGANISM: Erythrobacter sp.
<220> FEATURE:
<223> OTHER INFORMATION: Erythrobacter sp. JL475

<400> SEQUENCE: 23

```
atgaccaaac tggctgttgc tatctgccag gctgctccgg ttccgctgga cttcgctggt     60

ggtatcgaaa aagctgttcg tctggctcgt gaagctatcg aaggtggtgc tcgtttcgtt    120

gctttcggtg aaaccttcct gggtggttac ccgctgtggc tggacgaagc tccgggtgct    180

gctctgtggg accacccggg taccaaagct ctgcacgcta tcatgctgga acaggctatc    240

gttgctaacg acgaacgtct gctgccgctg caggaactgt gcgacgaatc tggtgcttgc    300

atctctatcg gtgctcacga acgtgttcgt cagtctctgt acaacaacca gctgctgttc    360

cgtccgggtg aagctccgct ggaccaccgt aaactggttc cgacccacgg tgaacgtctg    420

atctggatgc gtggtgacgg ttctaccctg ggtgttcacg aagctgaatg ggtcgtgct     480
```

```
ggtaacctga tctgctggga acactggatg ccgctggctc gtgctgctat gcacaacctg    540

ggtgaatctg ttcacgttgc tgcttggccg accgttcgtg aagaatacgc tctggcttct    600

cgtcactacg ctatggaagg tcgttgcttc gttctggctg ctggtctggt tcagcaccgt    660

gacgacctgt tcgacggtct ggaacgtgtt ggtggtaacg acgaagctaa agctctgttc    720

gaagctatcg aaggtgaaca gctgaaccgt ggtggttcta tgatcatcgc tccggacgct    780

cgtgttctgg ctcaggctgg tgaaggtgaa gaaatcctgc acgctgaact ggacctgtct    840

gaaatcggtc agggtctggc ttctctggac accgacggtc actactctcg tccggacgtt    900

ttcgaactgt ctctggacat gcgtgctaaa gacggtgttg ttcgtaaatc tgaa          954
```

<210> SEQ ID NO 24
<211> LENGTH: 318
<212> TYPE: PRT
<213> ORGANISM: Erythrobacter sp.
<220> FEATURE:
<223> OTHER INFORMATION: Erythrobacter sp. JL475

<400> SEQUENCE: 24

```
Met Thr Lys Leu Ala Val Ala Ile Cys Gln Ala Ala Pro Val Pro Leu
1               5                   10                  15

Asp Phe Ala Gly Gly Ile Glu Lys Ala Val Arg Leu Ala Arg Glu Ala
            20                  25                  30

Ile Glu Gly Gly Ala Arg Phe Val Ala Phe Gly Glu Thr Phe Leu Gly
        35                  40                  45

Gly Tyr Pro Leu Trp Leu Asp Glu Ala Pro Gly Ala Ala Leu Trp Asp
    50                  55                  60

His Pro Gly Thr Lys Ala Leu His Ala Ile Met Leu Glu Gln Ala Ile
65                  70                  75                  80

Val Ala Asn Asp Glu Arg Leu Leu Pro Leu Gln Glu Leu Cys Asp Glu
                85                  90                  95

Ser Gly Ala Cys Ile Ser Ile Gly Ala His Glu Arg Val Arg Gln Ser
            100                 105                 110

Leu Tyr Asn Asn Gln Leu Leu Phe Arg Pro Gly Glu Ala Pro Leu Asp
        115                 120                 125

His Arg Lys Leu Val Pro Thr His Gly Glu Arg Leu Ile Trp Met Arg
    130                 135                 140

Gly Asp Gly Ser Thr Leu Gly Val His Glu Ala Glu Trp Gly Arg Ala
145                 150                 155                 160

Gly Asn Leu Ile Cys Trp Glu His Trp Met Pro Leu Ala Arg Ala Ala
                165                 170                 175

Met His Asn Leu Gly Glu Ser Val His Val Ala Ala Trp Pro Thr Val
            180                 185                 190

Arg Glu Glu Tyr Ala Leu Ala Ser Arg His Tyr Ala Met Glu Gly Arg
        195                 200                 205

Cys Phe Val Leu Ala Ala Gly Leu Val Gln His Arg Asp Asp Leu Phe
    210                 215                 220

Asp Gly Leu Glu Arg Val Gly Gly Asn Asp Glu Ala Lys Ala Leu Phe
225                 230                 235                 240

Glu Ala Ile Glu Gly Glu Gln Leu Asn Arg Gly Gly Ser Met Ile Ile
                245                 250                 255

Ala Pro Asp Ala Arg Val Leu Ala Gln Ala Gly Glu Gly Glu Glu Ile
            260                 265                 270

Leu His Ala Glu Leu Asp Leu Ser Glu Ile Gly Gln Gly Leu Ala Ser
        275                 280                 285
```

Leu Asp Thr Asp Gly His Tyr Ser Arg Pro Asp Val Phe Glu Leu Ser
290 295 300

Leu Asp Met Arg Ala Lys Asp Gly Val Val Arg Lys Ser Glu
305 310 315

<210> SEQ ID NO 25
<211> LENGTH: 1011
<212> TYPE: DNA
<213> ORGANISM: Unknown
<220> FEATURE:
<223> OTHER INFORMATION: Unknown prokaryotic organism

<400> SEQUENCE: 25
atgaaagaag cgattaaagt ggcgtgcgtg caggcggcgc cgatttatat ggatctggaa 60
gcgaccgtgg ataaaaccat tgaactgatg gaagaagcgg cgcgcaacaa cgcgcgcctg 120
attgcgtttc cggaaacctg gattccgggc tatccgtggt ttctgtggct ggatagcccg 180
gcgtgggcga tgcagtttgt gcgccagtat catgaaaaca gcctggaact ggatggcccg 240
caggcgaaac gcattagcga tgcggcgaaa cgcctgggca ttatggtgac cctgggcatg 300
agcgaacgcg tgggcggcac cctgtatatt agccagtggt ttattggcga taacggcgat 360
accattggcg cgcgccgcaa actgaaaccg acctttgtgg aacgcaccct gtttggcgaa 420
ggcgatggca gcagcctggc ggtgtttgaa accagcgtgg gccgcctggg cggcctgtgc 480
tgctgggaac atctgcagcc gctgaccaaa tatgcgctgt atgcgcagaa cgaagaaatt 540
cattgcgcgg cgtggccgag ctttagcctg tatccgaacg cggcgaaagc gctgggcccg 600
gatgtgaacg tggcggcgag ccgcatttat gcggtggaag gccagtgctt tgtgctggcg 660
agctgcgcgc tggtgagcca gagcatgatt gatatgctgt gcaccgatga tgaaaaacat 720
gcgctgctgc tggcgggcgg cggccatagc cgcattattg gcccggatgg cggcgatctg 780
gtggcgccgc tggcggaaaa cgaagaaggc attctgtatg cgaacctgga tccgggcgtg 840
cgcattctgg cgaaaatggc ggcggatccg gcgggccatt atagccgccc ggatattacc 900
cgcctgctga ttgatcgcag cccgaaactg ccggtggtgg aaattgaagg cgatctgcgc 960
ccgtatgcgc tgggcaaagc gagcgaaacc ggcgcgcagc tggaagaaat t 1011

<210> SEQ ID NO 26
<211> LENGTH: 337
<212> TYPE: PRT
<213> ORGANISM: Unknown
<220> FEATURE:
<223> OTHER INFORMATION: Unknown prokaryotic organism

<400> SEQUENCE: 26

Met Lys Glu Ala Ile Lys Val Ala Cys Val Gln Ala Ala Pro Ile Tyr
1 5 10 15

Met Asp Leu Glu Ala Thr Val Asp Lys Thr Ile Glu Leu Met Glu Glu
20 25 30

Ala Ala Arg Asn Asn Ala Arg Leu Ile Ala Phe Pro Glu Thr Trp Ile
35 40 45

Pro Gly Tyr Pro Trp Phe Leu Trp Leu Asp Ser Pro Ala Trp Ala Met
50 55 60

Gln Phe Val Arg Gln Tyr His Glu Asn Ser Leu Glu Leu Asp Gly Pro
65 70 75 80

Gln Ala Lys Arg Ile Ser Asp Ala Ala Lys Arg Leu Gly Ile Met Val
85 90 95

```
Thr Leu Gly Met Ser Glu Arg Val Gly Gly Thr Leu Tyr Ile Ser Gln
            100                 105                 110

Trp Phe Ile Gly Asp Asn Gly Asp Thr Ile Gly Ala Arg Arg Lys Leu
        115                 120                 125

Lys Pro Thr Phe Val Glu Arg Thr Leu Phe Gly Glu Gly Asp Gly Ser
    130                 135                 140

Ser Leu Ala Val Phe Glu Thr Ser Val Gly Arg Leu Gly Gly Leu Cys
145                 150                 155                 160

Cys Trp Glu His Leu Gln Pro Leu Thr Lys Tyr Ala Leu Tyr Ala Gln
                165                 170                 175

Asn Glu Glu Ile His Cys Ala Ala Trp Pro Ser Phe Ser Leu Tyr Pro
            180                 185                 190

Asn Ala Ala Lys Ala Leu Gly Pro Asp Val Asn Val Ala Ala Ser Arg
        195                 200                 205

Ile Tyr Ala Val Glu Gly Gln Cys Phe Val Leu Ala Ser Cys Ala Leu
    210                 215                 220

Val Ser Gln Ser Met Ile Asp Met Leu Cys Thr Asp Asp Glu Lys His
225                 230                 235                 240

Ala Leu Leu Leu Ala Gly Gly Gly His Ser Arg Ile Ile Gly Pro Asp
                245                 250                 255

Gly Gly Asp Leu Val Ala Pro Leu Ala Glu Asn Glu Glu Gly Ile Leu
            260                 265                 270

Tyr Ala Asn Leu Asp Pro Gly Val Arg Ile Leu Ala Lys Met Ala Ala
        275                 280                 285

Asp Pro Ala Gly His Tyr Ser Arg Pro Asp Ile Thr Arg Leu Leu Ile
    290                 295                 300

Asp Arg Ser Pro Lys Leu Pro Val Val Glu Ile Glu Gly Asp Leu Arg
305                 310                 315                 320

Pro Tyr Ala Leu Gly Lys Ala Ser Glu Thr Gly Ala Gln Leu Glu Glu
                325                 330                 335

Ile
```

<210> SEQ ID NO 27
<211> LENGTH: 5365
<212> TYPE: DNA
<213> ORGANISM: Artificial sequence
<220> FEATURE:
<223> OTHER INFORMATION: Plasmid

<400> SEQUENCE: 27

```
cgatcaccac aattcagcaa attgtgaaca tcatcacgtt catctttccc tggttgccaa     60

tggcccattt tcctgtcagt aacgagaagg tcgcgaattc aggcgctttt tagactggtc    120

gtaatgaaca attcttaaga aggagatata catatgcaga caagaaaaat cgtccgggca    180

gccgccgtac aggccgcctc tcccaactac gatctggcaa cgggtgttga taaaaccatt    240

gagctggctc gtcaggcccg cgatgagggc tgtgacctga tcgtgtttgg tgaaacctgg    300

ctgcccggat atcccttcca cgtctggctg ggcgcaccgg cctggtcgct gaaatacagt    360

gcccgctact atgccaactc gctctcgctg gacagtgcag agtttcaacg cattgcccag    420

gccgcacgga ccttgggtat tttcatcgca ctgggttata gcgagcgcag cggcggcagc    480

ctttacctgg gccaatgcct gatcgacgac aagggcgaga tgctgtggtc gcgtcgcaaa    540

ctcaaaccca cgcatgtaga gcgcaccgta tttggtgaag gttatgcccg tgatctgatt    600

gtgtccgaca cagaactggg acgcgtcggt gctctatgct gctgggagca tttgtcgccc    660
```

ttgagcaagt acgcgctgta ctcccagcat gaagccattc acattgctgc ctggccgtcg 720
ttttcgctat acagcgaaca ggcccacgcc ctcagtgcca aggtgaacat ggctgcctcg 780
caaatctatt cggttgaagg ccagtgcttt accatcgccg ccagcagtgt ggtcacccaa 840
gagacgctag acatgctgga agtgggtgaa cacaacgccc ccttgctgaa agtgggcggc 900
ggcagttcca tgatttttgc gccggacgga cgcacactgg ctccctacct gcctcacgat 960
gccgagggct tgatcattgc cgatctgaat atggaggaga ttgccttcgc caaagcgatc 1020
aatgaccccg taggccacta ttccaaaccc gaggccaccc gtctggtgct ggacttgggg 1080
caccgagacc ccatgactcg ggtgcactcc aaaagcgtga ccagggaaga ggctcccgag 1140
caaggtgtgc aaagcaagat tgcctcagtc gctatcagcc atccacagga ctcggacaca 1200
ctgctagtgc aagagccgtc cttgaggatc cgtcgacctg cagccaagct tggctgtttt 1260
ggcggatgag agaagatttt cagcctgata cagattaaat cagaacgcag aagcggtctg 1320
ataaaacaga atttgcctgg cggcagtagc gcggtggtcc cacctgaccc catgccgaac 1380
tcagaagtga aacgccgtag cgccgatggt agtgtggggt ctccccatgc gagagtaggg 1440
aactgccagg catcaaataa aacgaaaggc tcagtcgaaa gactgggcct ttcgttttat 1500
ctgttgtttg tcggtgaacg ctctcctgag taggacaaat ccgccgggag cggatttgaa 1560
cgttgcgaag caacggcccg gagggtggcg ggcaggacgc ccgccataaa ctgccaggca 1620
tcaaattaag cagaaggcca tcctgacgga tggccttttt gcgtttctac aaactctttt 1680
gtttattttt ctaaatacat tcaaatatgt atccgctcat gagacaataa ccctgataaa 1740
tgcttcaata atattgaaaa aggaagagta tgagtattca acatttccgt gtcgccctta 1800
ttcccttttt tgcggcattt tgccttcctg tttttgctca cccagaaacg ctggtgaaag 1860
taaaagatgc tgaagatcag ttgggtgcac gagtgggtta catcgaactg gatctcaaca 1920
gcggtaagat ccttgagagt tttcgccccg aagaacgttt tccaatgatg agcactttta 1980
aagttctgct atgtggcgcg gtattatccc gtgttgacgc cgggcaagag caactcggtc 2040
gccgcataca ctattctcag aatgacttgg ttgagtactc accagtcaca gaaaagcatc 2100
ttacggatgg catgacagta agagaattat gcagtgctgc cataaccatg agtgataaca 2160
ctgcggccaa cttacttctg acaacgatcg gaggaccgaa ggagctaacc gcttttttgc 2220
acaacatggg ggatcatgta actcgccttg atcgttggga accggagctg aatgaagcca 2280
taccaaacga cgagcgtgac accacgatgc ctgtagcaat ggcaacaacg ttgcgcaaac 2340
tattaactgg cgaactactt actctagctt cccggcaaca attaatagac tggatggagg 2400
cggataaagt tgcaggacca cttctgcgct cggcccttcc ggctggctgg tttattgctg 2460
ataaatctgg agccggtgag cgtgggtctc gcggtatcat tgcagcactg gggccagatg 2520
gtaagccctc ccgtatcgta gttatctaca cgacggggag tcaggcaact atggatgaac 2580
gaaatagaca gatcgctgag ataggtgcct cactgattaa gcattggtaa ctgtcagacc 2640
aagtttactc atatatactt tagattgatt taaaacttca tttttaattt aaaaggatct 2700
aggtgaagat cctttttgat aatctcatga ccaaaatccc ttaacgtgag ttttcgttcc 2760
actgagcgtc agaccccgta gaaaagatca aaggatcttc ttgagatcct ttttttctgc 2820
gcgtaatctg ctgcttgcaa acaaaaaaac caccgctacc agcggtggtt tgtttgccgg 2880
atcaagagct accaactctt tttccgaagg taactggctt cagcagagcg cagataccaa 2940
atactgtcct tctagtgtag ccgtagttag gccaccactt caagaactct gtagcaccgc 3000
ctacatacct cgctctgcta atcctgttac cagtggctgc tgccagtggc gataagtcgt 3060

```
gtcttaccgg gttggactca agacgatagt taccggataa ggcgcagcgg tcgggctgaa   3120
cgggggggttc gtgcacacag cccagcttgg agcgaacgac ctacaccgaa ctgagatacc   3180
tacagcgtga gctatgagaa agcgccacgc ttcccgaagg gagaaaggcg gacaggtatc   3240
cggtaagcgg cagggtcgga acaggagagc gcacgaggga gcttccaggg ggaaacgcct   3300
ggtatcttta tagtcctgtc gggtttcgcc acctctgact tgagcgtcga tttttgtgat   3360
gctcgtcagg ggggcggagc ctatggaaaa acgccagcaa cgcggccttt ttacggttcc   3420
tggccttttg ctggcctttt gctcacatgt tctttcctgc gttatcccct gattctgtgg   3480
ataaccgtat taccgccttt gagtgagctg ataccgctcg ccgcagccga acgaccgagc   3540
gcagcgagtc agtgagcgag gaagcggaag agcgcctgat gcggtatttt ctccttacgc   3600
atctgtgcgg tatttcacac cgcatatatg gtgcactctc agtacaatct gctctgatgc   3660
cgcatagtta agccagtata cactccgcta tcgctacgtg actgggtcat ggctgcgccc   3720
cgacacccgc caacacccgc tgacgcgccc tgacgggctt gtctgctccc ggcatccgct   3780
tacagacaag ctgtgaccgt ctccgggagc tgcatgtgtc agaggttttc accgtcatca   3840
ccgaaacgcg cgaggcagct gcggtaaagc tcatcagcgt ggtcgtgaag cgattcacag   3900
atgtctgcct gttcatccgc gtccagctcg ttgagtttct ccagaagcgt taatgtctgg   3960
cttctgataa agcgggccat gttaagggcg gttttttcct gtttggtcac tgatgcctcc   4020
gtgtaagggg gatttctgtt catgggggta atgataccga tgaaacgaga gaggatgctc   4080
acgatacggg ttactgatga tgaacatgcc cggttactgg aacgttgtga gggtaaacaa   4140
ctggcggtat ggatgcggcg ggaccagaga aaaatcactc agggtcaatg ccagcgcttc   4200
gttaatacag atgtaggtgt tccacagggt agccagcagc atcctgcgat gcagatccgg   4260
aacataatgg tgcagggcgc tgacttccgc gtttccagac tttacgaaac acggaaaccg   4320
aagaccattc atgttgttgc tcaggtcgca gacgttttgc agcagcagtc gcttcacgtt   4380
cgctcgcgta tcggtgattc attctgctaa ccagtaaggc aaccccgcca gcctagccgg   4440
gtcctcaacg acaggagcac gatcatgcgc acccgtggcc aggacccaac gctgcccgag   4500
atgcgccgcg tgcggctgct ggagatggcg gacgcgatgg atatgttctg ccaagggttg   4560
gtttgcgcat tcacagttct ccgcaagaat tgattggctc caattcttgg agtggtgaat   4620
ccgttagcga ggtgccgccg gcttccattc aggtcgaggt ggcccggctc catgcaccgc   4680
gacgcaacgc ggggaggcag acaaggtata gggcggcgcc tacaatccat gccaacccgt   4740
tccatgtgct cgccgaggcg gcataaatcg ccgtgacgat cagcggtcca atgatcgaag   4800
ttaggctggt aagagccgcg agcgatcctt gaagctgtcc ctgatggtcg tcatctacct   4860
gcctggacag catggcctgc aacgcgggca tcccgatgcc gccggaagcg agaagaatca   4920
taatggggaa ggccatccag cctcgcgtcg cgaacgccag caagacgtag cccagcgcgt   4980
cggccgccat gccggcgata atggcctgct tctcgccgaa acgtttggtg gcgggaccag   5040
tgacgaaggc ttgagcgagg gcgtgcaaga ttccgaatac cgcaagcgac aggccgatca   5100
tcgtcgcgct ccagcgaaag cggtcctcgc cgaaaatgac ccagagcgct gccggcacct   5160
gtcctacgag ttgcatgata aagaagacag tcataagtgc ggcgacgata gtcatgcccc   5220
gcgcccaccg gaaggagctg actgggttga aggctctcaa gggcatcggt cgacgctctc   5280
ccttatgcga ctcctgcatt aggaagcagc ccagtagtag gttgaggccg ttgagcaccg   5340
ccgccgcaag gaatggtgca tgcat                                          5365
```

<210> SEQ ID NO 28
<211> LENGTH: 1062
<212> TYPE: DNA
<213> ORGANISM: Artificial sequence
<220> FEATURE:
<223> OTHER INFORMATION: codon modified sequence

<400> SEQUENCE: 28

```
atgaaaaact atccgaccat gaaagtggcg gcggtgcagg cggggccggt cttcctgaac     60
ctggaagcga ccctggaaaa aacatgcaag ctgattgcgg aggccgcatc aatgggtgcg    120
aaggtgattg gctttccgga agcctttatt ccgggttatc cttattggat ttggaccacc    180
aatatggagt ttactggcat gatgtgggcg gtgctcttta aacaggcagt cgaagttccg    240
tcgaaagaag ttcaacagat taccgatgcc gccaaaaaaa acggcatcta cgtctgcgtg    300
tcgatcagtg aacgtgataa cgccagtatt tatcttaccc agctgtggtt tgatccgaat    360
ggtaatgttc tgggcaaaca ccgcaaattt aaaccaacgt ccacggaacg tgcgatttgg    420
ggtgatggcg atgggtctat ggcaccggtt tttcggaccg aatacggtaa cctgggtggc    480
ctgcagtgtt gggaacatgc gctgccgctg aacctggccg cgatgggtac gttaaacgaa    540
caggtgcacg tcgcctcttg gccggccttc gtgccaaagg gcgccgttag ttccaaagtt    600
agctccagcg tgtgcgcgag caccaatgca atgcatcaat tgatctccca gttctatgcg    660
atctctaacc aagtttatgt gattatgagc acgaacttgt tgggtcagga catgattgat    720
ctgctgggca aagaagaatt ctcgaaaaat tatttgccgc ttggcacggg gaacaccgca    780
atcatcagca actctggcga agtgttagcg agcattcctc aggatggcga gggcattgct    840
gtggcggaga ttgacctgaa tcagatcatt tatgcgaaat ggctgattga tccggccggc    900
cattacagta ccccaggttt tctgtcgctg acttttgaca acagcgaaca tgtgcccgtg    960
aaaaaaattg gcgaacagac gaaccatttt attagctatg aagatttaca tgaagataaa   1020
atggatatgt taaccatccc gccgcgccgc gtagcgaccg cg                      1062
```

<210> SEQ ID NO 29
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 29

```
Met Lys Asn Tyr Pro Thr Met Lys Val Ala Ala Val Gln Ala Gly Pro
1               5                   10                  15

Val Phe Leu Asn Leu Glu Ala Thr Leu Glu Lys Thr Cys Lys Leu Ile
            20                  25                  30

Ala Glu Ala Ala Ser Met Gly Ala Lys Val Ile Gly Phe Pro Glu Ala
        35                  40                  45

Phe Ile Pro Gly Tyr Pro Tyr Trp Ile Trp Thr Thr Asn Met Glu Phe
    50                  55                  60

Thr Gly Met Met Trp Ala Val Leu Phe Lys Gln Ala Val Glu Val Pro
65                  70                  75                  80

Ser Lys Glu Val Gln Gln Ile Thr Asp Ala Ala Lys Lys Asn Gly Ile
                85                  90                  95

Tyr Val Cys Val Ser Ile Ser Glu Arg Asp Asn Ala Ser Ile Tyr Leu
            100                 105                 110

Thr Gln Leu Trp Phe Asp Pro Asn Gly Asn Val Leu Gly Lys His Arg
        115                 120                 125
```

```
Lys Phe Lys Pro Thr Ser Thr Glu Arg Ala Ile Trp Gly Asp Gly Asp
    130                 135                 140

Gly Ser Met Ala Pro Val Phe Arg Thr Glu Tyr Gly Asn Leu Gly Gly
145                 150                 155                 160

Leu Gln Cys Trp Glu His Ala Leu Pro Leu Asn Leu Ala Ala Met Gly
                165                 170                 175

Thr Leu Asn Glu Gln Val His Val Ala Ser Trp Pro Ala Phe Val Pro
            180                 185                 190

Lys Gly Ala Val Ser Ser Lys Val Ser Ser Ser Val Cys Ala Ser Thr
        195                 200                 205

Asn Ala Met His Gln Leu Ile Ser Gln Phe Tyr Ala Ile Ser Asn Gln
    210                 215                 220

Val Tyr Val Ile Met Ser Thr Asn Leu Leu Gly Gln Asp Met Ile Asp
225                 230                 235                 240

Leu Leu Gly Lys Glu Glu Phe Ser Lys Asn Tyr Leu Pro Leu Gly Thr
                245                 250                 255

Gly Asn Thr Ala Ile Ile Ser Asn Ser Gly Glu Val Leu Ala Ser Ile
            260                 265                 270

Pro Gln Asp Gly Glu Gly Ile Ala Val Ala Glu Ile Asp Leu Asn Gln
        275                 280                 285

Ile Ile Tyr Ala Lys Trp Leu Ile Asp Pro Ala Gly His Tyr Ser Thr
    290                 295                 300

Pro Gly Phe Leu Ser Leu Thr Phe Asp Asn Ser Glu His Val Pro Val
305                 310                 315                 320

Lys Lys Ile Gly Glu Gln Thr Asn His Phe Ile Ser Tyr Glu Asp Leu
                325                 330                 335

His Glu Asp Lys Met Asp Met Leu Thr Ile Pro Pro Arg Arg Val Ala
            340                 345                 350

Thr Ala


<210> SEQ ID NO 30
<211> LENGTH: 1062
<212> TYPE: DNA
<213> ORGANISM: Artificial sequence
<220> FEATURE:
<223> OTHER INFORMATION: codon modified sequence

<400> SEQUENCE: 30

atgaaaaact atccgactat taaagtggcc gcggtgcaag cgggcccgat cttcatgaac      60

ctggatggta ccctggataa aacgtgcaaa attattgcag aagccgcgtc catgggcgcc     120

aaagtaatcg gctttccaga ggcgtttatc ccgggctatc cgtactggat ttggaccacg     180

aacattgatt atacgggcat gttgtacgcg gtgctgtgga aaaacgcgct ggaaattccg     240

agtaaggagg ttcagcagat ctctgaagcg gcgcgtaaaa acggcgtttg ggtctgcatg     300

agcatgtctg aaaaagaaaa tggtagcctg tatctgactc agatctggtt cgaccctcaa     360

ggtaatatta ttggcaaaca tcgcaaattt cgtccgacca ccaccgaacg cggtctgtgg     420

ggggatggcg acggcagcat ggccccggtg tataaaacgg aatatggtaa cctgggcgca     480

ctgcagtgct gggaacatgc cctgccactg aatttggcgg cgatggctag cctgaatgaa     540

caggtgcatg ttgcgtcctg gccggcctac gtgccgcgcg gcggcgtctc ttcgcgctta     600

agtagttcgg tgtgtggtac caccaacgct atgcaccaaa ttatttcgca gttttatgca     660

ctgagcaacc aggtgtatgt gatcatgagc accaacctct tgggccagga tatcgtcgat     720
```

```
atggttggga aagatgaatt cacccgtcag tttgtgccgg tgggctccgg taacaccgcg    780

attattagca atacgggaga attattagca tcgattccgc aggatgcgga aggtattgcc    840

gtggccgaaa tcgatatgca gcagattctt tacggcaaat ggcttttgga tccggggggt    900

cattatagta cacccggctt tttatccctg acctttgacc agtctgaaca cgttccagtg    960

aagaaaattg gtgaacaaac caaccatttt atcagctatg aagatctgca tgaggataaa   1020

atggacatgc tgaccattcc gcctcgccgt gttgcgacgg cg                      1062


<210> SEQ ID NO 31
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 31

Met Lys Asn Tyr Pro Thr Ile Lys Val Ala Ala Val Gln Ala Gly Pro
1               5                   10                  15

Ile Phe Met Asn Leu Asp Gly Thr Leu Asp Lys Thr Cys Lys Ile Ile
            20                  25                  30

Ala Glu Ala Ala Ser Met Gly Ala Lys Val Ile Gly Phe Pro Glu Ala
        35                  40                  45

Phe Ile Pro Gly Tyr Pro Tyr Trp Ile Trp Thr Thr Asn Ile Asp Tyr
    50                  55                  60

Thr Gly Met Leu Tyr Ala Val Leu Trp Lys Asn Ala Leu Glu Ile Pro
65                  70                  75                  80

Ser Lys Glu Val Gln Gln Ile Ser Glu Ala Ala Arg Lys Asn Gly Val
                85                  90                  95

Trp Val Cys Met Ser Met Ser Glu Lys Glu Asn Gly Ser Leu Tyr Leu
            100                 105                 110

Thr Gln Ile Trp Phe Asp Pro Gln Gly Asn Ile Ile Gly Lys His Arg
        115                 120                 125

Lys Phe Arg Pro Thr Thr Thr Glu Arg Gly Leu Trp Gly Asp Gly Asp
    130                 135                 140

Gly Ser Met Ala Pro Val Tyr Lys Thr Glu Tyr Gly Asn Leu Gly Ala
145                 150                 155                 160

Leu Gln Cys Trp Glu His Ala Leu Pro Leu Asn Leu Ala Ala Met Ala
                165                 170                 175

Ser Leu Asn Glu Gln Val His Val Ala Ser Trp Pro Ala Tyr Val Pro
            180                 185                 190

Arg Gly Gly Val Ser Ser Arg Leu Ser Ser Ser Val Cys Gly Thr Thr
        195                 200                 205

Asn Ala Met His Gln Ile Ile Ser Gln Phe Tyr Ala Leu Ser Asn Gln
    210                 215                 220

Val Tyr Val Ile Met Ser Thr Asn Leu Leu Gly Gln Asp Ile Val Asp
225                 230                 235                 240

Met Val Gly Lys Asp Glu Phe Thr Arg Gln Phe Val Pro Val Gly Ser
                245                 250                 255

Gly Asn Thr Ala Ile Ile Ser Asn Thr Gly Glu Leu Leu Ala Ser Ile
            260                 265                 270

Pro Gln Asp Ala Glu Gly Ile Ala Val Ala Glu Ile Asp Met Gln Gln
        275                 280                 285

Ile Leu Tyr Gly Lys Trp Leu Leu Asp Pro Gly Gly His Tyr Ser Thr
    290                 295                 300
```

Pro Gly Phe Leu Ser Leu Thr Phe Asp Gln Ser Glu His Val Pro Val
305 310 315 320

Lys Lys Ile Gly Glu Gln Thr Asn His Phe Ile Ser Tyr Glu Asp Leu
325 330 335

His Glu Asp Lys Met Asp Met Leu Thr Ile Pro Pro Arg Arg Val Ala
340 345 350

Thr Ala

<210> SEQ ID NO 32
<211> LENGTH: 1062
<212> TYPE: DNA
<213> ORGANISM: Artificial sequence
<220> FEATURE:
<223> OTHER INFORMATION: codon modified sequence

<400> SEQUENCE: 32
atgaaaaact atccgaccat taaagttgct gcggttcagg ccgcgccagt tttctgaac 60 ctggatgcca ccgtggataa aacgtgccgc ctgattgcgg aagccgcgag catgggtgcg 120
aaggtgatcg gctttccgga agccttttta ccgggttatc cttactggat ctttaccacc 180
aatcttgatt atacggcgat tatttgggcg attctgttcc gcaatgcgat cgacgtgcca 240
tcacgtgaaa tgcagcagat tagcgaggct gcgaaacgta atggcctgta cgtatgtatt 300
tccctgtcag aacgcgaaaa cgcgacctta taccttaccc aggtgttttt tgatcccaac 360
ggcaacttga tcggccgcca tcgtaaattc aaaccgacca gttcggaaaa agcgatttgg 420
ggcgatggtg atggtacgat ggcaccggtc tttaaaaccg atttcggtaa tttaggggcg 480
ttacaatgct gggaacatgc cctgccgctg aacatcgcgg cgatgggtac cttgaacgag 540
caggtgcatg tggccagctg gcctgcattt gttccgaaag gtggtgtttc tactaaaatg 600
tctagctccg tgtgcggcag cacaaacgcc atgcatcagc tgatgaccca gttttatgcc 660
ctcagcaacc agatttatgt gattgtgtcg accaacctgg ttggccagga gctgatggaa 720
ctgctgggca aagatgactt ttcgaagaac tatattccga ttgggagtgg caacaccgca 780
attatcagca atactggcga cattctcggc accattccgc aggaagcgga agggttggcg 840
attgcagaaa ttgatctgca gcaaatcatc tatgcgaaat ggattatgga tccagccggc 900
cattatagta cgccgggttt tctgtctctg accttcgata acacggaaca tgtgccggtc 960
cgtaaagtcg gcgaacaaac gaatcacttt atctcctatg aagatctgca cgaagacaaa 1020
atggatatgt tgactatccc gccgcgccgg gtggccacgg ca 1062

<210> SEQ ID NO 33
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 33

Met Lys Asn Tyr Pro Thr Ile Lys Val Ala Ala Val Gln Ala Ala Pro
1 5 10 15

Val Phe Leu Asn Leu Asp Ala Thr Val Asp Lys Thr Cys Arg Leu Ile
20 25 30

Ala Glu Ala Ala Ser Met Gly Ala Lys Val Ile Gly Phe Pro Glu Ala
35 40 45

Phe Leu Pro Gly Tyr Pro Tyr Trp Ile Phe Thr Thr Asn Leu Asp Tyr
50 55 60

```
Thr Ala Ile Ile Trp Ala Ile Leu Phe Arg Asn Ala Ile Asp Val Pro
65                  70                  75                  80

Ser Arg Glu Met Gln Gln Ile Ser Glu Ala Ala Lys Arg Asn Gly Leu
                85                  90                  95

Tyr Val Cys Ile Ser Leu Ser Glu Arg Glu Asn Ala Thr Leu Tyr Leu
            100                 105                 110

Thr Gln Val Phe Phe Asp Pro Asn Gly Asn Leu Ile Gly Arg His Arg
        115                 120                 125

Lys Phe Lys Pro Thr Ser Ser Glu Lys Ala Ile Trp Gly Asp Gly Asp
    130                 135                 140

Gly Thr Met Ala Pro Val Phe Lys Thr Asp Phe Gly Asn Leu Gly Ala
145                 150                 155                 160

Leu Gln Cys Trp Glu His Ala Leu Pro Leu Asn Ile Ala Ala Met Gly
                165                 170                 175

Thr Leu Asn Glu Gln Val His Val Ala Ser Trp Pro Ala Phe Val Pro
            180                 185                 190

Lys Gly Gly Val Ser Thr Lys Met Ser Ser Ser Val Cys Gly Ser Thr
        195                 200                 205

Asn Ala Met His Gln Leu Met Thr Gln Phe Tyr Ala Leu Ser Asn Gln
    210                 215                 220

Ile Tyr Val Ile Val Ser Thr Asn Leu Val Gly Gln Glu Leu Met Glu
225                 230                 235                 240

Leu Leu Gly Lys Asp Asp Phe Ser Lys Asn Tyr Ile Pro Ile Gly Ser
                245                 250                 255

Gly Asn Thr Ala Ile Ile Ser Asn Thr Gly Asp Ile Leu Gly Thr Ile
            260                 265                 270

Pro Gln Glu Ala Glu Gly Leu Ala Ile Ala Glu Ile Asp Leu Gln Gln
        275                 280                 285

Ile Ile Tyr Ala Lys Trp Ile Met Asp Pro Ala Gly His Tyr Ser Thr
    290                 295                 300

Pro Gly Phe Leu Ser Leu Thr Phe Asp Asn Thr Glu His Val Pro Val
305                 310                 315                 320

Arg Lys Val Gly Glu Gln Thr Asn His Phe Ile Ser Tyr Glu Asp Leu
                325                 330                 335

His Glu Asp Lys Met Asp Met Leu Thr Ile Pro Pro Arg Arg Val Ala
            340                 345                 350

Thr Ala
```

<210> SEQ ID NO 34
<211> LENGTH: 990
<212> TYPE: DNA
<213> ORGANISM: Artificial sequence
<220> FEATURE:
<223> OTHER INFORMATION: codon modified sequence

<400> SEQUENCE: 34

```
atgaaagtgg tgaaagctgc ggcggtgcaa ctgagcccag tgatttattc ccgcgaagcg     60

accgtggaca aggtcctgaa aaaaatccat gacctggcgc agttgggcgt gcagtttgcg    120

acattcccgg agaccgtgct gccgtactat ccttatttct ccgcggttca aactggggtg    180

gaactgctga gcggtacgga acatatccgc ttaattgata atgcggtaac cgttccgagt    240

ccggccaccg atgcaattgg cgatgccgcg aagaaagctg gtatggtggt tagtatcggt    300

attaacgaac gtgatggcgg taccctgtat aatacccaga ttctgtttga tgcggatggc    360

accctgttga accgccgccg caaaatcacc ccgacgcatt atgaacgtat gatctggggc    420
```

```
cagggcgatg gctcagccct gcgtgcggtt gatagcaaag tcggtcgcat tgggcaactg    480

gcctgttttg aacacaacaa cccgttagcg cgctacgcac tgattgcgga tggtgaacag    540

attcattctg ccatgtatcc gggtagcgcg tacggtgatg cgtttgccca gcggatggag    600

atcaatattc gtaaccatgc aatcgagtct ggggcatttg tggtgaacgc aaccgcgtgg    660

ctggatgccg atcagcaggc gcagttagtt aaagatacgg gctgcggcat tgcgccaatt    720

tcgggcggtt gctttaccac cattgttgca ccggacggca tgattatggc cgaaccattg    780

cgtagcgcgg aaggcgaagt cattgtggac ttggatttta ctcttattga caaacgcaaa    840

atgttaatgg attcggccgg ccactataac cgtccggaac tgctcagcct gcttatcgat    900

cgcacggcca ccgcgcatgt gcatgaacgg gcgggccacc cgctgagcgg cgcggaacag    960

ggtccggaag atctgcgtac gcctgccgcc                                     990
```

<210> SEQ ID NO 35
<211> LENGTH: 330
<212> TYPE: PRT
<213> ORGANISM: Artificial sequence
<220> FEATURE:
<223> OTHER INFORMATION: translated protein from codon modified sequence

<400> SEQUENCE: 35

```
Met Lys Val Val Lys Ala Ala Ala Val Gln Leu Ser Pro Val Ile Tyr
1               5                   10                  15

Ser Arg Glu Ala Thr Val Asp Lys Val Leu Lys Lys Ile His Asp Leu
            20                  25                  30

Ala Gln Leu Gly Val Gln Phe Ala Thr Phe Pro Glu Thr Val Leu Pro
        35                  40                  45

Tyr Tyr Pro Tyr Phe Ser Ala Val Gln Thr Gly Val Glu Leu Leu Ser
    50                  55                  60

Gly Thr Glu His Ile Arg Leu Ile Asp Asn Ala Val Thr Val Pro Ser
65                  70                  75                  80

Pro Ala Thr Asp Ala Ile Gly Asp Ala Ala Lys Lys Ala Gly Met Val
                85                  90                  95

Val Ser Ile Gly Ile Asn Glu Arg Asp Gly Gly Thr Leu Tyr Asn Thr
            100                 105                 110

Gln Ile Leu Phe Asp Ala Asp Gly Thr Leu Leu Asn Arg Arg Arg Lys
        115                 120                 125

Ile Thr Pro Thr His Tyr Glu Arg Met Ile Trp Gly Gln Gly Asp Gly
    130                 135                 140

Ser Ala Leu Arg Ala Val Asp Ser Lys Val Gly Arg Ile Gly Gln Leu
145                 150                 155                 160

Ala Cys Phe Glu His Asn Asn Pro Leu Ala Arg Tyr Ala Leu Ile Ala
                165                 170                 175

Asp Gly Glu Gln Ile His Ser Ala Met Tyr Pro Gly Ser Ala Tyr Gly
            180                 185                 190

Asp Ala Phe Ala Gln Arg Met Glu Ile Asn Ile Arg Asn His Ala Ile
        195                 200                 205

Glu Ser Gly Ala Phe Val Val Asn Ala Thr Ala Trp Leu Asp Ala Asp
    210                 215                 220

Gln Gln Ala Gln Leu Val Lys Asp Thr Gly Cys Gly Ile Ala Pro Ile
225                 230                 235                 240

Ser Gly Gly Cys Phe Thr Thr Ile Val Ala Pro Asp Gly Met Ile Met
                245                 250                 255
```

```
Ala Glu Pro Leu Arg Ser Ala Glu Gly Glu Val Ile Val Asp Leu Asp
            260                 265                 270

Phe Thr Leu Ile Asp Lys Arg Lys Met Leu Met Asp Ser Ala Gly His
        275                 280                 285

Tyr Asn Arg Pro Glu Leu Leu Ser Leu Leu Ile Asp Arg Thr Ala Thr
    290                 295                 300

Ala His Val His Glu Arg Ala Gly His Pro Leu Ser Gly Ala Glu Gln
305                 310                 315                 320

Gly Pro Glu Asp Leu Arg Thr Pro Ala Ala
                325                 330


<210> SEQ ID NO 36
<211> LENGTH: 990
<212> TYPE: DNA
<213> ORGANISM: Artificial sequence
<220> FEATURE:
<223> OTHER INFORMATION: codon modified sequence

<400> SEQUENCE: 36

atgaaaattg tgaaagcggc ggccgttcag ctgagcccgg ttttatttag taaagatgcg      60

accctggata aaatcatcaa aaaaattcat gaattaggcc agctgggtgt tcagtttgcc     120

acctttccgg aaaccgtggt gccgtattat ccttactttt ctgcggttca gacgggcgtg     180

gaactgattt ccggcagtga acatatgcgg attctggaga atgcgattac ggtgccgagc     240

ccggcaacgg atgcaatcgg tgaagctgcg aaaaaggcgg gcatggtggt gagcgtgggc     300

gtgaatgaaa aagatgcggg cactctttat aacacccagg tattatttga tgccgacggt     360

accttactgc agcgtcgtcg caaactgacc ccaacgcact ttgaacgcat ggtttggggc     420

cagggggatg gttccggcat tcgcgcggtt gagacaaaag tcgggcgtat cggccaggtg     480

gcgtgcttcg aacataacaa cccactggcg cgctatgccc tgattgcgga tggcgaacaa     540

atccatagcg cggtgtatcc gggctcggcc tttggtgaag gcttcgcgca gaaagtggaa     600

ctgaacctgc gtcagcatgc gattgagagc ggcgcatttg tcgtcaacgc gaccgcctgg     660

ctggatgcag aacagcaagc gcagattatt aaagatacgg gttgcggtat tggcccgctg     720

agcgggggct gttttaccac cattgtggcc ccagatggca tggtgatggc tgatcctttg     780

cgttcaggtg aaggtgaagt gatcgtcgat ttggacttca cgcttattga caaacgcaag     840

atgatgatgg ataccggtgg tcactacaac cgtccggagt tgttgtctct gatcctcgat     900

cgcaccggca ccgcccacgt tcatgaacgc ggcggtcatc cgctgtcggc agccgaacaa     960

ggaccggaag acctgcgcac tccggcggcc                                      990


<210> SEQ ID NO 37
<211> LENGTH: 330
<212> TYPE: PRT
<213> ORGANISM: Artificial sequence
<220> FEATURE:
<223> OTHER INFORMATION: translated protein from codon modified sequence

<400> SEQUENCE: 37

Met Lys Ile Val Lys Ala Ala Ala Val Gln Leu Ser Pro Val Leu Phe
1               5                   10                  15

Ser Lys Asp Ala Thr Leu Asp Lys Ile Ile Lys Lys Ile His Glu Leu
            20                  25                  30

Gly Gln Leu Gly Val Gln Phe Ala Thr Phe Pro Glu Thr Val Val Pro
        35                  40                  45

Tyr Tyr Pro Tyr Phe Ser Ala Val Gln Thr Gly Val Glu Leu Ile Ser
```

```
    50                  55                  60

Gly Ser Glu His Met Arg Ile Leu Glu Asn Ala Ile Thr Val Pro Ser
65                  70                  75                  80

Pro Ala Thr Asp Ala Ile Gly Glu Ala Ala Lys Lys Ala Gly Met Val
                85                  90                  95

Val Ser Val Gly Val Asn Glu Lys Asp Ala Gly Thr Leu Tyr Asn Thr
            100                 105                 110

Gln Val Leu Phe Asp Ala Asp Gly Thr Leu Leu Gln Arg Arg Arg Lys
        115                 120                 125

Leu Thr Pro Thr His Phe Glu Arg Met Val Trp Gly Gln Gly Asp Gly
    130                 135                 140

Ser Gly Ile Arg Ala Val Glu Thr Lys Val Gly Arg Ile Gly Gln Val
145                 150                 155                 160

Ala Cys Phe Glu His Asn Asn Pro Leu Ala Arg Tyr Ala Leu Ile Ala
                165                 170                 175

Asp Gly Glu Gln Ile His Ser Ala Val Tyr Pro Gly Ser Ala Phe Gly
            180                 185                 190

Glu Gly Phe Ala Gln Lys Val Glu Leu Asn Leu Arg Gln His Ala Ile
        195                 200                 205

Glu Ser Gly Ala Phe Val Val Asn Ala Thr Ala Trp Leu Asp Ala Glu
    210                 215                 220

Gln Gln Ala Gln Ile Ile Lys Asp Thr Gly Cys Gly Ile Gly Pro Leu
225                 230                 235                 240

Ser Gly Gly Cys Phe Thr Thr Ile Val Ala Pro Asp Gly Met Val Met
                245                 250                 255

Ala Asp Pro Leu Arg Ser Gly Glu Gly Glu Val Ile Val Asp Leu Asp
            260                 265                 270

Phe Thr Leu Ile Asp Lys Arg Lys Met Met Met Asp Thr Gly Gly His
        275                 280                 285

Tyr Asn Arg Pro Glu Leu Leu Ser Leu Ile Leu Asp Arg Thr Gly Thr
    290                 295                 300

Ala His Val His Glu Arg Gly Gly His Pro Leu Ser Ala Ala Glu Gln
305                 310                 315                 320

Gly Pro Glu Asp Leu Arg Thr Pro Ala Ala
                325                 330


<210> SEQ ID NO 38
<211> LENGTH: 990
<212> TYPE: DNA
<213> ORGANISM: Artificial sequence
<220> FEATURE:
<223> OTHER INFORMATION: codon modified sequence

<400> SEQUENCE: 38

atgcgcatgg ttaaagcggc agcggttcag gtctcgcctg tgctgtttag ccgcgatggt      60

acgattgaaa aagtcgtgaa acgcattcat gagctggctc agttaggcgt gcagtttgcg     120

actttcccag agaccattct gccgtattat ccgtattttt ctggcctgca aaccggtatc     180

gaactggtta gtgcgaccga tcatctgaaa atgctggaca acgccctgac gttaccgtcg     240

ccggcgacag atgcaattgc cgaagccgcg cgcaaagcag gtgtggttgt tagcttaggg     300

gtgaacgaac gtgacgccgg caccatgtat aatacccagg tcctttttga tgcggatggt     360

acgctggttc agcgccgtcg taaaattact ccgacccatt atgaacgctt gatttggggt     420

caaggtgatg gcagcggtct gaaagccgta gaaagccgtc tggggcgtat cggccagctg     480
```

-continued

```
gcatgctttg aacataataa cccgttagcc cgttacgcgc tgattgctga tggcgaacag    540

attcattctg cgatctaccc ggcgagtgcg tatgcggaag ggtttgcgca acggatggat    600

ctgaacattc gccagcatgc cctggaaagc ggcgcgtttg tggtgaacgc aacggcctac    660

ctcgaagccg accagcaggc caatgtcatt aaagaaaccg cctgcggtat cgcgccaatg    720

tccggcgcgt gtttcaccac gattgtggcg ccagagggcg tgatcatggg cgaaccgctt    780

aaaagcggcg aaggcgaagt tgtggtggat ctcgattatt ccgtgatcga taaacgcaag    840

atgatgttgg atagtgcagg ccactataac cgtccggaat tgctgtccct gatggtggaa    900

cgcaccgcaa ccgcgcacgt gcacgaacgt gccgcccatc cgttgtcggc ggcggaacag    960

ggtcctgaag agctgcgcac cccggcggcg                                     990
```

<210> SEQ ID NO 39
<211> LENGTH: 330
<212> TYPE: PRT
<213> ORGANISM: Artificial sequence
<220> FEATURE:
<223> OTHER INFORMATION: translated protein from codon modified sequence

<400> SEQUENCE: 39

```
Met Arg Met Val Lys Ala Ala Ala Val Gln Val Ser Pro Val Leu Phe
1               5                   10                  15

Ser Arg Asp Gly Thr Ile Glu Lys Val Val Lys Arg Ile His Glu Leu
            20                  25                  30

Ala Gln Leu Gly Val Gln Phe Ala Thr Phe Pro Glu Thr Ile Leu Pro
        35                  40                  45

Tyr Tyr Pro Tyr Phe Ser Gly Leu Gln Thr Gly Ile Glu Leu Val Ser
    50                  55                  60

Ala Thr Asp His Leu Lys Met Leu Asp Asn Ala Leu Thr Leu Pro Ser
65                  70                  75                  80

Pro Ala Thr Asp Ala Ile Ala Glu Ala Ala Arg Lys Ala Gly Val Val
                85                  90                  95

Val Ser Leu Gly Val Asn Glu Arg Asp Ala Gly Thr Met Tyr Asn Thr
            100                 105                 110

Gln Val Leu Phe Asp Ala Asp Gly Thr Leu Val Gln Arg Arg Arg Lys
        115                 120                 125

Ile Thr Pro Thr His Tyr Glu Arg Leu Ile Trp Gly Gln Gly Asp Gly
    130                 135                 140

Ser Gly Leu Lys Ala Val Glu Ser Arg Leu Gly Arg Ile Gly Gln Leu
145                 150                 155                 160

Ala Cys Phe Glu His Asn Asn Pro Leu Ala Arg Tyr Ala Leu Ile Ala
                165                 170                 175

Asp Gly Glu Gln Ile His Ser Ala Ile Tyr Pro Ala Ser Ala Tyr Ala
            180                 185                 190

Glu Gly Phe Ala Gln Arg Met Asp Leu Asn Ile Arg Gln His Ala Leu
        195                 200                 205

Glu Ser Gly Ala Phe Val Val Asn Ala Thr Ala Tyr Leu Glu Ala Asp
    210                 215                 220

Gln Gln Ala Asn Val Ile Lys Glu Thr Ala Cys Gly Ile Ala Pro Met
225                 230                 235                 240

Ser Gly Ala Cys Phe Thr Thr Ile Val Ala Pro Glu Gly Val Ile Met
                245                 250                 255

Gly Glu Pro Leu Lys Ser Gly Glu Gly Glu Val Val Val Asp Leu Asp
            260                 265                 270
```

Tyr Ser Val Ile Asp Lys Arg Lys Met Met Leu Asp Ser Ala Gly His
275 280 285

Tyr Asn Arg Pro Glu Leu Leu Ser Leu Met Val Glu Arg Thr Ala Thr
290 295 300

Ala His Val His Glu Arg Ala Ala His Pro Leu Ser Ala Ala Glu Gln
305 310 315 320

Gly Pro Glu Glu Leu Arg Thr Pro Ala Ala
325 330

<210> SEQ ID NO 40
<211> LENGTH: 1041
<212> TYPE: DNA
<213> ORGANISM: Artificial sequence
<220> FEATURE:
<223> OTHER INFORMATION: codon modified sequence

<400> SEQUENCE: 40
atggaaaaaa gcaaaaccgt ccgcgcggcc gccgcgcaga ttgccccaga tctgacctct 60
cgcgataaca ccgtggcccg catcctcgat actattcacg aagcggcggg caaaggtgcc 120
gaactgattg tgtttccgga aacgttcctg ccttggtacc cgtatttttc ttttgtgctg 180
ccgccggtgg tgagtggtcg cgaacatctt cgtctgtttg aagaagcggt gaccgtgcca 240
tcgggcacga ccgatgcggt tgcgaccgcg gcgcgggatc atggcgtcgt tgtggcgctt 300
ggcgttaatg aacgcgatca tggtacggtt tataacaccc agttagtttt tgatgcggat 360
ggcggcctgg tgctgcgccg gcgcaaaatt accccgacgt ttcatgaacg tatgatctgg 420
gcgcagggcg acgcgagcgg gttgaaagtt gtggacaccc aggtcggccg tatcggtgca 480
gtggcctgtt gggagcattg gaaccccctg gctcgctacg cattaatggc gcagcacgaa 540
gatattcacg ttgcacaatt tccagcgtcc gtggtggggc ctatctatgg cgaacagatg 600
gaattaacca ttcgtcacca tgcgctggaa tcgggatgct tcgtagttaa tgctactggt 660
tggctgaccg aggaacagat ccgtagcatc accccggacg aacagatcca aaaagcctta 720
cgcggtggct gcatgacggc gattattagc ccggaggggc gtcatctggc cccgccgatt 780
tcagaaggtg aaggcattct cctggcagac ctggatttga gtctgattct gaagcgcaaa 840
cgtatgctgg attccgtggg tcattatgcg cgtccggaat tgctgcatct ggtcgtggat 900
cagcgtccag ccgtgaccat ggtcagcgcg catccgtttc tggagaccgc gccgacaggc 960
agcaacactg atggtcatca gacgagcgcc ttcgatggca acccggatca gcgtgccgca 1020
attttgcgcc gccaagcagg c 1041

<210> SEQ ID NO 41
<211> LENGTH: 347
<212> TYPE: PRT
<213> ORGANISM: Artificial sequence
<220> FEATURE:
<223> OTHER INFORMATION: translated protein from codon modified sequence

<400> SEQUENCE: 41

Met Glu Lys Ser Lys Thr Val Arg Ala Ala Ala Ala Gln Ile Ala Pro
1 5 10 15

Asp Leu Thr Ser Arg Asp Asn Thr Val Ala Arg Ile Leu Asp Thr Ile
20 25 30

His Glu Ala Ala Gly Lys Gly Ala Glu Leu Ile Val Phe Pro Glu Thr
35 40 45

Phe Leu Pro Trp Tyr Pro Tyr Phe Ser Phe Val Leu Pro Pro Val Val
50 55 60

```
Ser Gly Arg Glu His Leu Arg Leu Phe Glu Glu Ala Val Thr Val Pro
65                  70                  75                  80

Ser Gly Thr Thr Asp Ala Val Ala Thr Ala Ala Arg Asp His Gly Val
                85                  90                  95

Val Val Ala Leu Gly Val Asn Glu Arg Asp His Gly Thr Val Tyr Asn
            100                 105                 110

Thr Gln Leu Val Phe Asp Ala Asp Gly Gly Leu Val Leu Arg Arg Arg
        115                 120                 125

Lys Ile Thr Pro Thr Phe His Glu Arg Met Ile Trp Ala Gln Gly Asp
    130                 135                 140

Ala Ser Gly Leu Lys Val Val Asp Thr Gln Val Gly Arg Ile Gly Ala
145                 150                 155                 160

Val Ala Cys Trp Glu His Trp Asn Pro Leu Ala Arg Tyr Ala Leu Met
                165                 170                 175

Ala Gln His Glu Asp Ile His Val Ala Gln Phe Pro Ala Ser Val Val
            180                 185                 190

Gly Pro Ile Tyr Gly Glu Gln Met Glu Leu Thr Ile Arg His His Ala
        195                 200                 205

Leu Glu Ser Gly Cys Phe Val Val Asn Ala Thr Gly Trp Leu Thr Glu
    210                 215                 220

Glu Gln Ile Arg Ser Ile Thr Pro Asp Glu Gln Ile Gln Lys Ala Leu
225                 230                 235                 240

Arg Gly Gly Cys Met Thr Ala Ile Ile Ser Pro Glu Gly Arg His Leu
                245                 250                 255

Ala Pro Pro Ile Ser Glu Gly Glu Gly Ile Leu Leu Ala Asp Leu Asp
            260                 265                 270

Leu Ser Leu Ile Leu Lys Arg Lys Arg Met Leu Asp Ser Val Gly His
        275                 280                 285

Tyr Ala Arg Pro Glu Leu Leu His Leu Val Val Asp Gln Arg Pro Ala
    290                 295                 300

Val Thr Met Val Ser Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345
```

<210> SEQ ID NO 42
<211> LENGTH: 1041
<212> TYPE: DNA
<213> ORGANISM: Artificial sequence
<220> FEATURE:
<223> OTHER INFORMATION: codon modified sequence

<400> SEQUENCE: 42

```
atggaaaaga gcaaaacggt gcgtgcggca gcagcgcagg tcgcaccgga tctgacgtca      60

aaagaaaaca ctctggcacg cattattgaa accattcacg aagccgccgg caaaggcgcg     120

gaactgattg tgtttccaga aagctttgtt ccgtggtatc cgtactatag cttcgtcatg     180

ccaccagttc tcaccgggcg tgagcatctg aaactttatg atgacgcgct ctcgctccct     240

agcgcgacca ccgacgccgt ggccaccgcg gcccgcgaac acgggatctt ggtggcgctg     300

ggagtgaacg agcgtgaaca tggctctctg tataacactc agttagtctt tgatgcggat     360

ggcgcgctgg tgctgcgccg ccgtaaatta accccgactt ttcatgaacg catgatctgg     420
```

```
ggtcagggcg atggttctgg cctgaaagtg gtggaaaccc aggttggccg tattggtgcg    480

attgcctgct gggaacattg gaacccgctg gcgcgctatg cactgatggc ccaacatgaa    540

gaaattcatg tggcgaactt tccaggtagt atggttggcc ctatctttgc cgagcagatg    600

gaaatgtccg ttcggcatca cgcgattgag agcggttgtt tcgttgtgaa cgcgaccgcc    660

tggttaacgg acgaacaggt tcgtagcctg acgcccgaag atcagattca acgtggtctt    720

cgtggcgggt gcatgaccgc gatcattagt ccggaaggtc gccatctggc gccgccgatg    780

accgaaggcg aaggcatcct ggtcgccgat ctggatttga ccatgatctt gcgtcgcaaa    840

aaagtgctgg atagcgtggg ccattacgcg cgcccggaat tacttcatct gctggtggat    900

caacgcccgg cgattacgat tgtaaccgcc catccgtttt tggaaaccgc gccgaccggt    960

tccaatacag atggtcacca gacgtcggct ttcgatggca atccggacca gcgcgctgcg   1020

atcctgcggc gccaggcagg c                                              1041
```

<210> SEQ ID NO 43
<211> LENGTH: 347
<212> TYPE: PRT
<213> ORGANISM: Artificial sequence
<220> FEATURE:
<223> OTHER INFORMATION: translated protein from codon modified sequence

<400> SEQUENCE: 43

```
Met Glu Lys Ser Lys Thr Val Arg Ala Ala Ala Ala Gln Val Ala Pro
1               5                   10                  15

Asp Leu Thr Ser Lys Glu Asn Thr Leu Ala Arg Ile Ile Glu Thr Ile
            20                  25                  30

His Glu Ala Ala Gly Lys Gly Ala Glu Leu Ile Val Phe Pro Glu Ser
        35                  40                  45

Phe Val Pro Trp Tyr Pro Tyr Tyr Ser Phe Val Met Pro Pro Val Leu
    50                  55                  60

Thr Gly Arg Glu His Leu Lys Leu Tyr Asp Asp Ala Leu Ser Leu Pro
65                  70                  75                  80

Ser Ala Thr Thr Asp Ala Val Ala Thr Ala Ala Arg Glu His Gly Ile
                85                  90                  95

Leu Val Ala Leu Gly Val Asn Glu Arg Glu His Gly Ser Leu Tyr Asn
            100                 105                 110

Thr Gln Leu Val Phe Asp Ala Asp Gly Ala Leu Val Leu Arg Arg Arg
        115                 120                 125

Lys Leu Thr Pro Thr Phe His Glu Arg Met Ile Trp Gly Gln Gly Asp
    130                 135                 140

Gly Ser Gly Leu Lys Val Val Glu Thr Gln Val Gly Arg Ile Gly Ala
145                 150                 155                 160

Ile Ala Cys Trp Glu His Trp Asn Pro Leu Ala Arg Tyr Ala Leu Met
                165                 170                 175

Ala Gln His Glu Glu Ile His Val Ala Asn Phe Pro Gly Ser Met Val
            180                 185                 190

Gly Pro Ile Phe Ala Glu Gln Met Glu Met Ser Val Arg His His Ala
        195                 200                 205

Ile Glu Ser Gly Cys Phe Val Val Asn Ala Thr Ala Trp Leu Thr Asp
    210                 215                 220

Glu Gln Val Arg Ser Leu Thr Pro Glu Asp Gln Ile Gln Arg Gly Leu
225                 230                 235                 240

Arg Gly Gly Cys Met Thr Ala Ile Ile Ser Pro Glu Gly Arg His Leu
                245                 250                 255
```

```
Ala Pro Pro Met Thr Glu Gly Glu Gly Ile Leu Val Ala Asp Leu Asp
            260                 265                 270

Leu Thr Met Ile Leu Arg Arg Lys Lys Val Leu Asp Ser Val Gly His
        275                 280                 285

Tyr Ala Arg Pro Glu Leu Leu His Leu Leu Val Asp Gln Arg Pro Ala
    290                 295                 300

Ile Thr Ile Val Thr Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345


<210> SEQ ID NO 44
<211> LENGTH: 1041
<212> TYPE: DNA
<213> ORGANISM: Artificial sequence
<220> FEATURE:
<223> OTHER INFORMATION: codon modified sequence

<400> SEQUENCE: 44

atggataaaa gccgcagtgt gcgtgcggcg gccgcacagt tagcaccgga actttcctct     60

aaggaaaaca ccatgggcaa aatgattgat acgatccacg atgccgccgc gcgcggcgcg    120

gaactgattg tttttccgga aagcttcctg ccttggtacc cgtattggtc ttggattgtg    180

ccgccggtgg tctcgggccg cgaacatctg cgtctgtacg aggaagccat taccattccg    240

tcgggcacga ccgaagcggt ggccaccgca gccaaagaac atggcatctt ggtggcgctg    300

ggtgttaacg aaaaagacca tggaagtctg tataacaccc agatcgtgtt tgacgcagat    360

ggtgcgctgg tgttaaagcg ccgcaaaatc accccaacct ttcacgaacg tatgatttgg    420

ggccaaggcg atggtaccgg tattcgcgtt gtggatagcc agctgggccg tattggggcg    480

atggcctgtt gggaacattg gaatccactt gcccggtatg cgattatggc gcaacatgag    540

gatatccacg tggcgcagtt tccgggtagc gttgtgggcc cgatctgggg tgaacaggtc    600

gaaattaccg taaaacatca tgcaatcgag agcggttgct tcgttgtcaa tgccacgggt    660

tatttgtccg aagaccaaat tcgttccgtt acccccgatg ataacctgca gaaagctctg    720

cgtggcgggt gcatgactgc gattatttct cctgaaggtc gccatttagc gccgccactg    780

agcgaaggcg aaggcattct gatggccgat ttggatatga gtttgattgt gaaaaaaaaa    840

cgtctgatgg acaccctggg gcattatgcg cgcccggaag tgctgcatct gctcgttgaa    900

aaccgcccgg ccatcacggt cgtgacggcg cacccatttc tggagaccgc gccgacgggc    960

tcgaacactg atggccatca gacatcagcg tttgatggta atccggatca gcgcgcggca   1020

attttacggc gtcaggcggg c                                             1041


<210> SEQ ID NO 45
<211> LENGTH: 347
<212> TYPE: PRT
<213> ORGANISM: Artificial sequence
<220> FEATURE:
<223> OTHER INFORMATION: translated protein from codon modified sequence

<400> SEQUENCE: 45

Met Asp Lys Ser Arg Ser Val Arg Ala Ala Ala Ala Gln Leu Ala Pro
1               5                   10                  15

Glu Leu Ser Ser Lys Glu Asn Thr Met Gly Lys Met Ile Asp Thr Ile
```

```
            20                  25                  30

His Asp Ala Ala Ala Arg Gly Ala Glu Leu Ile Val Phe Pro Glu Ser
        35                  40                  45

Phe Leu Pro Trp Tyr Pro Tyr Trp Ser Trp Ile Val Pro Pro Val Val
    50                  55                  60

Ser Gly Arg Glu His Leu Arg Leu Tyr Glu Glu Ala Ile Thr Ile Pro
65                  70                  75                  80

Ser Gly Thr Thr Glu Ala Val Ala Thr Ala Ala Lys Glu His Gly Ile
                85                  90                  95

Leu Val Ala Leu Gly Val Asn Glu Lys Asp His Gly Ser Leu Tyr Asn
            100                 105                 110

Thr Gln Ile Val Phe Asp Ala Asp Gly Ala Leu Val Leu Lys Arg Arg
        115                 120                 125

Lys Ile Thr Pro Thr Phe His Glu Arg Met Ile Trp Gly Gln Gly Asp
    130                 135                 140

Gly Thr Gly Ile Arg Val Val Asp Ser Gln Leu Gly Arg Ile Gly Ala
145                 150                 155                 160

Met Ala Cys Trp Glu His Trp Asn Pro Leu Ala Arg Tyr Ala Ile Met
                165                 170                 175

Ala Gln His Glu Asp Ile His Val Ala Gln Phe Pro Gly Ser Val Val
            180                 185                 190

Gly Pro Ile Trp Gly Glu Gln Val Glu Ile Thr Val Lys His His Ala
        195                 200                 205

Ile Glu Ser Gly Cys Phe Val Val Asn Ala Thr Gly Tyr Leu Ser Glu
    210                 215                 220

Asp Gln Ile Arg Ser Val Thr Pro Asp Asp Asn Leu Gln Lys Ala Leu
225                 230                 235                 240

Arg Gly Gly Cys Met Thr Ala Ile Ile Ser Pro Glu Gly Arg His Leu
                245                 250                 255

Ala Pro Pro Leu Ser Glu Gly Glu Gly Ile Leu Met Ala Asp Leu Asp
            260                 265                 270

Met Ser Leu Ile Val Lys Lys Lys Arg Leu Met Asp Thr Leu Gly His
        275                 280                 285

Tyr Ala Arg Pro Glu Val Leu His Leu Leu Val Glu Asn Arg Pro Ala
    290                 295                 300

Ile Thr Val Val Thr Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345
```

<210> SEQ ID NO 46
<211> LENGTH: 1158
<212> TYPE: DNA
<213> ORGANISM: Artificial sequence
<220> FEATURE:
<223> OTHER INFORMATION: codon modified sequence

<400> SEQUENCE: 46

```
atgggccagg ttctgggcgc ccgtgaacag gtccgtgcgg cggtggttca agcctcgccg      60

ttgtttatga acaaaaaagg ctgccttgaa aagggctgcg atctgatcca taaagcgggc     120

aaggaaggtg ccgagatcgt ggtgtttccg gagacctggt tgccgaccta cccgtggtgg     180

gggatgggtt gggaaaccgc ggcagcggcg tttgcagacg tgcatgcgga aatgcaggat     240
```

```
aacagtatcg tggtcggtag ccgtgacacg gaaatcttag gcaaagcggc gcgcgaagcg    300

ggcgcttatg ttgtcctggg ctgccaggag ctggatgaaa aaattggcag ccgcaccctc    360

tttaattccc tggtgtatat tggcaaagat ggccgcgtac tggcccgtca ccgcaaattg    420

ttacctacct acatggaacg tatttggtgg ggtcggggcg atgcccgcga cttgaaagtt    480

tttgaaacgg atgttggtcg gattggcggt aacatttgct gggaaaacca tattgtgaac    540

attactgcgt ggtatatggc gcagggtgtg gacattcatg tcgcggtgtg gccgggttta    600

tggaactgcg cggcggcgca gggcgaaagt ttcctgtttg ccggccatga tctgaataaa    660

tgtgatctga ttccggccac tcgtgaacgc gcctttaccg ggcaatgctt tgtgctgtct    720

gcgaataaca ttcttcgcat ggatgatatc ccggacgatt tcccattccg taacaaagtg    780

acatatgctg ggccgggcca gggcgaattt gttggctggg cctgtggagg ttcccatatc    840

gtggcaccca cgtcggaata catcgttccg ccaaccttcg atgtggagac cattctgtat    900

gcagatctga acgccaaata tctgaaagtg gttaaaagcg tatttgattc tgtgggtcac    960

tatacgcgct gggatctggt tagcctgacg aaaaatccgc aaccgtatga acctttagcg   1020

ggtgaaaaac cgatggcgat gccggaagaa cgcctggaac aggttgccga cgcagtggcg   1080

cgcgatttta acctggatgt ggaaaaagtg gataaaattg tccgccaggt gaccacccca   1140

catcgtcagc gtgccgca                                                 1158
```

<210> SEQ ID NO 47
<211> LENGTH: 386
<212> TYPE: PRT
<213> ORGANISM: Artificial sequence
<220> FEATURE:
<223> OTHER INFORMATION: translated protein from codon modified sequence

<400> SEQUENCE: 47

```
Met Gly Gln Val Leu Gly Ala Arg Glu Gln Val Arg Ala Ala Val Val
1               5                   10                  15

Gln Ala Ser Pro Leu Phe Met Asn Lys Lys Gly Cys Leu Glu Lys Gly
            20                  25                  30

Cys Asp Leu Ile His Lys Ala Gly Lys Glu Gly Ala Glu Ile Val Val
        35                  40                  45

Phe Pro Glu Thr Trp Leu Pro Thr Tyr Pro Trp Trp Gly Met Gly Trp
    50                  55                  60

Glu Thr Ala Ala Ala Ala Phe Ala Asp Val His Ala Glu Met Gln Asp
65                  70                  75                  80

Asn Ser Ile Val Val Gly Ser Arg Asp Thr Glu Ile Leu Gly Lys Ala
                85                  90                  95

Ala Arg Glu Ala Gly Ala Tyr Val Val Leu Gly Cys Gln Glu Leu Asp
            100                 105                 110

Glu Lys Ile Gly Ser Arg Thr Leu Phe Asn Ser Leu Val Tyr Ile Gly
        115                 120                 125

Lys Asp Gly Arg Val Leu Ala Arg His Arg Lys Leu Leu Pro Thr Tyr
    130                 135                 140

Met Glu Arg Ile Trp Trp Gly Arg Gly Asp Ala Arg Asp Leu Lys Val
145                 150                 155                 160

Phe Glu Thr Asp Val Gly Arg Ile Gly Gly Asn Ile Cys Trp Glu Asn
                165                 170                 175

His Ile Val Asn Ile Thr Ala Trp Tyr Met Ala Gln Gly Val Asp Ile
            180                 185                 190
```

```
His Val Ala Val Trp Pro Gly Leu Trp Asn Cys Ala Ala Ala Gln Gly
        195                 200                 205

Glu Ser Phe Leu Phe Ala Gly His Asp Leu Asn Lys Cys Asp Leu Ile
    210                 215                 220

Pro Ala Thr Arg Glu Arg Ala Phe Thr Gly Gln Cys Phe Val Leu Ser
225                 230                 235                 240

Ala Asn Asn Ile Leu Arg Met Asp Asp Ile Pro Asp Asp Phe Pro Phe
                245                 250                 255

Arg Asn Lys Val Thr Tyr Ala Gly Pro Gly Gln Gly Glu Phe Val Gly
            260                 265                 270

Trp Ala Cys Gly Gly Ser His Ile Val Ala Pro Thr Ser Glu Tyr Ile
        275                 280                 285

Val Pro Pro Thr Phe Asp Val Glu Thr Ile Leu Tyr Ala Asp Leu Asn
    290                 295                 300

Ala Lys Tyr Leu Lys Val Val Lys Ser Val Phe Asp Ser Val Gly His
305                 310                 315                 320

Tyr Thr Arg Trp Asp Leu Val Ser Leu Thr Lys Asn Pro Gln Pro Tyr
                325                 330                 335

Glu Pro Leu Ala Gly Glu Lys Pro Met Ala Met Pro Glu Glu Arg Leu
            340                 345                 350

Glu Gln Val Ala Asp Ala Val Ala Arg Asp Phe Asn Leu Asp Val Glu
        355                 360                 365

Lys Val Asp Lys Ile Val Arg Gln Val Thr Thr Pro His Arg Gln Arg
    370                 375                 380

Ala Ala
385


<210> SEQ ID NO 48
<211> LENGTH: 1158
<212> TYPE: DNA
<213> ORGANISM: Artificial sequence
<220> FEATURE:
<223> OTHER INFORMATION: codon modified sequence

<400> SEQUENCE: 48

atgggccagg tgttggcggg ccgcgaacag gttcgtgccg cggtggtgca ggcgagccca      60

gtttggatga acaaacgtgc gtgcctggat aaagcttgcg acttgattca ccgggctggc     120

aaagaaggcg ccgaaattgt ggtgtttccg gaaacttggc ttccaaccta tccgtatttt     180

ggcctgggtt gggataccgc ggctgcagcc tatgcggacg ttcatgccga tgtgcaggag     240

aattcggtcg tgatcggttc caaagatagc gatctgctgg cgcgtgccgc gaaagatgcg     300

ggcgcgtatg tggtcatggg ctgtaacgaa ctggaagagc ggattggtag ccgcacgctt     360

tttaacagct tggtgtatat tggtaaagaa ggccgcttag tcgcgcgtca tcgtaaaatt     420

attccgacct acgtggaaaa actgtggtgg ggccgcggag acgcgcgcga tttaaaagtt     480

tttgatacgg atatcgggcg tattggtggt cagatttgct gggaaaacca tattgtgaac     540

ctcagcgcat atttcattgc gcagggcgtg gatattcatg ttgccctgtg gccagccctg     600

tggaactgcg gtgcggcaca aggtgaaacc tatatctggg cggggcacga tatcaacaaa     660

tgcgatattc tgccggccac ccgtgaacgt gcgtttaccg gccagtgctt cgtactgtct     720

gcgaaccagg ttttgcgcat ggaagatgtt ccggatgatt tcccgtttaa aaacaaaatg     780

tcttatgccg gcccgggcca gggcgattac ttaggctggg catgtggtgg gtcccatatt     840

gtggcgccga gcagtgagta tatcgtgccg ccttcatggg atgtggagac tattctgtac     900
```

```
gcagatctga atgccaagta tattaaagtc gtgaaatcga tctacgatag cctgggtcat    960

tatacgcgct gggacctggt gagtctgacc cgccagccgc agccgtttga accgttagcc   1020

ggcgaccgcc cgatggcgat gcctgaagaa aaaatcgaac aggttgccga tgcggtggcg   1080

cgcgaattta atctggatgt ggaaaaagta gacaagatcg ttcgtcaagt cacgaccccc   1140

catcgccaac gcgcggca                                                 1158


<210> SEQ ID NO 49
<211> LENGTH: 386
<212> TYPE: PRT
<213> ORGANISM: Artificial sequence
<220> FEATURE:
<223> OTHER INFORMATION: translated protein from codon modified sequence

<400> SEQUENCE: 49

Met Gly Gln Val Leu Ala Gly Arg Glu Gln Val Arg Ala Ala Val Val
1               5                   10                  15

Gln Ala Ser Pro Val Trp Met Asn Lys Arg Ala Cys Leu Asp Lys Ala
            20                  25                  30

Cys Asp Leu Ile His Arg Ala Gly Lys Glu Gly Ala Glu Ile Val Val
        35                  40                  45

Phe Pro Glu Thr Trp Leu Pro Thr Tyr Pro Tyr Phe Gly Leu Gly Trp
    50                  55                  60

Asp Thr Ala Ala Ala Ala Tyr Ala Asp Val His Ala Asp Val Gln Glu
65                  70                  75                  80

Asn Ser Val Val Ile Gly Ser Lys Asp Ser Asp Leu Leu Ala Arg Ala
                85                  90                  95

Ala Lys Asp Ala Gly Ala Tyr Val Val Met Gly Cys Asn Glu Leu Glu
            100                 105                 110

Glu Arg Ile Gly Ser Arg Thr Leu Phe Asn Ser Leu Val Tyr Ile Gly
        115                 120                 125

Lys Glu Gly Arg Leu Val Ala Arg His Arg Lys Ile Ile Pro Thr Tyr
    130                 135                 140

Val Glu Lys Leu Trp Trp Gly Arg Gly Asp Ala Arg Asp Leu Lys Val
145                 150                 155                 160

Phe Asp Thr Asp Ile Gly Arg Ile Gly Gly Gln Ile Cys Trp Glu Asn
                165                 170                 175

His Ile Val Asn Leu Ser Ala Tyr Phe Ile Ala Gln Gly Val Asp Ile
            180                 185                 190

His Val Ala Leu Trp Pro Ala Leu Trp Asn Cys Gly Ala Ala Gln Gly
        195                 200                 205

Glu Thr Tyr Ile Trp Ala Gly His Asp Ile Asn Lys Cys Asp Ile Leu
    210                 215                 220

Pro Ala Thr Arg Glu Arg Ala Phe Thr Gly Gln Cys Phe Val Leu Ser
225                 230                 235                 240

Ala Asn Gln Val Leu Arg Met Glu Asp Val Pro Asp Asp Phe Pro Phe
                245                 250                 255

Lys Asn Lys Met Ser Tyr Ala Gly Pro Gly Gln Gly Asp Tyr Leu Gly
            260                 265                 270

Trp Ala Cys Gly Gly Ser His Ile Val Ala Pro Ser Ser Glu Tyr Ile
        275                 280                 285

Val Pro Pro Ser Trp Asp Val Glu Thr Ile Leu Tyr Ala Asp Leu Asn
    290                 295                 300

Ala Lys Tyr Ile Lys Val Val Lys Ser Ile Tyr Asp Ser Leu Gly His
305                 310                 315                 320
```

```
Tyr Thr Arg Trp Asp Leu Val Ser Leu Thr Arg Gln Pro Gln Pro Phe
                325                 330                 335

Glu Pro Leu Ala Gly Asp Arg Pro Met Ala Met Pro Glu Glu Lys Ile
            340                 345                 350

Glu Gln Val Ala Asp Ala Val Ala Arg Glu Phe Asn Leu Asp Val Glu
        355                 360                 365

Lys Val Asp Lys Ile Val Arg Gln Val Thr Thr Pro His Arg Gln Arg
    370                 375                 380

Ala Ala
385


<210> SEQ ID NO 50
<211> LENGTH: 1158
<212> TYPE: DNA
<213> ORGANISM: Artificial sequence
<220> FEATURE:
<223> OTHER INFORMATION: codon modified sequence

<400> SEQUENCE: 50

atgggccagg ttatggcggc acgtgagcag gtgcgggcgg cagtagtcca gggttctccg     60

ttgttcatga acaagaaagc gtgtatcgat aaagcctgtg aactgattca taaagccgcg    120

aaagaaggcg cggagattgt ggtgtttccg gaatcctttg tgccgaccta tccgttctat    180

ggcctcgctt atgaaagcgc gggcggtgcg tttgcggaag ttcatgcaga tttgcaggat    240

aactcgttgg tgttaggtag taaagatacg gacatcttag ggaaagccgc aaaagatgcg    300

ggtgcctatg tggttgtggg ctgcaatgaa ctggatgatc gtgtgggcag ccgcacgctg    360

tttaactcca tgatctatat cggcaaagac ggtaagctga tcgcccgcca tcgtaaactg    420

gttccgacct ttattgaacg cctgtattgg ggccgcggcg atggccgtga catcaaagtc    480

tttgataccg atttaggccg cattggcggc cagatttgct gggaaaatca tattgtgaac    540

gtcacggcgt ggttcattgc gcagggcgta gatatccatg tggccgtttg gccaggtctg    600

ttcaattgcg gtgcgggcca ggccgaatct tttgtctttg ccgcgcatga aatgaacaaa    660

tgcgatctga ttccggcgac tcgcgagcgc gcgtttacgg gtcaatgctt tgtgctgtcg    720

gcgaaccagg tgctgcgcat ggatgatatg cctgatgagt atccgtttaa aaaccgtatt    780

acctttgcag gtccaggtca aggagactat atggggtggg cctgcggcgg tagtcacatt    840

gtggcgccca gcagtgatta cattgttccg ccgagctatg acattgaaac catcctgtac    900

gcagatctga acgccaaata catgaaagtg gtgaagagcg tgttcgattc cgtggggcac    960

tacacccgtt gggatcttgt tagcctttcg aaaaacccaa atccgtttga accgctggcc   1020

ggcgaaaaac cgatggcgct gcctgaagaa aaactggaac agattgcgga tgcggtggct   1080

cgtgaattta acctcgacgt ggaaaaagtt gataaaattg ttcgtcaggt caccaccccg   1140

catcgccaac gcgccgcg                                                  1158


<210> SEQ ID NO 51
<211> LENGTH: 386
<212> TYPE: PRT
<213> ORGANISM: Artificial sequence
<220> FEATURE:
<223> OTHER INFORMATION: translated protein from codon modified sequence

<400> SEQUENCE: 51

Met Gly Gln Val Met Ala Ala Arg Glu Gln Val Arg Ala Ala Val Val
1               5                   10                  15
```

```
Gln Gly Ser Pro Leu Phe Met Asn Lys Lys Ala Cys Ile Asp Lys Ala
            20                  25                  30

Cys Glu Leu Ile His Lys Ala Ala Lys Glu Gly Ala Glu Ile Val Val
        35                  40                  45

Phe Pro Glu Ser Phe Val Pro Thr Tyr Pro Phe Tyr Gly Leu Ala Tyr
    50                  55                  60

Glu Ser Ala Gly Gly Ala Phe Ala Glu Val His Ala Asp Leu Gln Asp
65                  70                  75                  80

Asn Ser Leu Val Leu Gly Ser Lys Asp Thr Asp Ile Leu Gly Lys Ala
                85                  90                  95

Ala Lys Asp Ala Gly Ala Tyr Val Val Val Gly Cys Asn Glu Leu Asp
            100                 105                 110

Asp Arg Val Gly Ser Arg Thr Leu Phe Asn Ser Met Ile Tyr Ile Gly
        115                 120                 125

Lys Asp Gly Lys Leu Ile Ala Arg His Arg Lys Leu Val Pro Thr Phe
    130                 135                 140

Ile Glu Arg Leu Tyr Trp Gly Arg Gly Asp Gly Arg Asp Ile Lys Val
145                 150                 155                 160

Phe Asp Thr Asp Leu Gly Arg Ile Gly Gly Gln Ile Cys Trp Glu Asn
                165                 170                 175

His Ile Val Asn Val Thr Ala Trp Phe Ile Ala Gln Gly Val Asp Ile
            180                 185                 190

His Val Ala Val Trp Pro Gly Leu Phe Asn Cys Gly Ala Gly Gln Ala
        195                 200                 205

Glu Ser Phe Val Phe Ala Ala His Glu Met Asn Lys Cys Asp Leu Ile
    210                 215                 220

Pro Ala Thr Arg Glu Arg Ala Phe Thr Gly Gln Cys Phe Val Leu Ser
225                 230                 235                 240

Ala Asn Gln Val Leu Arg Met Asp Asp Met Pro Asp Glu Tyr Pro Phe
                245                 250                 255

Lys Asn Arg Ile Thr Phe Ala Gly Pro Gly Gln Gly Asp Tyr Met Gly
            260                 265                 270

Trp Ala Cys Gly Gly Ser His Ile Val Ala Pro Ser Ser Asp Tyr Ile
        275                 280                 285

Val Pro Pro Ser Tyr Asp Ile Glu Thr Ile Leu Tyr Ala Asp Leu Asn
    290                 295                 300

Ala Lys Tyr Met Lys Val Val Lys Ser Val Phe Asp Ser Val Gly His
305                 310                 315                 320

Tyr Thr Arg Trp Asp Leu Val Ser Leu Ser Lys Asn Pro Asn Pro Phe
                325                 330                 335

Glu Pro Leu Ala Gly Glu Lys Pro Met Ala Leu Pro Glu Glu Lys Leu
            340                 345                 350

Glu Gln Ile Ala Asp Ala Val Ala Arg Glu Phe Asn Leu Asp Val Glu
        355                 360                 365

Lys Val Asp Lys Ile Val Arg Gln Val Thr Thr Pro His Arg Gln Arg
    370                 375                 380

Ala Ala
385
```

<210> SEQ ID NO 52
<211> LENGTH: 972
<212> TYPE: DNA
<213> ORGANISM: Artificial sequence
<220> FEATURE:
<223> OTHER INFORMATION: codon modified sequence

<400> SEQUENCE: 52

```
atgacccgtg ttgcggcgat tcaaattgaa gcgaaagtgg cggacgtcca gtttaacttg     60

gaacaggcgt ctcgcttgat cgatgaagcc gcaagccgtg gcgcggagat tattgcgctg    120

cctgagtttt tcacgactcg cattgtgtat gatgagcgtc tgttcgaatg ctcagttcca    180

cctgaaaacc cggctctgga tatgctgaaa gccaaagcag cccgttacgg tgcgatgatc    240

ggtggctcgt ttctggaatt acgtgatggc gacgtgtata acacctatac cctggttgaa    300

ccggatggca ccctgcaccg ccatgataaa gaccgcccga ccatggtaga gaacgcgttc    360

tataccgcgg gcagcgatga tgcgtacttc gatacggccg ttggtccagt gggcacggcg    420

gtttgttggg aaatcattcg gaccgccact gtgcggcgcc tcgcaggcaa agtgggtctg    480

atgatgaccg gttcccactt ttggagcgct cccggttggc agttttggcg ctcctttgat    540

cgtcgctttc ataaagcgaa tgcgaaagcc atggaaatca ccccgccgcg ctttgcctcg    600

attctgggcg cgccgctgct tcatgccggg cataccggaa tgcttgaagg cggctttctg    660

gtgctgccgg gtacgcgcat ctctgtcccg actaaaaccc agttaatggg tgaaacccag    720

attattgatg gcgaaggcgc cgtggtggcc cgccgtcatt atacggaagg ggcgggcatg    780

gtgggtggcg aaattgaatt aggcgcaacc agcccgcgta aggcccccgcc ggatcgtttt    840

tgggttccaa acgtcgaagg gttcccgaaa gcgttgtggc tgcatcagaa cccagcaggt    900

gcaagtgtgt ataaatttgc gcgcaaaacg ggccgcctga agacatatga ctttagtcgt    960

aatgcgcgcc cg                                                        972
```

<210> SEQ ID NO 53
<211> LENGTH: 324
<212> TYPE: PRT
<213> ORGANISM: Artificial sequence
<220> FEATURE:
<223> OTHER INFORMATION: translated protein from codon modified sequence

<400> SEQUENCE: 53

```
Met Thr Arg Val Ala Ala Ile Gln Ile Glu Ala Lys Val Ala Asp Val
1               5                   10                  15

Gln Phe Asn Leu Glu Gln Ala Ser Arg Leu Ile Asp Glu Ala Ala Ser
            20                  25                  30

Arg Gly Ala Glu Ile Ile Ala Leu Pro Glu Phe Phe Thr Thr Arg Ile
        35                  40                  45

Val Tyr Asp Glu Arg Leu Phe Glu Cys Ser Val Pro Pro Glu Asn Pro
    50                  55                  60

Ala Leu Asp Met Leu Lys Ala Lys Ala Ala Arg Tyr Gly Ala Met Ile
65                  70                  75                  80

Gly Gly Ser Phe Leu Glu Leu Arg Asp Gly Asp Val Tyr Asn Thr Tyr
                85                  90                  95

Thr Leu Val Glu Pro Asp Gly Thr Leu His Arg His Asp Lys Asp Arg
            100                 105                 110

Pro Thr Met Val Glu Asn Ala Phe Tyr Thr Ala Gly Ser Asp Asp Ala
        115                 120                 125

Tyr Phe Asp Thr Ala Val Gly Pro Val Gly Thr Ala Val Cys Trp Glu
    130                 135                 140

Ile Ile Arg Thr Ala Thr Val Arg Arg Leu Ala Gly Lys Val Gly Leu
145                 150                 155                 160

Met Met Thr Gly Ser His Phe Trp Ser Ala Pro Gly Trp Gln Phe Trp
                165                 170                 175
```

```
Arg Ser Phe Asp Arg Arg Phe His Lys Ala Asn Ala Lys Ala Met Glu
            180                 185                 190

Ile Thr Pro Pro Arg Phe Ala Ser Ile Leu Gly Ala Pro Leu Leu His
        195                 200                 205

Ala Gly His Thr Gly Met Leu Glu Gly Gly Phe Leu Val Leu Pro Gly
    210                 215                 220

Thr Arg Ile Ser Val Pro Thr Lys Thr Gln Leu Met Gly Glu Thr Gln
225                 230                 235                 240

Ile Ile Asp Gly Glu Gly Ala Val Val Ala Arg Arg His Tyr Thr Glu
                245                 250                 255

Gly Ala Gly Met Val Gly Gly Glu Ile Glu Leu Gly Ala Thr Ser Pro
            260                 265                 270

Arg Lys Ala Pro Pro Asp Arg Phe Trp Val Pro Asn Val Glu Gly Phe
        275                 280                 285

Pro Lys Ala Leu Trp Leu His Gln Asn Pro Ala Gly Ala Ser Val Tyr
    290                 295                 300

Lys Phe Ala Arg Lys Thr Gly Arg Leu Lys Thr Tyr Asp Phe Ser Arg
305                 310                 315                 320

Asn Ala Arg Pro


<210> SEQ ID NO 54
<211> LENGTH: 972
<212> TYPE: DNA
<213> ORGANISM: Artificial sequence
<220> FEATURE:
<223> OTHER INFORMATION: codon modified sequence

<400> SEQUENCE: 54

atgacccgcg tggcggccat tcagatggaa gcaaaggtcg gtgatattaa ctttaacctg      60

gatcaggcct cccgtgtgat cgaagaagcc gcgtcgcgcg gtgcggaaat tatcgccctg     120

ccagagtatt ttaccagccg catcatctat gaagacaaac tgtttgaatg ctcaatcccg     180

ccggagcagc cagccattga gatgttgcgc gcgaaagccg cgaagtatgg tgcgatcatt     240

ggcggttcgt tcgtagagat gcgcgacggc gatctgtata acacctttac gctggtggaa     300

ccggatggca ctatccatcg tcatgataaa gatcgtccga ccatggtgga acaaggtttt     360

tataccgcgg gtagcgatga tgggtatttt gataccgcga tgggcccggt tggcaccggc     420

gtgtgttggg aaattattcg gaccgcaacc gttcgcaaac tcgcggggaa agtggcgctg     480

atgatgacgg gtagccattg gtggtccgcg ccgggttgga acttctggaa aacctttgac     540

cggcgctttc ataaaggcaa tgcgaaagcg atggaaattt ctccaccgcg ttgggcaagc     600

ctggtcggcg ctccgttgat ccatgccggc catagtggaa tgattgaagg ggccttcctt     660

gtgctgcctg gcacccgtat tagtattccg acacgcacgc agattatggg tgaaacgcag     720

attattgatg gcgaaggtgc cgttgttggc cgtcgccact acactgaagg cgcgggcctg     780

gtgggcggtg aaattgaact ggcagcgacg tctcctaaaa aagccccacc ggatcgtttt     840

tggattccga acttagaagg ctttccgaaa gctctgtggt tacaccagaa tccgggtggc     900

gcaagcgtgt accgctttgc gaaacgcacg ggccgtctga aaacctatga tttcagccgc     960

aacgcgcgtc cc                                                         972


<210> SEQ ID NO 55
<211> LENGTH: 324
<212> TYPE: PRT
<213> ORGANISM: Artificial sequence
```

<220> FEATURE:
<223> OTHER INFORMATION: translated protein from codon modified sequence

<400> SEQUENCE: 55

```
Met Thr Arg Val Ala Ala Ile Gln Met Glu Ala Lys Val Gly Asp Ile
1               5                   10                  15

Asn Phe Asn Leu Asp Gln Ala Ser Arg Val Ile Glu Glu Ala Ala Ser
            20                  25                  30

Arg Gly Ala Glu Ile Ile Ala Leu Pro Glu Tyr Phe Thr Ser Arg Ile
        35                  40                  45

Ile Tyr Glu Asp Lys Leu Phe Glu Cys Ser Ile Pro Pro Glu Gln Pro
    50                  55                  60

Ala Ile Glu Met Leu Arg Ala Lys Ala Ala Lys Tyr Gly Ala Ile Ile
65                  70                  75                  80

Gly Gly Ser Phe Val Glu Met Arg Asp Gly Asp Leu Tyr Asn Thr Phe
                85                  90                  95

Thr Leu Val Glu Pro Asp Gly Thr Ile His Arg His Asp Lys Asp Arg
            100                 105                 110

Pro Thr Met Val Glu Gln Gly Phe Tyr Thr Ala Gly Ser Asp Asp Gly
        115                 120                 125

Tyr Phe Asp Thr Ala Met Gly Pro Val Gly Thr Gly Val Cys Trp Glu
    130                 135                 140

Ile Ile Arg Thr Ala Thr Val Arg Lys Leu Ala Gly Lys Val Ala Leu
145                 150                 155                 160

Met Met Thr Gly Ser His Trp Trp Ser Ala Pro Gly Trp Asn Phe Trp
                165                 170                 175

Lys Thr Phe Asp Arg Arg Phe His Lys Gly Asn Ala Lys Ala Met Glu
            180                 185                 190

Ile Ser Pro Pro Arg Trp Ala Ser Leu Val Gly Ala Pro Leu Ile His
        195                 200                 205

Ala Gly His Ser Gly Met Ile Glu Gly Ala Phe Leu Val Leu Pro Gly
    210                 215                 220

Thr Arg Ile Ser Ile Pro Thr Arg Thr Gln Ile Met Gly Glu Thr Gln
225                 230                 235                 240

Ile Ile Asp Gly Glu Gly Ala Val Val Gly Arg Arg His Tyr Thr Glu
                245                 250                 255

Gly Ala Gly Leu Val Gly Gly Glu Ile Glu Leu Ala Ala Thr Ser Pro
            260                 265                 270

Lys Lys Ala Pro Pro Asp Arg Phe Trp Ile Pro Asn Leu Glu Gly Phe
        275                 280                 285

Pro Lys Ala Leu Trp Leu His Gln Asn Pro Gly Gly Ala Ser Val Tyr
    290                 295                 300

Arg Phe Ala Lys Arg Thr Gly Arg Leu Lys Thr Tyr Asp Phe Ser Arg
305                 310                 315                 320

Asn Ala Arg Pro
```

<210> SEQ ID NO 56
<211> LENGTH: 972
<212> TYPE: DNA
<213> ORGANISM: Artificial sequence
<220> FEATURE:
<223> OTHER INFORMATION: codon modified sequence

<400> SEQUENCE: 56

```
atgacccgcg ttgcggcgat tcagttggaa ggtcgtttag gcgatctgaa ctacaatatg     60
```

```
gatcaagcga gccgcatgat cgaagacgcc ggcacgaaag gggcggaaat tattgcgtta    120

ccggagttct ttacgagtcg tattatttat gaagatcgtg tgtttgaatg cagcctgccg    180

ccagataacc cagcaatgga aatcttgcgg gcaaaagcgg ccaaatttgg ggcgatgatt    240

ggtggctcct atatcgaaat gcgtgaaggc gatctgtata atacctatac cctggttgat    300

ccggacggca cggtccataa acatgataaa gatcgtcctt cgatgttaga gaacgcgttt    360

tatagcggtg gttccgacga tggctacttc gaaaccggtc tgggcccggt tggcaccgcc    420

gtgtgttggg aaattattcg tactgcgacc gtgcgccgtc ttgcggcgcg cgtgggcgtg    480

atgatgactg gttcccattg gttttctgcg ccgggttgga actattggcg cagttttgaa    540

aagcgtttcc acaagggcca ggccaaagca ttggaggtga gcccgccacg ctgggccagc    600

atgatcggcg cgcccctgat tcacgcgggg cataccggca tgatcgaagg tggttttctg    660

gtcctgccag gtacccgcat ttcggtgccg accaaaacga acattgtcgg cgaaacccag    720

atcatcgatg gcgaaggtgc cgtggtggcc cgtcgccatt ggacagaagg cgccggggtt    780

gtaggcggcg aaattgagct tgccgcttcg agtccgaaaa aagcgccgcc ggatcggttt    840

tgggttccga atctggaagg tttcccgaaa gcgctgtggc tgcatcagaa cccgggcgca    900

gccagcctgt atcgctatgc aaaacgcacg ggccgcatta aaacctacga tttttctcgt    960

aacgcgcgcc ct                                                        972
```

<210> SEQ ID NO 57
<211> LENGTH: 324
<212> TYPE: PRT
<213> ORGANISM: Artificial sequence
<220> FEATURE:
<223> OTHER INFORMATION: translated protein from codon modified sequence

<400> SEQUENCE: 57

```
Met Thr Arg Val Ala Ala Ile Gln Leu Glu Gly Arg Leu Gly Asp Leu
1               5                   10                  15

Asn Tyr Asn Met Asp Gln Ala Ser Arg Met Ile Glu Asp Ala Gly Thr
            20                  25                  30

Lys Gly Ala Glu Ile Ile Ala Leu Pro Glu Phe Phe Thr Ser Arg Ile
        35                  40                  45

Ile Tyr Glu Asp Arg Val Phe Glu Cys Ser Leu Pro Pro Asp Asn Pro
    50                  55                  60

Ala Met Glu Ile Leu Arg Ala Lys Ala Ala Lys Phe Gly Ala Met Ile
65                  70                  75                  80

Gly Gly Ser Tyr Ile Glu Met Arg Glu Gly Asp Leu Tyr Asn Thr Tyr
                85                  90                  95

Thr Leu Val Asp Pro Asp Gly Thr Val His Lys His Asp Lys Asp Arg
            100                 105                 110

Pro Ser Met Leu Glu Asn Ala Phe Tyr Ser Gly Gly Ser Asp Asp Gly
        115                 120                 125

Tyr Phe Glu Thr Gly Leu Gly Pro Val Gly Thr Ala Val Cys Trp Glu
    130                 135                 140

Ile Ile Arg Thr Ala Thr Val Arg Arg Leu Ala Ala Arg Val Gly Val
145                 150                 155                 160

Met Met Thr Gly Ser His Trp Phe Ser Ala Pro Gly Trp Asn Tyr Trp
                165                 170                 175

Arg Ser Phe Glu Lys Arg Phe His Lys Gly Gln Ala Lys Ala Leu Glu
            180                 185                 190

Val Ser Pro Pro Arg Trp Ala Ser Met Ile Gly Ala Pro Leu Ile His
```

```
        195                 200                 205

Ala Gly His Thr Gly Met Ile Glu Gly Gly Phe Leu Val Leu Pro Gly
    210                 215                 220

Thr Arg Ile Ser Val Pro Thr Lys Thr Asn Ile Val Gly Glu Thr Gln
225                 230                 235                 240

Ile Ile Asp Gly Glu Gly Ala Val Val Ala Arg Arg His Trp Thr Glu
                245                 250                 255

Gly Ala Gly Val Val Gly Gly Glu Ile Glu Leu Ala Ala Ser Ser Pro
            260                 265                 270

Lys Lys Ala Pro Pro Asp Arg Phe Trp Val Pro Asn Leu Glu Gly Phe
        275                 280                 285

Pro Lys Ala Leu Trp Leu His Gln Asn Pro Gly Ala Ala Ser Leu Tyr
    290                 295                 300

Arg Tyr Ala Lys Arg Thr Gly Arg Ile Lys Thr Tyr Asp Phe Ser Arg
305                 310                 315                 320

Asn Ala Arg Pro
```

<210> SEQ ID NO 58
<211> LENGTH: 1059
<212> TYPE: DNA
<213> ORGANISM: Artificial sequence
<220> FEATURE:
<223> OTHER INFORMATION: codon modified sequence

<400> SEQUENCE: 58

```
atgaatgagg gttttcagaa agtgcgtgtg gccgccgcac agatttcccc ggcgtggatg     60

gatcgtgaag gttcaacgga aatcgcctgc cattggattg cggaggcagc gcgcggtggg    120

gcggaactcc tgagctttgg cgaagcgtgg ttgccagcct atccgtggtg gattttcgtt    180

ggctcaccga tctactctgc gaactttagt aaacgcgttt ttgataacgc cgtggaagtt    240

cctagcgcaa ctactgaccg cttgtgtgaa gccgcgcgca aagcgggcgt gcatgtcgtg    300

atgggcctta ccgaactgtg ggcggctcc gtgtatttag ctcaagtttt tattaacgat    360

cgcggtgaac tggttgcgca ccgtcgcaaa attaaaccga cccattttga gcgtgcaatt    420

tggggcgagg gtgaaggcag tgattttttt gtgatcccga cctctctggc gcgcttaggc    480

gcgctgaact gctgggaaca tctccagcca ctgaacttgt tcgcgatgaa cgcgttcggt    540

gaacagattc atgtcgccgc gtggccggcg ttcgcgattt ataatcgtgt cgacccgtcg    600

tataccaacg aagcaaacct ggcggctagc cgtgcctatg cactggcaac gcagaccttt    660

gtgatccaca cctcggcggt agttgatgaa ggtaccgttg atctgatttg tgatgatgat    720

gaaaaacgct taatcctgga aagtggcgcc ggccagtgcg cggtgattaa ccccctgggg    780

gcgatcattt cgaccccggt gagctccacc gcccagggca ttgtgtatgc ggactgcgac    840

tttggccttg tggcctctgc gaaaatgagc aacgatccgg cggggcatta ccaacggggt    900

gatgttttcc aggtgcactt taatcctgcc ccgcgtcgcc cgctggtgcc gcggggtgcc    960

attgcggcag atccaacgac ggcggcgagc gaagatctgc cgaatatcaa gcatccgcca   1020

tttagcccgg ccgtgaaact gccgattgtg gtcgatgat                          1059
```

<210> SEQ ID NO 59
<211> LENGTH: 353
<212> TYPE: PRT
<213> ORGANISM: Artificial sequence
<220> FEATURE:
<223> OTHER INFORMATION: translated protein from codon modified sequence

<400> SEQUENCE: 59

Met Asn Glu Gly Phe Gln Lys Val Arg Val Ala Ala Ala Gln Ile Ser
1 5 10 15

Pro Ala Trp Met Asp Arg Glu Gly Ser Thr Glu Ile Ala Cys His Trp
20 25 30

Ile Ala Glu Ala Ala Arg Gly Gly Ala Glu Leu Leu Ser Phe Gly Glu
35 40 45

Ala Trp Leu Pro Ala Tyr Pro Trp Trp Ile Phe Val Gly Ser Pro Ile
50 55 60

Tyr Ser Ala Asn Phe Ser Lys Arg Val Phe Asp Asn Ala Val Glu Val
65 70 75 80

Pro Ser Ala Thr Thr Asp Arg Leu Cys Glu Ala Ala Arg Lys Ala Gly
85 90 95

Val His Val Val Met Gly Leu Thr Glu Leu Trp Gly Gly Ser Val Tyr
100 105 110

Leu Ala Gln Val Phe Ile Asn Asp Arg Gly Glu Leu Val Ala His Arg
115 120 125

Arg Lys Ile Lys Pro Thr His Phe Glu Arg Ala Ile Trp Gly Glu Gly
130 135 140

Glu Gly Ser Asp Phe Phe Val Ile Pro Thr Ser Leu Ala Arg Leu Gly
145 150 155 160

Ala Leu Asn Cys Trp Glu His Leu Gln Pro Leu Asn Leu Phe Ala Met
165 170 175

Asn Ala Phe Gly Glu Gln Ile His Val Ala Ala Trp Pro Ala Phe Ala
180 185 190

Ile Tyr Asn Arg Val Asp Pro Ser Tyr Thr Asn Glu Ala Asn Leu Ala
195 200 205

Ala Ser Arg Ala Tyr Ala Leu Ala Thr Gln Thr Phe Val Ile His Thr
210 215 220

Ser Ala Val Val Asp Glu Gly Thr Val Asp Leu Ile Cys Asp Asp Asp
225 230 235 240

Glu Lys Arg Leu Ile Leu Glu Ser Gly Ala Gly Gln Cys Ala Val Ile
245 250 255

Asn Pro Leu Gly Ala Ile Ile Ser Thr Pro Val Ser Ser Thr Ala Gln
260 265 270

Gly Ile Val Tyr Ala Asp Cys Asp Phe Gly Leu Val Ala Ser Ala Lys
275 280 285

Met Ser Asn Asp Pro Ala Gly His Tyr Gln Arg Gly Asp Val Phe Gln
290 295 300

Val His Phe Asn Pro Ala Pro Arg Arg Pro Leu Val Pro Arg Gly Ala
305 310 315 320

Ile Ala Ala Asp Pro Thr Thr Ala Ala Ser Glu Asp Leu Pro Asn Ile
325 330 335

Lys His Pro Pro Phe Ser Pro Ala Val Lys Leu Pro Ile Val Val Asp
340 345 350

Asp

<210> SEQ ID NO 60
<211> LENGTH: 1059
<212> TYPE: DNA
<213> ORGANISM: Artificial sequence
<220> FEATURE:
<223> OTHER INFORMATION: codon modified sequence

<400> SEQUENCE: 60

```
atgaatgaag cgtttcagaa actccgtgtg gccgccgcgc agctgtcccc agcctttctg     60

gataaagatg gttccacgga cattgcgtgt cattatattg cggacgcggc acgcggcggt    120

gcggaattat tgtcatttgg ggaggcgttt ttaccggcct atccattttg gattttcatc    180

ggtagcccgt tgtattctgc acaattttcg cgccgtcttt acgataatgc agttgagctg    240

ccatctgcga ccaccgatcg cttgtgcgat gcagcccgca aagcgggcat gcatgtggtg    300

atgggcctga ccgaactgta tggcggttct atttacctgg cgcaagtgtt tatcaacgac    360

cgtggcgaaa ttctgggtca tcgtcggaaa gttaaaccga cccactggga acgcgccatt    420

tgggcagaag gcgatgggtc ggatttcttt gttatcccga gcagcgtggc ccgcctgggc    480

gcactgaatt gctgggagca catccagcct ttaaacgtat ttggccttaa cgccttcggt    540

gaacagattc atgtcgccgc ctggcctgcg tttgcggtct ataaccgtgt ggacccgtca    600

ttttccaacg aagccaacat ggccgcgacc aaagcgtatg cgatggcaac ccagacgttc    660

gtgattcaca ctagcgcgat tgtggatgat gcaacgatcg atctggtgtg tgaagatgat    720

gaaaagcgtt tgctgatgga cagcggcgcg ggccagtgcg cggttatcaa cccgctgggt    780

gcgctgatta gtaccccatt aagctcgacc ggacaaggcc tggtttttgc tgattgcgat    840

tttgcggttg tggcgagcgc gaaagtcagc caggatccgg ccggccatta tcagcgcggt    900

gatgtgttca acgtgcattt taacccggcc ccgcgccgcc ccctggtccc gaaagcggct    960

attgcggccg atccgacgac tgcggcgagt gaagatatgc cgcagatcaa acatccgccg   1020

tttagtccgg cggtgaaact gccgattgtt gtggacgat                          1059
```

```
<210> SEQ ID NO 61
<211> LENGTH: 353
<212> TYPE: PRT
<213> ORGANISM: Artificial sequence
<220> FEATURE:
<223> OTHER INFORMATION: translated protein from codon modified sequence

<400> SEQUENCE: 61

Met Asn Glu Ala Phe Gln Lys Leu Arg Val Ala Ala Ala Gln Leu Ser
1               5                   10                  15

Pro Ala Phe Leu Asp Lys Asp Gly Ser Thr Asp Ile Ala Cys His Tyr
            20                  25                  30

Ile Ala Asp Ala Ala Arg Gly Gly Ala Glu Leu Leu Ser Phe Gly Glu
        35                  40                  45

Ala Phe Leu Pro Ala Tyr Pro Phe Trp Ile Phe Ile Gly Ser Pro Leu
    50                  55                  60

Tyr Ser Ala Gln Phe Ser Arg Arg Leu Tyr Asp Asn Ala Val Glu Leu
65                  70                  75                  80

Pro Ser Ala Thr Thr Asp Arg Leu Cys Asp Ala Ala Arg Lys Ala Gly
                85                  90                  95

Met His Val Val Met Gly Leu Thr Glu Leu Tyr Gly Gly Ser Ile Tyr
            100                 105                 110

Leu Ala Gln Val Phe Ile Asn Asp Arg Gly Glu Ile Leu Gly His Arg
        115                 120                 125

Arg Lys Val Lys Pro Thr His Trp Glu Arg Ala Ile Trp Ala Glu Gly
    130                 135                 140

Asp Gly Ser Asp Phe Phe Val Ile Pro Ser Ser Val Ala Arg Leu Gly
145                 150                 155                 160

Ala Leu Asn Cys Trp Glu His Ile Gln Pro Leu Asn Val Phe Gly Leu
                165                 170                 175
```

```
Asn Ala Phe Gly Glu Gln Ile His Val Ala Ala Trp Pro Ala Phe Ala
            180                 185                 190

Val Tyr Asn Arg Val Asp Pro Ser Phe Ser Asn Glu Ala Asn Met Ala
        195                 200                 205

Ala Thr Lys Ala Tyr Ala Met Ala Thr Gln Thr Phe Val Ile His Thr
    210                 215                 220

Ser Ala Ile Val Asp Asp Ala Thr Ile Asp Leu Val Cys Glu Asp Asp
225                 230                 235                 240

Glu Lys Arg Leu Leu Met Asp Ser Gly Ala Gly Gln Cys Ala Val Ile
                245                 250                 255

Asn Pro Leu Gly Ala Leu Ile Ser Thr Pro Leu Ser Ser Thr Gly Gln
            260                 265                 270

Gly Leu Val Phe Ala Asp Cys Asp Phe Ala Val Val Ala Ser Ala Lys
        275                 280                 285

Val Ser Gln Asp Pro Ala Gly His Tyr Gln Arg Gly Asp Val Phe Asn
    290                 295                 300

Val His Phe Asn Pro Ala Pro Arg Arg Pro Leu Val Pro Lys Ala Ala
305                 310                 315                 320

Ile Ala Ala Asp Pro Thr Thr Ala Ala Ser Glu Asp Met Pro Gln Ile
                325                 330                 335

Lys His Pro Pro Phe Ser Pro Ala Val Lys Leu Pro Ile Val Val Asp
            340                 345                 350

Asp


<210> SEQ ID NO 62
<211> LENGTH: 1059
<212> TYPE: DNA
<213> ORGANISM: Artificial sequence
<220> FEATURE:
<223> OTHER INFORMATION: codon modified sequence

<400> SEQUENCE: 62

atgaacgatg gcttcaaccg cgtccgcgtg gcggcggcgc agatgagtcc tgcgtggatt      60

gatcgggaag gctcgactga cattgcctgt cactggattg ctgatgcggc gcgcggcggc     120

gcggaattac ttagctttgg tgaggccttt attccggcct atccctggtt tattttcctg     180

ggctccccgg tttacaccgc acagtttacg cgtaaactgt gggatcaagc gctggaagtg     240

ccgtctgcca cttctgatcg tctctgtgaa gcggcgaaaa aagctgggct gcatgtggtg     300

atcggcttgt cggaaatttg gggcggcagc atctatctgg cgcagctgtt tattaacgat     360

aaaggtgaac tgatcggcca ccgtcgcaaa attcgtccga cccattacga acgcgcggta     420

tggggcgagg gggatggtag cgaatttttt attttgccga ccaccattgg tcgcttgggg     480

gcaatgaatt gctgggaaca tttacagccg ctgaacctgt atgcactgaa cgcgtttggt     540

gagcagattc atgtggccgc ctggcctgcg tttgcgattt atcagcgtgt cgatccatcc     600

ttcaccaatg acgcgaacat cgcagccagc cgcgcctatg ccattgcgac gcaaagtttt     660

gtgattcata cgtcagcggt cgttgaagaa gccaccgttg atatgatctg cgacgatgaa     720

gacaaacgcg ttgttcttga aaccggtgcg ggcaactgcg cagttatcaa cccgctgggt     780

gctatcattt cgacgccaat gacctccacc ggccagggta tcgtgttcgc agattgcgat     840

ttcgcgctgt tagcgagcgg caaaatgagt aatgatccgg cgggccacta tcagcgtggt     900

gatgtgtttc aggtccattt taacccagca ccgaaaaaac cgctggtgcc gcgcgcggcc     960

attgcggcgg acccgacgac cgccgccagc gaagatgtgc cgcaaattaa gcatccgccg    1020
```

ttttctccag ccgtgaaact gccgatcgtg gtggatgat 1059

<210> SEQ ID NO 63
<211> LENGTH: 353
<212> TYPE: PRT
<213> ORGANISM: Artificial sequence
<220> FEATURE:
<223> OTHER INFORMATION: translated protein from codon modified sequence

<400> SEQUENCE: 63

```
Met Asn Asp Gly Phe Asn Arg Val Arg Val Ala Ala Ala Gln Met Ser
1               5                   10                  15

Pro Ala Trp Ile Asp Arg Glu Gly Ser Thr Asp Ile Ala Cys His Trp
            20                  25                  30

Ile Ala Asp Ala Ala Arg Gly Gly Ala Glu Leu Leu Ser Phe Gly Glu
        35                  40                  45

Ala Phe Ile Pro Ala Tyr Pro Trp Phe Ile Phe Leu Gly Ser Pro Val
    50                  55                  60

Tyr Thr Ala Gln Phe Thr Arg Lys Leu Trp Asp Gln Ala Leu Glu Val
65                  70                  75                  80

Pro Ser Ala Thr Ser Asp Arg Leu Cys Glu Ala Ala Lys Lys Ala Gly
                85                  90                  95

Leu His Val Val Ile Gly Leu Ser Glu Ile Trp Gly Gly Ser Ile Tyr
            100                 105                 110

Leu Ala Gln Leu Phe Ile Asn Asp Lys Gly Glu Leu Ile Gly His Arg
        115                 120                 125

Arg Lys Ile Arg Pro Thr His Tyr Glu Arg Ala Val Trp Gly Glu Gly
    130                 135                 140

Asp Gly Ser Glu Phe Phe Ile Leu Pro Thr Thr Ile Gly Arg Leu Gly
145                 150                 155                 160

Ala Met Asn Cys Trp Glu His Leu Gln Pro Leu Asn Leu Tyr Ala Leu
                165                 170                 175

Asn Ala Phe Gly Glu Gln Ile His Val Ala Ala Trp Pro Ala Phe Ala
            180                 185                 190

Ile Tyr Gln Arg Val Asp Pro Ser Phe Thr Asn Asp Ala Asn Ile Ala
        195                 200                 205

Ala Ser Arg Ala Tyr Ala Ile Ala Thr Gln Ser Phe Val Ile His Thr
    210                 215                 220

Ser Ala Val Val Glu Glu Ala Thr Val Asp Met Ile Cys Asp Asp Glu
225                 230                 235                 240

Asp Lys Arg Val Val Leu Glu Thr Gly Ala Gly Asn Cys Ala Val Ile
                245                 250                 255

Asn Pro Leu Gly Ala Ile Ile Ser Thr Pro Met Thr Ser Thr Gly Gln
            260                 265                 270

Gly Ile Val Phe Ala Asp Cys Asp Phe Ala Leu Leu Ala Ser Gly Lys
        275                 280                 285

Met Ser Asn Asp Pro Ala Gly His Tyr Gln Arg Gly Asp Val Phe Gln
    290                 295                 300

Val His Phe Asn Pro Ala Pro Lys Lys Pro Leu Val Pro Arg Ala Ala
305                 310                 315                 320

Ile Ala Ala Asp Pro Thr Thr Ala Ala Ser Glu Asp Val Pro Gln Ile
                325                 330                 335

Lys His Pro Pro Phe Ser Pro Ala Val Lys Leu Pro Ile Val Val Asp
            340                 345                 350
```

Asp

<210> SEQ ID NO 64
<211> LENGTH: 1062
<212> TYPE: DNA
<213> ORGANISM: Artificial sequence
<220> FEATURE:
<223> OTHER INFORMATION: codon modified sequence

<400> SEQUENCE: 64
atggaaaacc gctccattgt gcgtgcggcg gcagttcaat tagcaccgga tgttaccagt 60
aaggaaaaaa cgctggcaaa agtgctcgaa gccattcatg aagcggcggg tcgcggcgcg 120
gaattggcgg tttttccgga aacctgggtc ccttggtatc cgtattggag cttcgtcctg 180
ccgccagtcc tgagcgcgaa agaacatgtt cgcatgttcg atgaggcatt aactgtgcca 240
agcgctgcga ccgaagctat cgcttctgcg gcgcgtaacc atggagtggt tgtggtgctt 300
ggggtgaacg aaaaagagca cggcagcctg tacaacaccc agctggtgtt taacgccgag 360
ggtaccctgc tgctgaaacg tcgtaaaatt accccgacgt ttcacgaacg cttattgtgg 420
ggccagggtg atgcgtcggg ccttaccctg gttgaaaccc acatcggtcg catcggcgcc 480
ctggcctgct gggaacattg gaacccgctg gcgcgctatg ccttaatggc ccagcatgaa 540
gatattcatg tggcacagtt tccaggctca atggtggggc cgatttttgc ggatcagatc 600
gacgttacac ttcgccatca cgcgttggaa agtggttgtt ttgtcgtgaa tgcgacgggt 660
ttcctgacgg acgaacaaat tgcaagcatc acgccggatc agaacctcca gaaagcggtg 720
cgcggcggtt gcatgaccgc cattattagt ccggaaggca aacatctggc gccgcctctc 780
tccgaaggcg aaggcgttct gattgccgat ctggatctgt cgctggtgac ccgccggaaa 840
cggatgatgg actccgtggg ccattatgcc cgcccggagc tgctgcatct gatcattgat 900
ggtcgtgcca ccgcgccgat ggtggcctct gaatctagtt ttgaaaatcg taatcccagc 960
cagactgcgt ctccacgtag caacagcgat ggccatcatg ataacgcgag ctcggatcgt 1020
gatccggacc agcgtgtggc cgtattgcgc tcccaagcgt cg 1062

<210> SEQ ID NO 65
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 65

Met Glu Asn Arg Ser Ile Val Arg Ala Ala Ala Val Gln Leu Ala Pro
1 5 10 15

Asp Val Thr Ser Lys Glu Lys Thr Leu Ala Lys Val Leu Glu Ala Ile
20 25 30

His Glu Ala Ala Gly Arg Gly Ala Glu Leu Ala Val Phe Pro Glu Thr
35 40 45

Trp Val Pro Trp Tyr Pro Tyr Trp Ser Phe Val Leu Pro Pro Val Leu
50 55 60

Ser Ala Lys Glu His Val Arg Met Phe Asp Glu Ala Leu Thr Val Pro
65 70 75 80

Ser Ala Ala Thr Glu Ala Ile Ala Ser Ala Ala Arg Asn His Gly Val
85 90 95

Val Val Val Leu Gly Val Asn Glu Lys Glu His Gly Ser Leu Tyr Asn
100 105 110

```
Thr Gln Leu Val Phe Asn Ala Glu Gly Thr Leu Leu Leu Lys Arg Arg
        115                 120                 125

Lys Ile Thr Pro Thr Phe His Glu Arg Leu Leu Trp Gly Gln Gly Asp
    130                 135                 140

Ala Ser Gly Leu Thr Leu Val Glu Thr His Ile Gly Arg Ile Gly Ala
145                 150                 155                 160

Leu Ala Cys Trp Glu His Trp Asn Pro Leu Ala Arg Tyr Ala Leu Met
                165                 170                 175

Ala Gln His Glu Asp Ile His Val Ala Gln Phe Pro Gly Ser Met Val
            180                 185                 190

Gly Pro Ile Phe Ala Asp Gln Ile Asp Val Thr Leu Arg His His Ala
        195                 200                 205

Leu Glu Ser Gly Cys Phe Val Val Asn Ala Thr Gly Phe Leu Thr Asp
    210                 215                 220

Glu Gln Ile Ala Ser Ile Thr Pro Asp Gln Asn Leu Gln Lys Ala Val
225                 230                 235                 240

Arg Gly Gly Cys Met Thr Ala Ile Ile Ser Pro Glu Gly Lys His Leu
                245                 250                 255

Ala Pro Pro Leu Ser Glu Gly Glu Gly Val Leu Ile Ala Asp Leu Asp
            260                 265                 270

Leu Ser Leu Val Thr Arg Arg Lys Arg Met Met Asp Ser Val Gly His
        275                 280                 285

Tyr Ala Arg Pro Glu Leu Leu His Leu Ile Ile Asp Gly Arg Ala Thr
    290                 295                 300

Ala Pro Met Val Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
            340                 345                 350

Ala Ser


<210> SEQ ID NO 66
<211> LENGTH: 1062
<212> TYPE: DNA
<213> ORGANISM: Artificial sequence
<220> FEATURE:
<223> OTHER INFORMATION: codon modified sequence

<400> SEQUENCE: 66

atggaaaaca aatctatttt acgcgcggcg gcggttcaga ttgcgcctga acttacgagc      60

cgtgaaaaaa cggtcgccaa aattattgat gctattcatg aagcggcagg caaaggggcg     120

gaactcgcag tgtttccgga aacgtttatc ccctggtatc cgtattttag ctttttgttg     180

ccaccgctga tgtcgggccg tgaacacgtc cgtctgtacg aagaagcctt atctattccg     240

tccgctgcaa ccgaagcgat tggcacggcc gcccgcaacc atggcgtagt tgtcgttctt     300

ggcctgaacg aaaaagatca tggtagtctg tataacaccc agatcgtgtt taacgcagat     360

ggtaccctgg tgatgaaacg tcgcaagttg actccatcct tccatgagcg gatggtgtgg     420

ggacagggtg atggcagtgg cctgaccctg gtggataccc atctgggccg tatcggcgcg     480

atggcatgct gggagcactg gaatccgctg gcccgctacg ccctgatggc gcagcatgaa     540

gatattcatg tggcgcagtg gccagcgagc atggtgggtc cgatctttgc ggaacagatt     600

gaactgacca tccgtcatca cgcgttagaa agtggctgct ttgtggttaa tgcgacggcc     660
```

```
ttcctgaccg atgatcaact ggccaccatc acccctgatc agaacatcca aaaagcctta    720

aaaggtggct gtgtgactgc gattattagc ccggaaggca aacatttggc gccgccgctg    780

accgagggcg aaggtcttct cattgcggac ctggatctga gcctgctgac acgccgcaaa    840

cgcatgatgg attccctggg tcattatgcg cgcccagaat tattgcatct ggttattgac    900

gcccgtggta cggcgccgat ggtggcctct gaatcgacct atgagaaccg caatccgagc    960

cagaccgcat ctccgcggag caactccgac gggcatcacg ataacgcctc gtcggatcgc   1020

gacccggatc agcgcgttgc ggtgctgcgt agtcaagcga gc                      1062


<210> SEQ ID NO 67
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 67

Met Glu Asn Lys Ser Ile Leu Arg Ala Ala Ala Val Gln Ile Ala Pro
1               5                   10                  15

Glu Leu Thr Ser Arg Glu Lys Thr Val Ala Lys Ile Ile Asp Ala Ile
            20                  25                  30

His Glu Ala Ala Gly Lys Gly Ala Glu Leu Ala Val Phe Pro Glu Thr
        35                  40                  45

Phe Ile Pro Trp Tyr Pro Tyr Phe Ser Phe Leu Leu Pro Pro Leu Met
    50                  55                  60

Ser Gly Arg Glu His Val Arg Leu Tyr Glu Glu Ala Leu Ser Ile Pro
65                  70                  75                  80

Ser Ala Ala Thr Glu Ala Ile Gly Thr Ala Ala Arg Asn His Gly Val
                85                  90                  95

Val Val Val Leu Gly Leu Asn Glu Lys Asp His Gly Ser Leu Tyr Asn
            100                 105                 110

Thr Gln Ile Val Phe Asn Ala Asp Gly Thr Leu Val Met Lys Arg Arg
        115                 120                 125

Lys Leu Thr Pro Ser Phe His Glu Arg Met Val Trp Gly Gln Gly Asp
    130                 135                 140

Gly Ser Gly Leu Thr Leu Val Asp Thr His Leu Gly Arg Ile Gly Ala
145                 150                 155                 160

Met Ala Cys Trp Glu His Trp Asn Pro Leu Ala Arg Tyr Ala Leu Met
                165                 170                 175

Ala Gln His Glu Asp Ile His Val Ala Gln Trp Pro Ala Ser Met Val
            180                 185                 190

Gly Pro Ile Phe Ala Glu Gln Ile Glu Leu Thr Ile Arg His His Ala
        195                 200                 205

Leu Glu Ser Gly Cys Phe Val Val Asn Ala Thr Ala Phe Leu Thr Asp
    210                 215                 220

Asp Gln Leu Ala Thr Ile Thr Pro Asp Gln Asn Ile Gln Lys Ala Leu
225                 230                 235                 240

Lys Gly Gly Cys Val Thr Ala Ile Ile Ser Pro Glu Gly Lys His Leu
                245                 250                 255

Ala Pro Pro Leu Thr Glu Gly Glu Gly Leu Leu Ile Ala Asp Leu Asp
            260                 265                 270

Leu Ser Leu Leu Thr Arg Arg Lys Arg Met Met Asp Ser Leu Gly His
        275                 280                 285

Tyr Ala Arg Pro Glu Leu Leu His Leu Val Ile Asp Ala Arg Gly Thr
```

290 295 300

Ala Pro Met Val Ala Ser Glu Ser Thr Tyr Glu Asn Arg Asn Pro Ser
305 310 315 320

Gln Thr Ala Ser Pro Arg Ser Asn Ser Asp Gly His His Asp Asn Ala
325 330 335

Ser Ser Asp Arg Asp Pro Asp Gln Arg Val Ala Val Leu Arg Ser Gln
340 345 350

Ala Ser

<210> SEQ ID NO 68
<211> LENGTH: 1062
<212> TYPE: DNA
<213> ORGANISM: Artificial sequence
<220> FEATURE:
<223> OTHER INFORMATION: codon modified sequence

<400> SEQUENCE: 68
atggaaaata aaaccgttct gcgtgcagcg gcggtgcagt tgggcccaga tctgacctcg 60
aaagaacgta ccatcgcaaa attgatcgaa gcgatccatg aagcggcggg gaaaggcgcg 120
gaactggccg tgtttccgga aacctttgtt ccgtggtatc cgtactggtc gtgggtgatg 180
ccgccgcttt taacgggcaa agaacatatt cgcttgtatg atgaagccgt gacggttcca 240
agtgccgcca ccgatgggat tgcatcggcg gccaaacaac acggcattgt cgtggtcctg 300
ggtctgaacg atcgtgaaca tggcacgctg tataacacac aggtagtgtt taacgccgac 360
ggcaccgtgg ttctgcgccg gcgtaaagtg actccgacct atcatgaaaa gattgtctgg 420
gcacagggtg aaggttccgg tctgactgtg gtggacaccc atattgcccg catcggcgcg 480
ctggcgtgtt gggagcatta caacccgtta gcgcgctatg cgatgattgc gcaacacgaa 540
gatatccatg ttgcgcaatt tcctgccagc attatgggtc caatgttcgc tgaacagatt 600
gaactgacgc tgcgtcatca cgcgctggaa agcgcgtgct tcgttgtgaa cgcgaccgcg 660
tggttaagcg atgaacagat ggcgagtgtg agcccagagc agcagctgca gcgcgcactg 720
cgtggcgctt gcatgacggc cattatctcc ccggatggcc gccaccttgc gccgcccttg 780
accgatgcag agggtctgct gctggccgat ttggatttaa gcctgctgac gaaacgcaaa 840
cgtatgattg attctcttgg ccattatgcg cgcccggaac tgttacatct ggttattgat 900
ggtcgtgcga ccgccccgat ggtggcgtct gaaagctctt ttgagaatcg taatccgagt 960
cagaccgcat cgcctcgcag caactccgat ggccatcatg ataacgcgag cagtgaccgc 1020
gacccggatc agcgggtggc cgtcctccgc tctcaggcct cc 1062

<210> SEQ ID NO 69
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 69

Met Glu Asn Lys Thr Val Leu Arg Ala Ala Ala Val Gln Leu Gly Pro
1 5 10 15

Asp Leu Thr Ser Lys Glu Arg Thr Ile Ala Lys Leu Ile Glu Ala Ile
20 25 30

His Glu Ala Ala Gly Lys Gly Ala Glu Leu Ala Val Phe Pro Glu Thr
35 40 45

Phe Val Pro Trp Tyr Pro Tyr Trp Ser Trp Val Met Pro Pro Leu Leu

```
    50                  55                  60

Thr Gly Lys Glu His Ile Arg Leu Tyr Asp Glu Ala Val Thr Val Pro
65                  70                  75                  80

Ser Ala Ala Thr Asp Gly Ile Ala Ser Ala Ala Lys Gln His Gly Ile
                85                  90                  95

Val Val Val Leu Gly Leu Asn Asp Arg Glu His Gly Thr Leu Tyr Asn
            100                 105                 110

Thr Gln Val Val Phe Asn Ala Asp Gly Thr Val Val Leu Arg Arg Arg
        115                 120                 125

Lys Val Thr Pro Thr Tyr His Glu Lys Ile Val Trp Ala Gln Gly Glu
    130                 135                 140

Gly Ser Gly Leu Thr Val Val Asp Thr His Ile Ala Arg Ile Gly Ala
145                 150                 155                 160

Leu Ala Cys Trp Glu His Tyr Asn Pro Leu Ala Arg Tyr Ala Met Ile
                165                 170                 175

Ala Gln His Glu Asp Ile His Val Ala Gln Phe Pro Ala Ser Ile Met
            180                 185                 190

Gly Pro Met Phe Ala Glu Gln Ile Glu Leu Thr Leu Arg His His Ala
        195                 200                 205

Leu Glu Ser Ala Cys Phe Val Val Asn Ala Thr Ala Trp Leu Ser Asp
    210                 215                 220

Glu Gln Met Ala Ser Val Ser Pro Glu Gln Gln Leu Gln Arg Ala Leu
225                 230                 235                 240

Arg Gly Ala Cys Met Thr Ala Ile Ile Ser Pro Asp Gly Arg His Leu
                245                 250                 255

Ala Pro Pro Leu Thr Asp Ala Glu Gly Leu Leu Leu Ala Asp Leu Asp
            260                 265                 270

Leu Ser Leu Leu Thr Lys Arg Lys Arg Met Ile Asp Ser Leu Gly His
        275                 280                 285

Tyr Ala Arg Pro Glu Leu Leu His Leu Val Ile Asp Gly Arg Ala Thr
    290                 295                 300

Ala Pro Met Val Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
            340                 345                 350

Ala Ser
```

<210> SEQ ID NO 70
<211> LENGTH: 996
<212> TYPE: DNA
<213> ORGANISM: Artificial sequence
<220> FEATURE:
<223> OTHER INFORMATION: codon modified sequence

<400> SEQUENCE: 70

```
atgactacga ttaaagtggc cgcggcgcag atccgtccgg ttgtgttttc actggatggt      60

agcttgcaaa aaattattga tgccatggcc gaggcggccg ctcagggggt ggaacttatt     120

gtgtttccag aaaccttttt accatattat ccgtattttt cttttgttga gccacctgtc     180

ctcctgggtc gcagtcacct ggcgctttat gataacgcgc tggtgatccc ggggccgctg     240

accgatgccg ttgccgcggc ggcgtctcag tacggcattc aggtgctggt gggcgtgaac     300

gaaaaagatg gtggtaccgt gtacaatacc cagctgctgt tcaatagctg cggtgatctg     360
```

```
gtgctgaaac ggcgtaaaat taccccgacc tatcatgaac gcatgctgtg ggcacaaggt    420

gatggctccg gcatcaaggt ggttcagacg ccgttaggcc gcgtgggtgc actggcgtgc    480

tgggaacatt ataacccgtt agcaaaatat gcgctgatgg cgaatggcga ggaaattcat    540

tgtgcgcagt ttccggccag cctggttggt ccgatcttta cggaacagac ggcgttgacc    600

atgcgccatc atgcggtcga agcaggctgt ttcgtcatct gctcgaccgc ctggctgcat    660

ccggacgaat acgcctcggt gaccagcgac tcgggtttac ataaagcgta tcaaggcggc    720

tgccatacag ccgtgatctc accggatggc cgctacctgg caggccctct gccggatggc    780

gaaggcctcg ccattgcgga tcttgatctg gccctgatta ctaaacgtaa acgtatgatg    840

gatagcctgg ggcactatag ccgcccggaa ttgttaagtc tgaacattaa cagcagccca    900

gcagtaccgg tccagaacat gtcttccgcg accgttcccc tggaaccggc tacggcgacc    960

gacgcgttga gttccatgga agcgttgaac cacgtt                              996
```

<210> SEQ ID NO 71
<211> LENGTH: 332
<212> TYPE: PRT
<213> ORGANISM: Artificial sequence
<220> FEATURE:
<223> OTHER INFORMATION: translated protein from codon modified sequence

<400> SEQUENCE: 71

```
Met Thr Thr Ile Lys Val Ala Ala Ala Gln Ile Arg Pro Val Val Phe
1               5                   10                  15

Ser Leu Asp Gly Ser Leu Gln Lys Ile Ile Asp Ala Met Ala Glu Ala
            20                  25                  30

Ala Ala Gln Gly Val Glu Leu Ile Val Phe Pro Glu Thr Phe Leu Pro
        35                  40                  45

Tyr Tyr Pro Tyr Phe Ser Phe Val Glu Pro Pro Val Leu Leu Gly Arg
    50                  55                  60

Ser His Leu Ala Leu Tyr Asp Asn Ala Leu Val Ile Pro Gly Pro Leu
65                  70                  75                  80

Thr Asp Ala Val Ala Ala Ala Ala Ser Gln Tyr Gly Ile Gln Val Leu
                85                  90                  95

Val Gly Val Asn Glu Lys Asp Gly Gly Thr Val Tyr Asn Thr Gln Leu
            100                 105                 110

Leu Phe Asn Ser Cys Gly Asp Leu Val Leu Lys Arg Arg Lys Ile Thr
        115                 120                 125

Pro Thr Tyr His Glu Arg Met Leu Trp Ala Gln Gly Asp Gly Ser Gly
    130                 135                 140

Ile Lys Val Val Gln Thr Pro Leu Gly Arg Val Gly Ala Leu Ala Cys
145                 150                 155                 160

Trp Glu His Tyr Asn Pro Leu Ala Lys Tyr Ala Leu Met Ala Asn Gly
                165                 170                 175

Glu Glu Ile His Cys Ala Gln Phe Pro Ala Ser Leu Val Gly Pro Ile
            180                 185                 190

Phe Thr Glu Gln Thr Ala Leu Thr Met Arg His His Ala Val Glu Ala
        195                 200                 205

Gly Cys Phe Val Ile Cys Ser Thr Ala Trp Leu His Pro Asp Glu Tyr
    210                 215                 220

Ala Ser Val Thr Ser Asp Ser Gly Leu His Lys Ala Tyr Gln Gly Gly
225                 230                 235                 240

Cys His Thr Ala Val Ile Ser Pro Asp Gly Arg Tyr Leu Ala Gly Pro
```

245                 250                 255

Leu Pro Asp Gly Glu Gly Leu Ala Ile Ala Asp Leu Asp Leu Ala Leu
            260                 265                 270

Ile Thr Lys Arg Lys Arg Met Met Asp Ser Leu Gly His Tyr Ser Arg
        275                 280                 285

Pro Glu Leu Leu Ser Leu Asn Ile Asn Ser Ser Pro Ala Val Pro Val
    290                 295                 300

Gln Asn Met Ser Ser Ala Thr Val Pro Leu Glu Pro Ala Thr Ala Thr
305                 310                 315                 320

Asp Ala Leu Ser Ser Met Glu Ala Leu Asn His Val
                325                 330

<210> SEQ ID NO 72
<211> LENGTH: 996
<212> TYPE: DNA
<213> ORGANISM: Artificial sequence
<220> FEATURE:
<223> OTHER INFORMATION: codon modified sequence

<400> SEQUENCE: 72
atgtctacca tgaaagttgc agcggcgcaa atccgccctg tgttgtttag cgtggaggcc 60
tcgctccaga aaatgttaga tgccatgggc gaagcggcgg caaacggtgt ggaattaatt 120
gtgttcccag aaacctggct tccgtactat ccattttgga gcttcttgga gccgcccatt 180
ctgatgggtc gtagtcacct tgcactgtat gaaaacgcgg tcgtgatgcc gggtccggta 240
acggatgcgg tggccgcggc cgcttcgcag tatgcaatgc aggttttggt tggcgttaat 300
gaacgtgatg cagccactat ttacaacacc cagctgctgt ttaacagctg tggcgaactg 360
attgtccgtc gccgtaaact gacgccgacc taccatgaaa aagtcctgtg gggtcagggg 420
gatggctctg gtgtgaaggt ggtgcagtcc ccgctggcgc gggttggcgc ggtcgcgtgc 480
tgggaacatt ggaatccatt agcgcgctat gcccttatgg cgcaaggcga agaaattcat 540
tgtgcgcagt ttccgggtac ggttgtgggc ccgatttata ccgataacac cgccgtcacc 600
atccgccatc atgccgtgga ggccgggtgc tttgtgatct gctctaccgg ctggctgcat 660
ccggaagact atgcgtccat tagttcggat tccggcatgc accgtggctt tcagggcggt 720
tgccataccg ccgtgattag ccctgaaggc cgctttctgg cgggcccact gccggatggt 780
gaaggattag cgctggctga cctggacttg gcgctgatca cgaaacgcaa acgtgtgctg 840
gattcggttg cccactattc tcgcccggaa ctcctgagcc tgaacatcaa cagcagtccg 900
gcggtgccgg tacagaacat gagcacggcg agtgtgccgc tggaaccggc gaccgccact 960
gatgcactct ccagcatgga agcgctgaat catgtt 996

<210> SEQ ID NO 73
<211> LENGTH: 332
<212> TYPE: PRT
<213> ORGANISM: Artificial sequence
<220> FEATURE:
<223> OTHER INFORMATION: translated protein from codon modified sequence

<400> SEQUENCE: 73

Met Ser Thr Met Lys Val Ala Ala Ala Gln Ile Arg Pro Val Leu Phe
1               5                   10                  15

Ser Val Glu Ala Ser Leu Gln Lys Met Leu Asp Ala Met Gly Glu Ala
            20                  25                  30

Ala Ala Asn Gly Val Glu Leu Ile Val Phe Pro Glu Thr Trp Leu Pro
        35                  40                  45

Tyr Tyr Pro Phe Trp Ser Phe Leu Glu Pro Pro Ile Leu Met Gly Arg
    50                  55                  60

Ser His Leu Ala Leu Tyr Glu Asn Ala Val Val Met Pro Gly Pro Val
65                  70                  75                  80

Thr Asp Ala Val Ala Ala Ala Ala Ser Gln Tyr Ala Met Gln Val Leu
                85                  90                  95

Val Gly Val Asn Glu Arg Asp Ala Ala Thr Ile Tyr Asn Thr Gln Leu
            100                 105                 110

Leu Phe Asn Ser Cys Gly Glu Leu Ile Val Arg Arg Arg Lys Leu Thr
        115                 120                 125

Pro Thr Tyr His Glu Lys Val Leu Trp Gly Gln Gly Asp Gly Ser Gly
    130                 135                 140

Val Lys Val Val Gln Ser Pro Leu Ala Arg Val Gly Ala Val Ala Cys
145                 150                 155                 160

Trp Glu His Trp Asn Pro Leu Ala Arg Tyr Ala Leu Met Ala Gln Gly
                165                 170                 175

Glu Glu Ile His Cys Ala Gln Phe Pro Gly Thr Val Val Gly Pro Ile
            180                 185                 190

Tyr Thr Asp Asn Thr Ala Val Thr Ile Arg His His Ala Val Glu Ala
        195                 200                 205

Gly Cys Phe Val Ile Cys Ser Thr Gly Trp Leu His Pro Glu Asp Tyr
    210                 215                 220

Ala Ser Ile Ser Ser Asp Ser Gly Met His Arg Gly Phe Gln Gly Gly
225                 230                 235                 240

Cys His Thr Ala Val Ile Ser Pro Glu Gly Arg Phe Leu Ala Gly Pro
                245                 250                 255

Leu Pro Asp Gly Glu Gly Leu Ala Leu Ala Asp Leu Asp Leu Ala Leu
            260                 265                 270

Ile Thr Lys Arg Lys Arg Val Leu Asp Ser Val Ala His Tyr Ser Arg
        275                 280                 285

Pro Glu Leu Leu Ser Leu Asn Ile Asn Ser Ser Pro Ala Val Pro Val
    290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330

<210> SEQ ID NO 74
<211> LENGTH: 996
<212> TYPE: DNA
<213> ORGANISM: Artificial sequence
<220> FEATURE:
<223> OTHER INFORMATION: codon modified sequence

<400> SEQUENCE: 74
atgtccacca tgaaagtggc ggcggcccag atgcgcccgg tcgtgtttag cgtagaagca 60
tctctgcaaa aaatcgtgga tgccatggcc gaagctgcgg cgcagggcgt cgaactcatt 120
gtgtttccag aaaccttttt accatattat ccgtggtttt cttttattga gccgccggtg 180
ctgatcgcta aaagccatat ggccctgtac gaacaggcgg ttgtgttgcc gggtccgctt 240
accgacgccg tcgcagcggc cgccagtcag tttggtatcc aagtgcttct gggtgttaat 300
gaacgtgatg gtgcttcggt gtataacact caggtcctgt tccaaagctg cggcgaaatt 360
attctgcgtc gtcgcaagct gacgcctacc tatcacgaaa aattaatttg ggcgcagggg 420
gatggctccg gtattaaatt ggtgcagacc ccgctggcac gtgtgggcgc gatggcgtgc 480
tgggagcatt ggaacccgtt agcaaaatac gcgatggttg cgaatggaga agaaattcac 540
tgcgcacagt ttccaggtag cctgctgggc ccgatctatt ctgagaacac ggcgatgacg 600
ctgcgccatc atgccatcga agccggctgc ttcgttattt gtagcacggg ttggctgcat 660
cccgaagatt tcgcgtcgtt gaccaccgac tcaggcattc ataaagcgtg gcagggtggc 720
tgtcacacgg gcgttattag cccggatggg aaatatttgg cgggcccact tcctgacgcg 780
gaaggcgtgg cgattgccga tttagatctg gcgatgatta gtcgccgcaa acgcctggtg 840
gattcagtgg gccattatag tcggccggaa ctgctgagcc tgcagatcaa caccacaccg 900
gcggttccgg tgcagaacat gtccaccgcg accgttccgc tcgaaccggc caccgccact 960
gatgcactgt cgagcatgga agcgctgaac catgtg 996

<210> SEQ ID NO 75
<211> LENGTH: 332
<212> TYPE: PRT
<213> ORGANISM: Artificial sequence
<220> FEATURE:
<223> OTHER INFORMATION: translated protein from codon modified sequence

<400> SEQUENCE: 75

Met Ser Thr Met Lys Val Ala Ala Ala Gln Met Arg Pro Val Val Phe
1 5 10 15

Ser Val Glu Ala Ser Leu Gln Lys Ile Val Asp Ala Met Ala Glu Ala
20 25 30

Ala Ala Gln Gly Val Glu Leu Ile Val Phe Pro Glu Thr Phe Leu Pro
35 40 45

Tyr Tyr Pro Trp Phe Ser Phe Ile Glu Pro Pro Val Leu Ile Ala Lys
50 55 60

Ser His Met Ala Leu Tyr Glu Gln Ala Val Val Leu Pro Gly Pro Leu
65 70 75 80

Thr Asp Ala Val Ala Ala Ala Ala Ser Gln Phe Gly Ile Gln Val Leu
85 90 95

Leu Gly Val Asn Glu Arg Asp Gly Ala Ser Val Tyr Asn Thr Gln Val
100 105 110

Leu Phe Gln Ser Cys Gly Glu Ile Ile Leu Arg Arg Arg Lys Leu Thr
115 120 125

Pro Thr Tyr His Glu Lys Leu Ile Trp Ala Gln Gly Asp Gly Ser Gly
130 135 140

Ile Lys Leu Val Gln Thr Pro Leu Ala Arg Val Gly Ala Met Ala Cys
145 150 155 160

Trp Glu His Trp Asn Pro Leu Ala Lys Tyr Ala Met Val Ala Asn Gly
165 170 175

Glu Glu Ile His Cys Ala Gln Phe Pro Gly Ser Leu Leu Gly Pro Ile
180 185 190

Tyr Ser Glu Asn Thr Ala Met Thr Leu Arg His His Ala Ile Glu Ala
195 200 205

Gly Cys Phe Val Ile Cys Ser Thr Gly Trp Leu His Pro Glu Asp Phe
210 215 220

Ala Ser Leu Thr Thr Asp Ser Gly Ile His Lys Ala Trp Gln Gly Gly
225 230 235 240

Cys His Thr Gly Val Ile Ser Pro Asp Gly Lys Tyr Leu Ala Gly Pro
245 250 255

Leu Pro Asp Ala Glu Gly Val Ala Ile Ala Asp Leu Asp Leu Ala Met

```
            260                 265                 270

Ile Ser Arg Arg Lys Arg Leu Val Asp Ser Val Gly His Tyr Ser Arg
        275                 280                 285

Pro Glu Leu Leu Ser Leu Gln Ile Asn Thr Thr Pro Ala Val Pro Val
    290                 295                 300

Gln Asn Met Ser Thr Ala Thr Val Pro Leu Glu Pro Ala Thr Ala Thr
305                 310                 315                 320

Asp Ala Leu Ser Ser Met Glu Ala Leu Asn His Val
                325                 330
```

<210> SEQ ID NO 76
<211> LENGTH: 999
<212> TYPE: DNA
<213> ORGANISM: Artificial sequence
<220> FEATURE:
<223> OTHER INFORMATION: codon modified sequence

<400> SEQUENCE: 76

```
atggccgagt cccgcattat ccgtgcggcg gccgcgcagt tggcgccgga tattcatgaa     60

gccagtcgta ccctcgcgcg cgtgttagag gcgattgatg aagcagcgga aaaaggtgcg    120

gaaattatcg tgtttcctga aacatggctg ccgtattacc cgtttttttc ctttatgacg    180

ccggccgtta ctgcgggcgc ggcccatttg aagatgtatg atcaggctgt ggttattcca    240

ggcgccatca cgcatggtgt cagtgaacgc gcgcgccttc gtaatatcgt ggtggtcctg    300

ggagtgaacg aaaaagatca cggcacctta tataacaccc aggtggtttt tgatgcctcg    360

ggtgaactgc tgctgaaacg ccgtaaatta accccgacgt accacgaacg catgatctgg    420

ggtcaagggg atggcgccgg cctgaaaacc gttgccaccc gtgtgggcca ggtgggcgca    480

ttagcctgct gggaacattg gaatccgctg gcgcgctatt ccctgatggc gcagcacgag    540

gaaatccatt gcagccagtt tccgggctct atcatgggcc cgattttcgc tgaacagatg    600

gaaattaccc ttcggcatca tgcgttggag agcggttgct tcgtcattaa cgcaaccggt    660

tggctgagcg aacaacagat taacgacatc accacggatc cagccctgca aaaaggcatt    720

cgtggtggct gtcatacggc gattatttct ccggatgggc gtcatctggt gccgccgctg    780

accgaaggcg aagcgctgct ggtggcggac atggatattg cactgattac taaacgcaaa    840

cgtatgatgg attctttggg ccactatgcg cgccctgaac tgctgtcgct gcagctcgaa    900

gacaccccaa gccgctatat ggttacccgc catgcagaca tgcatacgga aggtgaacgg    960

gatgcagaaa gctcggtaca gagcagtgcg accgattat                           999
```

<210> SEQ ID NO 77
<211> LENGTH: 333
<212> TYPE: PRT
<213> ORGANISM: Artificial sequence
<220> FEATURE:
<223> OTHER INFORMATION: translated protein from codon modified sequence

<400> SEQUENCE: 77

```
Met Ala Glu Ser Arg Ile Ile Arg Ala Ala Ala Ala Gln Leu Ala Pro
1               5                   10                  15

Asp Ile His Glu Ala Ser Arg Thr Leu Ala Arg Val Leu Glu Ala Ile
            20                  25                  30

Asp Glu Ala Ala Glu Lys Gly Ala Glu Ile Ile Val Phe Pro Glu Thr
        35                  40                  45

Trp Leu Pro Tyr Tyr Pro Phe Phe Ser Phe Met Thr Pro Ala Val Thr
    50                  55                  60
```

```
Ala Gly Ala Ala His Leu Lys Met Tyr Asp Gln Ala Val Val Ile Pro
65                  70                  75                  80

Gly Ala Ile Thr His Gly Val Ser Glu Arg Ala Arg Leu Arg Asn Ile
                85                  90                  95

Val Val Val Leu Gly Val Asn Glu Lys Asp His Gly Thr Leu Tyr Asn
            100                 105                 110

Thr Gln Val Val Phe Asp Ala Ser Gly Glu Leu Leu Leu Lys Arg Arg
        115                 120                 125

Lys Leu Thr Pro Thr Tyr His Glu Arg Met Ile Trp Gly Gln Gly Asp
    130                 135                 140

Gly Ala Gly Leu Lys Thr Val Ala Thr Arg Val Gly Gln Val Gly Ala
145                 150                 155                 160

Leu Ala Cys Trp Glu His Trp Asn Pro Leu Ala Arg Tyr Ser Leu Met
                165                 170                 175

Ala Gln His Glu Glu Ile His Cys Ser Gln Phe Pro Gly Ser Ile Met
            180                 185                 190

Gly Pro Ile Phe Ala Glu Gln Met Glu Ile Thr Leu Arg His His Ala
        195                 200                 205

Leu Glu Ser Gly Cys Phe Val Ile Asn Ala Thr Gly Trp Leu Ser Glu
    210                 215                 220

Gln Gln Ile Asn Asp Ile Thr Thr Asp Pro Ala Leu Gln Lys Gly Ile
225                 230                 235                 240

Arg Gly Gly Cys His Thr Ala Ile Ile Ser Pro Asp Gly Arg His Leu
                245                 250                 255

Val Pro Pro Leu Thr Glu Gly Glu Ala Leu Leu Val Ala Asp Met Asp
            260                 265                 270

Ile Ala Leu Ile Thr Lys Arg Lys Arg Met Met Asp Ser Leu Gly His
        275                 280                 285

Tyr Ala Arg Pro Glu Leu Leu Ser Leu Gln Leu Glu Asp Thr Pro Ser
    290                 295                 300

Arg Tyr Met Val Thr Arg His Ala Asp Met His Thr Glu Gly Glu Arg
305                 310                 315                 320

Asp Ala Glu Ser Ser Val Gln Ser Ser Ala Thr Asp Tyr
                325                 330
```

<210> SEQ ID NO 78
<211> LENGTH: 999
<212> TYPE: DNA
<213> ORGANISM: Artificial sequence
<220> FEATURE:
<223> OTHER INFORMATION: codon modified sequence

<400> SEQUENCE: 78

```
atggcggaaa gccgtattat tcgcgccgcg gccgctcagt tagcgcctga tatgcacgaa     60

gcgagcaaaa cgctggcgaa ggtcattgat gcaattgagg aagctgcaga taaaggtgca    120

gaaattatcg tttttccgga gaccttcgtg ccgtactacc cgtactggac ttatatttct    180

ccggccatga ccgccggcgc ggcgcatctc aagttgtatg aacaggcgat tgtggtgccg    240

ggggcgctga cgcacgcggt ttccgagaaa gcgcgcttac gtaacgtggt ggttgtcatt    300

ggcctgaacg aacgcgaaca tggcaccctg tataataccc agcttgtgtt tgaggcgtcg    360

ggcgatctgt tgctgaaacg ccggaaactg actccgagtt ggcatgaacg tatcatctgg    420

ggccaaggtg atggagcagg ccttaaaacc gtggcgacga aatcggtcaa ggttggcgcc    480

attgcctgtt gggaacatta taaccctctg gcgcggtaca ccctggtcgc gcagcacgaa    540
```

```
gaaattcatt gctctaacta tccggggagt ttactgggcc cgctctatgc ggaacagatg    600

gagctgaccc tgcgtcatca tgcactggaa agtggctgct ttgtgattaa tgccaccggt    660

tggctgaccg aacagcagat taacgaaatg accacggatc cggccctgca aaaagcggtt    720

cgcggcggtt gccataccgc cattatttct ccagaaggca aacatcttgt gccaccactg    780

acagatggtg aaggtatctt gatggccgac atggatgtgg cactgatcac gcgccgtaaa    840

cgtatggtag actccatcgc ccattatgcg cgcccggaac tgttgtcctt aaacctggat    900

gatagcccgt cgcgctatat gatcacgcgt catgcggata tgcacaccga aggcgaacgc    960

gatgcggaaa gcagcgtgca gtcgagcgcc accgactat                           999


<210> SEQ ID NO 79
<211> LENGTH: 333
<212> TYPE: PRT
<213> ORGANISM: Artificial sequence
<220> FEATURE:
<223> OTHER INFORMATION: translated protein from codon modified sequence

<400> SEQUENCE: 79

Met Ala Glu Ser Arg Ile Ile Arg Ala Ala Ala Ala Gln Leu Ala Pro
1               5                   10                  15

Asp Met His Glu Ala Ser Lys Thr Leu Ala Lys Val Ile Asp Ala Ile
            20                  25                  30

Glu Glu Ala Ala Asp Lys Gly Ala Glu Ile Ile Val Phe Pro Glu Thr
        35                  40                  45

Phe Val Pro Tyr Tyr Pro Tyr Trp Thr Tyr Ile Ser Pro Ala Met Thr
    50                  55                  60

Ala Gly Ala Ala His Leu Lys Leu Tyr Glu Gln Ala Ile Val Val Pro
65                  70                  75                  80

Gly Ala Leu Thr His Ala Val Ser Glu Lys Ala Arg Leu Arg Asn Val
                85                  90                  95

Val Val Val Ile Gly Leu Asn Glu Arg Glu His Gly Thr Leu Tyr Asn
            100                 105                 110

Thr Gln Leu Val Phe Glu Ala Ser Gly Asp Leu Leu Leu Lys Arg Arg
        115                 120                 125

Lys Leu Thr Pro Ser Trp His Glu Arg Ile Ile Trp Gly Gln Gly Asp
    130                 135                 140

Gly Ala Gly Leu Lys Thr Val Ala Thr Lys Ile Gly Gln Val Gly Ala
145                 150                 155                 160

Ile Ala Cys Trp Glu His Tyr Asn Pro Leu Ala Arg Tyr Thr Leu Val
                165                 170                 175

Ala Gln His Glu Glu Ile His Cys Ser Asn Tyr Pro Gly Ser Leu Leu
            180                 185                 190

Gly Pro Leu Tyr Ala Glu Gln Met Glu Leu Thr Leu Arg His His Ala
        195                 200                 205

Leu Glu Ser Gly Cys Phe Val Ile Asn Ala Thr Gly Trp Leu Thr Glu
    210                 215                 220

Gln Gln Ile Asn Glu Met Thr Thr Asp Pro Ala Leu Gln Lys Ala Val
225                 230                 235                 240

Arg Gly Gly Cys His Thr Ala Ile Ile Ser Pro Glu Gly Lys His Leu
                245                 250                 255

Val Pro Pro Leu Thr Asp Gly Glu Gly Ile Leu Met Ala Asp Met Asp
            260                 265                 270

Val Ala Leu Ile Thr Arg Arg Lys Arg Met Val Asp Ser Ile Ala His
```

```
        275                 280                 285

Tyr Ala Arg Pro Glu Leu Leu Ser Leu Asn Leu Asp Asp Ser Pro Ser
    290                 295                 300

Arg Tyr Met Ile Thr Arg His Ala Asp Met His Thr Glu Gly Glu Arg
305                 310                 315                 320

Asp Ala Glu Ser Ser Val Gln Ser Ser Ala Thr Asp Tyr
                325                 330


<210> SEQ ID NO 80
<211> LENGTH: 999
<212> TYPE: DNA
<213> ORGANISM: Artificial sequence
<220> FEATURE:
<223> OTHER INFORMATION: codon modified sequence

<400> SEQUENCE: 80

atggccgaaa gccgtatgat tcgcgccgcc gcggcccaaa ttgcgccgga tctccacgaa      60

gcgaccaaaa ccgtcgccaa acttattgag gcgatcgaag aagccggcga taaaggcgcg     120

gagattatcg tctttccaga aacgttctta ccgtattatc cgtggtggac ctttatcacc     180

ccgggcatta cggcgggtgc ggctcatgtg aagatttatg aaaacgcggt tgttctgccg     240

ggtgcagtta cccatgcagt gagtgagaaa gccaaactgc gcaacatttt agtagttgtt     300

ggcttgaatg aaaaagacca cggcacgctg tataacaccc aggtcgtgtt tgaagccagt     360

ggcgagctgc tgctcaagcg ccgtaaaatt actccgactt ttcatgaacg catgatttgg     420

ggccaggggg atggagcggg cgtgcgcact gtggcatcgc gggtgggtca agttggtgct     480

ttagcgtgct gggaacattg gaaccctctg gcgcgttact cgttactggg caatcatgag     540

gaaattcatt gctctcagtg gccgggttcg ctgcttggtc cgatgtttgc ggatcagttg     600

gaagtgaccg tgcgccatca cgcgttggaa agcggctgtt tcgtgatcaa cgccaccgcc     660

tggttgacag aaaacaacat gaatgatgtc accaccgatc cagcagtgca gaaagcgatg     720

cgcggcggct gccatacggc aatcattagt ccggaaggca aacatctggt gccgccactg     780

accgatgggg aaggtattct gatcgcggat atggatctgg cggtgattac gcgtcgcaaa     840

aaaatcgtgg acagcctggc gcactatgcg cgtccggaac tgctgtccct gcagctggaa     900

gaatccccta gcaaatatat gattacccgt catgcagata tgcatacgga aggtgaacgc     960

gacgcggaaa gctctgttca gtccagcgcc accgattac                            999


<210> SEQ ID NO 81
<211> LENGTH: 333
<212> TYPE: PRT
<213> ORGANISM: Artificial sequence
<220> FEATURE:
<223> OTHER INFORMATION: translated protein from codon modified sequence

<400> SEQUENCE: 81

Met Ala Glu Ser Arg Met Ile Arg Ala Ala Ala Ala Gln Ile Ala Pro
1               5                   10                  15

Asp Leu His Glu Ala Thr Lys Thr Val Ala Lys Leu Ile Glu Ala Ile
            20                  25                  30

Glu Glu Ala Gly Asp Lys Gly Ala Glu Ile Ile Val Phe Pro Glu Thr
        35                  40                  45

Phe Leu Pro Tyr Tyr Pro Trp Trp Thr Phe Ile Thr Pro Gly Ile Thr
    50                  55                  60

Ala Gly Ala Ala His Val Lys Ile Tyr Glu Asn Ala Val Val Leu Pro
65                  70                  75                  80
```

```
Gly Ala Val Thr His Ala Val Ser Glu Lys Ala Lys Leu Arg Asn Ile
                85                  90                  95

Leu Val Val Val Gly Leu Asn Glu Lys Asp His Gly Thr Leu Tyr Asn
            100                 105                 110

Thr Gln Val Val Phe Glu Ala Ser Gly Glu Leu Leu Leu Lys Arg Arg
        115                 120                 125

Lys Ile Thr Pro Thr Phe His Glu Arg Met Ile Trp Gly Gln Gly Asp
    130                 135                 140

Gly Ala Gly Val Arg Thr Val Ala Ser Arg Val Gly Gln Val Gly Ala
145                 150                 155                 160

Leu Ala Cys Trp Glu His Trp Asn Pro Leu Ala Arg Tyr Ser Leu Leu
                165                 170                 175

Gly Asn His Glu Glu Ile His Cys Ser Gln Trp Pro Gly Ser Leu Leu
            180                 185                 190

Gly Pro Met Phe Ala Asp Gln Leu Glu Val Thr Val Arg His His Ala
        195                 200                 205

Leu Glu Ser Gly Cys Phe Val Ile Asn Ala Thr Ala Trp Leu Thr Glu
    210                 215                 220

Asn Asn Met Asn Asp Val Thr Thr Asp Pro Ala Val Gln Lys Ala Met
225                 230                 235                 240

Arg Gly Gly Cys His Thr Ala Ile Ile Ser Pro Glu Gly Lys His Leu
                245                 250                 255

Val Pro Pro Leu Thr Asp Gly Glu Gly Ile Leu Ile Ala Asp Met Asp
            260                 265                 270

Leu Ala Val Ile Thr Arg Arg Lys Lys Ile Val Asp Ser Leu Ala His
        275                 280                 285

Tyr Ala Arg Pro Glu Leu Leu Ser Leu Gln Leu Glu Glu Ser Pro Ser
    290                 295                 300

Lys Tyr Met Ile Thr Arg His Ala Asp Met His Thr Glu Gly Glu Arg
305                 310                 315                 320

Asp Ala Glu Ser Ser Val Gln Ser Ser Ala Thr Asp Tyr
                325                 330
```

<210> SEQ ID NO 82
<211> LENGTH: 1062
<212> TYPE: DNA
<213> ORGANISM: Artificial sequence
<220> FEATURE:
<223> OTHER INFORMATION: codon modified sequence

<400> SEQUENCE: 82

```
atggaaaata aaagcattgt gcgcgccgcc gcggtgcaaa ttgccccgga cgtgacgtcg     60

cgcgagaaaa ccctggcacg tgttcttgaa gcgattcatg aagccgcagg caagggcgcg    120

gaactggcgg tttttccaga aacgtttgtc ccgtggtatc cgtatttttc atgggtgatt    180

ccaccgctgc tgtccggtcg cgaacatatc cggctgtatg atgaagcggt taccattcca    240

agcgcggcga ccgaagcgat tgccagtgcg gcccgccagc atggcattgt ggtggtgatg    300

ggcgtgaacg aacgcgaaca tggaaccatc tataacaccc aggtgatgtt taatgcggat    360

ggcaccttga ttctgcgccg tcgcaaaatt acccctacgt tccacgaacg tctgatttgg    420

ggtcagggcg atgcgagtgg catcacagta gttgaaagcc acgtggcgcg tattggtgcg    480

gtggcgtgct gggaacatta taatccaatt gcaaaatacg cgctcgtcgc ccagcatgaa    540

gaaattcacg tcgcgcagtg gccggcaagc atgattggcc cgatctttgc cgaaaacatt    600
```

```
gatgtgacta tccgccacca tgccctggaa agtgcgtgct tcgttgtcaa cgcaaccggg    660

tggttaactg atgaccagat cgcctccatg accccggata acaacttgca gaaagcgctg    720

cgcgggggtt gtatgacggc catcatctcc ccggagggta aacatctggc cccgcccctg    780

accgaaggtg agggcgtttt actggcggat ctggatatgt cccttatcac caaacggaaa    840

cgcatgatgg actcggtggg ccattacgct cgtccggaac tgttgcattt actcattgat    900

ggccgtgcaa cggcgccgat ggtggcgagt gagtctagct atgaaaaccg taatccgtct    960

cagaccgcgt cgcctcgcag caactctgac ggtcatcatg ataacgctag cagcgatcgc   1020

gatccggatc aacgtgttgc agtgctgcgt tctcaggcct cg                      1062
```

```
<210> SEQ ID NO 83
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 83

Met Glu Asn Lys Ser Ile Val Arg Ala Ala Ala Val Gln Ile Ala Pro
1               5                   10                  15

Asp Val Thr Ser Arg Glu Lys Thr Leu Ala Arg Val Leu Glu Ala Ile
            20                  25                  30

His Glu Ala Ala Gly Lys Gly Ala Glu Leu Ala Val Phe Pro Glu Thr
        35                  40                  45

Phe Val Pro Trp Tyr Pro Tyr Phe Ser Trp Val Ile Pro Pro Leu Leu
    50                  55                  60

Ser Gly Arg Glu His Ile Arg Leu Tyr Asp Glu Ala Val Thr Ile Pro
65                  70                  75                  80

Ser Ala Ala Thr Glu Ala Ile Ala Ser Ala Ala Arg Gln His Gly Ile
                85                  90                  95

Val Val Val Met Gly Val Asn Glu Arg Glu His Gly Thr Ile Tyr Asn
            100                 105                 110

Thr Gln Val Met Phe Asn Ala Asp Gly Thr Leu Ile Leu Arg Arg Arg
        115                 120                 125

Lys Ile Thr Pro Thr Phe His Glu Arg Leu Ile Trp Gly Gln Gly Asp
    130                 135                 140

Ala Ser Gly Ile Thr Val Val Glu Ser His Val Ala Arg Ile Gly Ala
145                 150                 155                 160

Val Ala Cys Trp Glu His Tyr Asn Pro Ile Ala Lys Tyr Ala Leu Val
                165                 170                 175

Ala Gln His Glu Glu Ile His Val Ala Gln Trp Pro Ala Ser Met Ile
            180                 185                 190

Gly Pro Ile Phe Ala Glu Asn Ile Asp Val Thr Ile Arg His His Ala
        195                 200                 205

Leu Glu Ser Ala Cys Phe Val Val Asn Ala Thr Gly Trp Leu Thr Asp
    210                 215                 220

Asp Gln Ile Ala Ser Met Thr Pro Asp Asn Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Leu Thr Glu Gly Glu Gly Val Leu Leu Ala Asp Leu Asp
            260                 265                 270

Met Ser Leu Ile Thr Lys Arg Lys Arg Met Met Asp Ser Val Gly His
        275                 280                 285
```

Tyr Ala Arg Pro Glu Leu Leu His Leu Leu Ile Asp Gly Arg Ala Thr
    290                 295                 300

Ala Pro Met Val Ala Ser Glu Ser Ser Tyr Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
            340                 345                 350

Ala Ser

<210> SEQ ID NO 84
<211> LENGTH: 1062
<212> TYPE: DNA
<213> ORGANISM: Artificial sequence
<220> FEATURE:
<223> OTHER INFORMATION: codon modified sequence

<400> SEQUENCE: 84
atggagaata aaaccgtgat tcgcgcggcc gcggtccaga ttgcgccgga tctcacgtcg 60
cgcgataaga ctctggccaa aatcgtggaa gcgattcatg acgctgcggg taaaggcgcg 120
gaattagcgg tgtttccgga gaccttcgtc ccatggtatc cgttttggtc gtacgtgatc 180
ccgcctatcc tgtctgcccg tgatcatatt cgtatttacg atgaagctgt gtcgctgccg 240
agtgccgcca ccgaaggtat cgccactgca gcaaaaaatc atggtatcgt tgtggttgtt 300
ggtatcaacg agcgcgaaca cggcacggtg tataacaccc agattctttt taacgcggat 360
ggcacggtga tcttaaaacg tcgcaaaatt accccgacct tccatgaacg catgatttgg 420
ggcaacgggg atggcagcgg cctgacggta gtggaatctc acttagcacg gattggcgcc 480
attgcgtgct gggaacattg gaacccgctc gcgcgttatg ccgttatggc ccaacatgaa 540
gaaattcatg tggcgcagtt tcctgcctct atggtcgcgc caatttttgc agaacagatc 600
gaactgacca ttcgccatca tgcgctggaa agtggctgct ttgtggttaa tgcaaccggg 660
tggctgagcg aagagcagat ggcttccttg acaccagatc aacagattca gcgtgccctg 720
cgtggcggct gtatgaccgc aattattagc ccagacggta aacacctggc cccgccgctg 780
agtgaaggag aaggcatcct gatcgcggat ctggatctga gccttattac gaaacgtaaa 840
cggatgattg ataccgtggg tcactatgcg cgtccggaat tgctgcattt ggtcattgat 900
ggtaaagcga ccgcgccgat gatggcgagc gaaagcagct ttgaaaaccg caacccgagc 960
cagaccgcgt cgccgcgctc caactccgat ggccatcatg acaacgcgtc tagtgaccgc 1020
gatcccgatc aacgcgttgc ggtgctgcgc tcccaggcgt ca 1062

<210> SEQ ID NO 85
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 85

Met Glu Asn Lys Thr Val Ile Arg Ala Ala Ala Val Gln Ile Ala Pro
1               5                   10                  15

Asp Leu Thr Ser Arg Asp Lys Thr Leu Ala Lys Ile Val Glu Ala Ile
            20                  25                  30

His Asp Ala Ala Gly Lys Gly Ala Glu Leu Ala Val Phe Pro Glu Thr
        35                  40                  45

```
Phe Val Pro Trp Tyr Pro Phe Trp Ser Tyr Val Ile Pro Pro Ile Leu
    50                  55                  60

Ser Ala Arg Asp His Ile Arg Ile Tyr Asp Glu Ala Val Ser Leu Pro
65                  70                  75                  80

Ser Ala Ala Thr Glu Gly Ile Ala Thr Ala Ala Lys Asn His Gly Ile
                85                  90                  95

Val Val Val Val Gly Ile Asn Glu Arg Glu His Gly Thr Val Tyr Asn
            100                 105                 110

Thr Gln Ile Leu Phe Asn Ala Asp Gly Thr Val Ile Leu Lys Arg Arg
        115                 120                 125

Lys Ile Thr Pro Thr Phe His Glu Arg Met Ile Trp Gly Asn Gly Asp
    130                 135                 140

Gly Ser Gly Leu Thr Val Val Glu Ser His Leu Ala Arg Ile Gly Ala
145                 150                 155                 160

Ile Ala Cys Trp Glu His Trp Asn Pro Leu Ala Arg Tyr Ala Val Met
                165                 170                 175

Ala Gln His Glu Glu Ile His Val Ala Gln Phe Pro Ala Ser Met Val
            180                 185                 190

Ala Pro Ile Phe Ala Glu Gln Ile Glu Leu Thr Ile Arg His His Ala
        195                 200                 205

Leu Glu Ser Gly Cys Phe Val Val Asn Ala Thr Gly Trp Leu Ser Glu
    210                 215                 220

Glu Gln Met Ala Ser Leu Thr Pro Asp Gln Gln Ile Gln Arg Ala Leu
225                 230                 235                 240

Arg Gly Gly Cys Met Thr Ala Ile Ile Ser Pro Asp Gly Lys His Leu
                245                 250                 255

Ala Pro Pro Leu Ser Glu Gly Glu Gly Ile Leu Ile Ala Asp Leu Asp
            260                 265                 270

Leu Ser Leu Ile Thr Lys Arg Lys Arg Met Ile Asp Thr Val Gly His
        275                 280                 285

Tyr Ala Arg Pro Glu Leu Leu His Leu Val Ile Asp Gly Lys Ala Thr
    290                 295                 300

Ala Pro Met Met Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
            340                 345                 350

Ala Ser
```

```
<210> SEQ ID NO 86
<211> LENGTH: 1062
<212> TYPE: DNA
<213> ORGANISM: Artificial sequence
<220> FEATURE:
<223> OTHER INFORMATION: codon modified sequence

<400> SEQUENCE: 86

atggatcaaa aaactattat tcgtgccgcg gcggtgcaga ttggcccaga tgtcaccagc      60

aaagataaaa ccatcgcgcg tattatcgaa gcaattcatg aagccgcggc aaaaggcgcg     120

gagctggcag tctttcccga aacctttctg ccatggtatc cgttttggag cttcctgatt     180

ccgccaattc ttaccggccg tgatcacctg aaaatgtttg atgacgcgat tacaatgccg     240

tctgccgcca ccgatgcaat cggttcagcg gcccgcaacc atggcgtggt ggttgttatt     300
```

```
ggcgtgaacg aacgtgatca tggtaccatg tataataccc aggtggtgtt taacgccgaa    360

ggcaccgtgg ttctgaagcg tcgcaaagtg agccctacgt ttcatgaacg catcgtttgg    420

ggccagggtg aggggtcagg catcacggtg gtggaaaccc atgtgggccg cattggtgcg    480

ctcgcgtgct gggaacactg gaacccgctg gcgcgttacg cgctgatggc gaaccatgaa    540

gagattcatg tcgcccagtg gccgggttct gtggttgggc cgattttcgg tgaacaagta    600

gaagtcacta tgcgccatca tgcgattgaa tccggctgtt tcgttgttaa cgcaacggct    660

tatctgaccg acgaacagat cgcgaccctg actccggacc agaatattca gaaagcgctc    720

cggggtgcgt gcctgacggc gatcattagc ccggaaggcc gccacttggc cccgccgctg    780

acggaaggtg aaggcatcct ggtggccgac cttgatctgt cgttaatcac caaacgcaaa    840

cgcttaatgg atacgttagg gcactatgcg cgtccagaac tgctgcattt gctgattgat    900

ggccgtgctt cggccccgat gatggcgagc gaaagtagtt ttgagaatcg caacccttcc    960

caaaccgcct ctccgcgcag caactcggat ggtcatcatg ataacgcaag cagcgatcgt   1020

gatccggatc agcgggtggc cgtgttgcgc tcccaggcga gt                     1062

<210> SEQ ID NO 87
<211> LENGTH: 354
<212> TYPE: PRT
<213> ORGANISM: Artificial sequence
<220> FEATURE:
<223> OTHER INFORMATION: translated protein from codon modified sequence

<400> SEQUENCE: 87

Met Asp Gln Lys Thr Ile Ile Arg Ala Ala Ala Val Gln Ile Gly Pro
1               5                   10                  15

Asp Val Thr Ser Lys Asp Lys Thr Ile Ala Arg Ile Ile Glu Ala Ile
            20                  25                  30

His Glu Ala Ala Ala Lys Gly Ala Glu Leu Ala Val Phe Pro Glu Thr
        35                  40                  45

Phe Leu Pro Trp Tyr Pro Phe Trp Ser Phe Leu Ile Pro Pro Ile Leu
    50                  55                  60

Thr Gly Arg Asp His Leu Lys Met Phe Asp Asp Ala Ile Thr Met Pro
65                  70                  75                  80

Ser Ala Ala Thr Asp Ala Ile Gly Ser Ala Ala Arg Asn His Gly Val
                85                  90                  95

Val Val Val Ile Gly Val Asn Glu Arg Asp His Gly Thr Met Tyr Asn
            100                 105                 110

Thr Gln Val Val Phe Asn Ala Glu Gly Thr Val Val Leu Lys Arg Arg
        115                 120                 125

Lys Val Ser Pro Thr Phe His Glu Arg Ile Val Trp Gly Gln Gly Glu
    130                 135                 140

Gly Ser Gly Ile Thr Val Val Glu Thr His Val Gly Arg Ile Gly Ala
145                 150                 155                 160

Leu Ala Cys Trp Glu His Trp Asn Pro Leu Ala Arg Tyr Ala Leu Met
                165                 170                 175

Ala Asn His Glu Glu Ile His Val Ala Gln Trp Pro Gly Ser Val Val
            180                 185                 190

Gly Pro Ile Phe Gly Glu Gln Val Glu Val Thr Met Arg His His Ala
        195                 200                 205

Ile Glu Ser Gly Cys Phe Val Val Asn Ala Thr Ala Tyr Leu Thr Asp
    210                 215                 220
```

```
Glu Gln Ile Ala Thr Leu Thr Pro Asp Gln Asn Ile Gln Lys Ala Leu
225                 230                 235                 240

Arg Gly Ala Cys Leu Thr Ala Ile Ile Ser Pro Glu Gly Arg His Leu
                245                 250                 255

Ala Pro Pro Leu Thr Glu Gly Glu Gly Ile Leu Val Ala Asp Leu Asp
            260                 265                 270

Leu Ser Leu Ile Thr Lys Arg Lys Arg Leu Met Asp Thr Leu Gly His
        275                 280                 285

Tyr Ala Arg Pro Glu Leu Leu His Leu Leu Ile Asp Gly Arg Ala Ser
    290                 295                 300

Ala Pro Met Met Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
            340                 345                 350

Ala Ser
```

<210> SEQ ID NO 88
<211> LENGTH: 969
<212> TYPE: DNA
<213> ORGANISM: Artificial sequence
<220> FEATURE:
<223> OTHER INFORMATION: codon modified sequence

<400> SEQUENCE: 88

```
atgagccatt ccaccaacaa taatagtagt actgttgttc gggccgcggc ggtgcagatt      60

tccccggttc tgtactccaa agaaggcacc acgcaaaaaa ttctgaacac catccgcgaa     120

ctgggcaagc aaggcgtgca atttgcagtg tttccggaaa cctttattcc atattatccg     180

tatttcacct tcttacagcc accttatatg caggccgacc agcatctgaa agtcatggaa     240

gaggcggtaa cgctgccgtc ggcgtctacc gaagcgattg gtgaggcggc ccgcgaagca     300

ggcgtcgtgg tctctattgg ggtgaacgaa cgtgacggtg caagcatcta caacacgcag     360

ctgctgtttg atgccgacgg taccttgatt aatcgccgcc gtaaaattac tccgaccttt     420

catgaacgta tggtgtgggg tcagggcgat ggtagtggca tgcgtgcagt ggatacaaaa     480

ggcggacgca tcggccagtt agcgtgctgg gaacactgga acccgcttgc ccgctatgcc     540

ctcattgcgg atggtgaaca gattcacgca gcgatgtatc ctggctcgag cttcggcgag     600

ctgttcagcc agcagattga tgtgtctctg cgtcagcatg ccctggaaag cgccgctttt     660

gttgtctcgt cgaccggttt tctggatgcg gagcaacagg cgcaggttgt gaaagatacg     720

gggagcccga ttggtccaat tagtggcggc aactttaccg ccatcattgc gccggatggg     780

accatcatcg gtgaaccgat tcgtagcggc gaaggctttg tgatcgcgga tttggatttt     840

aaccttctgg ataaacgcaa acggttagtg gacattcgcg cgcattacaa ccgtccggaa     900

ctgctgagct tgctcatcga tcgcacgccg gcggaatatg tgcaggaagt gaacaaatcc     960

gtttctgaa                                                             969
```

<210> SEQ ID NO 89
<211> LENGTH: 323
<212> TYPE: PRT
<213> ORGANISM: Artificial sequence
<220> FEATURE:
<223> OTHER INFORMATION: translated protein from codon modified sequence

<400> SEQUENCE: 89

Met Ser His Ser Thr Asn Asn Asn Ser Ser Thr Val Val Arg Ala Ala
1 5 10 15

Ala Val Gln Ile Ser Pro Val Leu Tyr Ser Lys Glu Gly Thr Thr Gln
20 25 30

Lys Ile Leu Asn Thr Ile Arg Glu Leu Gly Lys Gln Gly Val Gln Phe
35 40 45

Ala Val Phe Pro Glu Thr Phe Ile Pro Tyr Tyr Pro Tyr Phe Thr Phe
50 55 60

Leu Gln Pro Pro Tyr Met Gln Ala Asp Gln His Leu Lys Val Met Glu
65 70 75 80

Glu Ala Val Thr Leu Pro Ser Ala Ser Thr Glu Ala Ile Gly Glu Ala
85 90 95

Ala Arg Glu Ala Gly Val Val Val Ser Ile Gly Val Asn Glu Arg Asp
100 105 110

Gly Ala Ser Ile Tyr Asn Thr Gln Leu Leu Phe Asp Ala Asp Gly Thr
115 120 125

Leu Ile Asn Arg Arg Arg Lys Ile Thr Pro Thr Phe His Glu Arg Met
130 135 140

Val Trp Gly Gln Gly Asp Gly Ser Gly Met Arg Ala Val Asp Thr Lys
145 150 155 160

Gly Gly Arg Ile Gly Gln Leu Ala Cys Trp Glu His Trp Asn Pro Leu
165 170 175

Ala Arg Tyr Ala Leu Ile Ala Asp Gly Glu Gln Ile His Ala Ala Met
180 185 190

Tyr Pro Gly Ser Ser Phe Gly Glu Leu Phe Ser Gln Gln Ile Asp Val
195 200 205

Ser Leu Arg Gln His Ala Leu Glu Ser Ala Ala Phe Val Val Ser Ser
210 215 220

Thr Gly Phe Leu Asp Ala Glu Gln Gln Ala Gln Val Val Lys Asp Thr
225 230 235 240

Gly Ser Pro Ile Gly Pro Ile Ser Gly Gly Asn Phe Thr Ala Ile Ile
245 250 255

Ala Pro Asp Gly Thr Ile Ile Gly Glu Pro Ile Arg Ser Gly Glu Gly
260 265 270

Phe Val Ile Ala Asp Leu Asp Phe Asn Leu Leu Asp Lys Arg Lys Arg
275 280 285

Leu Val Asp Ile Arg Ala His Tyr Asn Arg Pro Glu Leu Leu Ser Leu
290 295 300

Leu Ile Asp Arg Thr Pro Ala Glu Tyr Val Gln Glu Val Asn Lys Ser
305 310 315 320

Val Ser Glu

<210> SEQ ID NO 90
<211> LENGTH: 969
<212> TYPE: DNA
<213> ORGANISM: Artificial sequence
<220> FEATURE:
<223> OTHER INFORMATION: codon modified sequence

<400> SEQUENCE: 90
atgtctcact cgacaaacaa caactcctct actatcgttc gcgcggcggc ggtccagatt 60
tcgccggtgc tttactctcg ggatggcacc acgcaacgta ttatcaacac gattcgcgac 120
ctggctaaac agggtgtaca gttcgcggtt tttccagaaa ccttcattcc gtactatccg 180

```
tttttagct ggctgcaacc gccgtatgtt caggccgaac agcatctgaa actgattgat    240

gaagcggtta ccattccgag tgccaccacc gacgcaattg gcgatgccgc ccgcgaggcg    300

ggggtggtgg tgagtatcgg cttgaatgaa cgtgaaggcg gctccttata taacacgcag    360

gtcctgtttg atgcggaagg taccattttg cagcgtcgcc gtaaaattac cccgacctat    420

cacgagcgtt tactgtgggg ccagggcgaa ggtagcgcgc tccgtgccgt ggatagcaag    480

ggtggtcgca ttggccagct ggcgtgctgg gaacatttta atccacttgc gcgctatgcc    540

ctgctggcgg atggggagca aatccatgcg gcggtgtacc cagcgtccag ttggggcgat    600

ctgtttagcc agcagattga actgactctg cgtcaacatg caatcgaaag cggtgccttt    660

gtggtgtcca gtacggcatg gctggaagcg gataaccagg cgcaggttat gcgcgatacc    720

ggcagccctg tgggcccgat ttctggcggc aatttcaccg ccatcattgc accggaaggg    780

accatcattg gcgaaccgat tcgctcgggt gaaggttttg tcattgccga cctcgatttt    840

aacttgctgg aaaaacgtaa acggctgatc gatttaaaag gtcattataa ccgccctgaa    900

ttgctgtcgc tgttagtgga tcgcacgccg gcagaatatg tgaatgaggt taacaaaagc    960

gtgagcgaa                                                            969
```

<210> SEQ ID NO 91
<211> LENGTH: 323
<212> TYPE: PRT
<213> ORGANISM: Artificial sequence
<220> FEATURE:
<223> OTHER INFORMATION: translated protein from codon modified sequence

<400> SEQUENCE: 91

```
Met Ser His Ser Thr Asn Asn Asn Ser Ser Thr Ile Val Arg Ala Ala
1               5                   10                  15

Ala Val Gln Ile Ser Pro Val Leu Tyr Ser Arg Asp Gly Thr Thr Gln
            20                  25                  30

Arg Ile Ile Asn Thr Ile Arg Asp Leu Ala Lys Gln Gly Val Gln Phe
        35                  40                  45

Ala Val Phe Pro Glu Thr Phe Ile Pro Tyr Tyr Pro Phe Phe Ser Trp
    50                  55                  60

Leu Gln Pro Pro Tyr Val Gln Ala Glu Gln His Leu Lys Leu Ile Asp
65                  70                  75                  80

Glu Ala Val Thr Ile Pro Ser Ala Thr Thr Asp Ala Ile Gly Asp Ala
                85                  90                  95

Ala Arg Glu Ala Gly Val Val Val Ser Ile Gly Leu Asn Glu Arg Glu
            100                 105                 110

Gly Gly Ser Leu Tyr Asn Thr Gln Val Leu Phe Asp Ala Glu Gly Thr
        115                 120                 125

Ile Leu Gln Arg Arg Arg Lys Ile Thr Pro Thr Tyr His Glu Arg Leu
    130                 135                 140

Leu Trp Gly Gln Gly Glu Gly Ser Ala Leu Arg Ala Val Asp Ser Lys
145                 150                 155                 160

Gly Gly Arg Ile Gly Gln Leu Ala Cys Trp Glu His Phe Asn Pro Leu
                165                 170                 175

Ala Arg Tyr Ala Leu Leu Ala Asp Gly Glu Gln Ile His Ala Ala Val
            180                 185                 190

Tyr Pro Ala Ser Ser Trp Gly Asp Leu Phe Ser Gln Gln Ile Glu Leu
        195                 200                 205

Thr Leu Arg Gln His Ala Ile Glu Ser Gly Ala Phe Val Val Ser Ser
    210                 215                 220
```

```
Thr Ala Trp Leu Glu Ala Asp Asn Gln Ala Gln Val Met Arg Asp Thr
225                 230                 235                 240

Gly Ser Pro Val Gly Pro Ile Ser Gly Gly Asn Phe Thr Ala Ile Ile
                245                 250                 255

Ala Pro Glu Gly Thr Ile Ile Gly Glu Pro Ile Arg Ser Gly Glu Gly
            260                 265                 270

Phe Val Ile Ala Asp Leu Asp Phe Asn Leu Leu Glu Lys Arg Lys Arg
        275                 280                 285

Leu Ile Asp Leu Lys Gly His Tyr Asn Arg Pro Glu Leu Leu Ser Leu
    290                 295                 300

Leu Val Asp Arg Thr Pro Ala Glu Tyr Val Asn Glu Val Asn Lys Ser
305                 310                 315                 320

Val Ser Glu


<210> SEQ ID NO 92
<211> LENGTH: 969
<212> TYPE: DNA
<213> ORGANISM: Artificial sequence
<220> FEATURE:
<223> OTHER INFORMATION: codon modified sequence

<400> SEQUENCE: 92

atgtcacatt cgacgaataa caacacgagt accttggtgc gtgccgccgc ggtgcagatc      60

tccccgatcg tgtatagcaa agaagcgacc acccagaagg tcatcaacac catccgcgaa     120

ttagccaaaa acggcgtcca gtttgcggtc ttcccggaaa cctttgtgcc ttattatccg     180

tacttttctt tcctgcagcc accattcgta caggccgagc aacatgtgcg tttggtggat     240

gaagcggtga gcattccgag cgcgacctca gacgcaattg gggaagcggc acgtgaagcg     300

ggcatgattg ttagcgtggg gatgaatgag cgcgatgccg gtacactgta taacacgcag     360

atgctgtttg atgccgatgg tacgcttgtt cagcgccgcc gtaaaatcac cccgacgttc     420

catgaacgtc ttgtttgggc ccagggtgac ggtacgggcc tgaaagcggt tgaaaccaaa     480

gcgggtcgca ttggccaact ggcgtgctgg gaacattgga acccgttagc acggtttgcg     540

atgatcgcag atggtgaaca gattcacgcg gcaatttatc cagcatcgtc ttacggcgat     600

atgttttcgc agcagattga aatgtccctg aaacaacacg cgttagaaag cgccgcgttt     660

gttgttagct ccaccgcgtg gctggatgcc gataaccagg cccagatggt gcgcgattct     720

ggtactccgc tgggcccgat tagcgccggc aactttactg cgattatcgc gcctgatggc     780

accattattg cggaaccgat taaaaccggc gagggctttg tggtggctga tctggatttt     840

aacctgatcg accgccgtaa acgcattttg gatgtgaaag gccattataa tcgcccggaa     900

ctgctgagcg ttatgattga ccgtaccccg gcggattatg tccaagaagt gaataaaagt     960

gtgagtgaa                                                             969


<210> SEQ ID NO 93
<211> LENGTH: 323
<212> TYPE: PRT
<213> ORGANISM: Artificial sequence
<220> FEATURE:
<223> OTHER INFORMATION: translated protein from codon modified sequence

<400> SEQUENCE: 93

Met Ser His Ser Thr Asn Asn Asn Thr Ser Thr Leu Val Arg Ala Ala
1               5                   10                  15

Ala Val Gln Ile Ser Pro Ile Val Tyr Ser Lys Glu Ala Thr Thr Gln
```

```
            20                  25                  30

Lys Val Ile Asn Thr Ile Arg Glu Leu Ala Lys Asn Gly Val Gln Phe
        35                  40                  45

Ala Val Phe Pro Glu Thr Phe Val Pro Tyr Tyr Pro Tyr Phe Ser Phe
    50                  55                  60

Leu Gln Pro Pro Phe Val Gln Ala Glu Gln His Val Arg Leu Val Asp
65                  70                  75                  80

Glu Ala Val Ser Ile Pro Ser Ala Thr Ser Asp Ala Ile Gly Glu Ala
                85                  90                  95

Ala Arg Glu Ala Gly Met Ile Val Ser Val Gly Met Asn Glu Arg Asp
            100                 105                 110

Ala Gly Thr Leu Tyr Asn Thr Gln Met Leu Phe Asp Ala Asp Gly Thr
        115                 120                 125

Leu Val Gln Arg Arg Arg Lys Ile Thr Pro Thr Phe His Glu Arg Leu
    130                 135                 140

Val Trp Ala Gln Gly Asp Gly Thr Gly Leu Lys Ala Val Glu Thr Lys
145                 150                 155                 160

Ala Gly Arg Ile Gly Gln Leu Ala Cys Trp Glu His Trp Asn Pro Leu
                165                 170                 175

Ala Arg Phe Ala Met Ile Ala Asp Gly Glu Gln Ile His Ala Ala Ile
            180                 185                 190

Tyr Pro Ala Ser Ser Tyr Gly Asp Met Phe Ser Gln Gln Ile Glu Met
        195                 200                 205

Ser Leu Lys Gln His Ala Leu Glu Ser Ala Ala Phe Val Val Ser Ser
    210                 215                 220

Thr Ala Trp Leu Asp Ala Asp Asn Gln Ala Gln Met Val Arg Asp Ser
225                 230                 235                 240

Gly Thr Pro Leu Gly Pro Ile Ser Ala Gly Asn Phe Thr Ala Ile Ile
                245                 250                 255

Ala Pro Asp Gly Thr Ile Ile Ala Glu Pro Ile Lys Thr Gly Glu Gly
            260                 265                 270

Phe Val Val Ala Asp Leu Asp Phe Asn Leu Ile Asp Arg Arg Lys Arg
        275                 280                 285

Ile Leu Asp Val Lys Gly His Tyr Asn Arg Pro Glu Leu Leu Ser Val
    290                 295                 300

Met Ile Asp Arg Thr Pro Ala Asp Tyr Val Gln Glu Val Asn Lys Ser
305                 310                 315                 320

Val Ser Glu


<210> SEQ ID NO 94
<211> LENGTH: 1035
<212> TYPE: DNA
<213> ORGANISM: Artificial sequence
<220> FEATURE:
<223> OTHER INFORMATION: codon modified sequence

<400> SEQUENCE: 94

atgacgcagt cacagatcgt gaaagtggcc gcggttcaaa tgaacccggt tgtcgatagc      60

gccgatgcga ccgtggaacg cgtgttagac gaaattggtg cagcggcggc ggacggcgcc     120

cagttggtgg tgttcccgga aaccgcggtc ccatattatc ctttttggag ctttgtgatg     180

gcgccgatgg atatgggtgc gaaacaccgg gccttatatg aacattcccc aacgttgccg     240

ggtccgatca ccgaagccgt ggctgcggcc gcaaaaacgc atgaaatggt cgtggtggtg     300

ggggtcaatg aaaaagatca cggtagtctg tataattgcc aattagtttt tgatggcaac     360
```

```
ggcgagatcg cactgaaacg ccgcaaaatt actccgagct atcacgagcg tatggtttgg    420

ggccagggtg atggtaccgg catccatgcg gtggatactg cagtaggtcg cgttggcgct    480

ctggcatgct gggagcatta caacccgctg gcgcgttatg ccatgatggc cgatcacgaa    540

cagattcatt gcagtcagtg gccgggctcc ctgatgggcc caatttatgc ggaacagcag    600

gaggttacca ttcgccatca tgcgctggaa tcgggctgtt tcgtagtgaa cgcgaccggg    660

tggctggatg cggatcaact ggccagcgtc tctgaagacc cgggcatcca gaagggcctg    720

tacggtgggt gctataccgc aatcattgcg ccggaaggtt cgcatgttct ggccccgctc    780

ctggacggcc ctggccgtct ggtggcggat attgatctta gtcttattac gcggcgcaaa    840

cgcatgatgg atagcgttgg ccattacgca cgtccggaac tgttgtccct gcgcattgat    900

cgtcgttctc atgcggcgca gcatgcggat gcggccccgg gagtgggcgc tgtgagcgat    960

tttgacgaac cggatcatgg tgaacccgaa ccatacgcgg cctatcgcga tgccattgcg   1020

cgttcgtcta ccggc                                                    1035


<210> SEQ ID NO 95
<211> LENGTH: 345
<212> TYPE: PRT
<213> ORGANISM: Artificial sequence
<220> FEATURE:
<223> OTHER INFORMATION: translated protein from codon modified sequence

<400> SEQUENCE: 95

Met Thr Gln Ser Gln Ile Val Lys Val Ala Ala Val Gln Met Asn Pro
1               5                   10                  15

Val Val Asp Ser Ala Asp Ala Thr Val Glu Arg Val Leu Asp Glu Ile
            20                  25                  30

Gly Ala Ala Ala Ala Asp Gly Ala Gln Leu Val Val Phe Pro Glu Thr
        35                  40                  45

Ala Val Pro Tyr Tyr Pro Phe Trp Ser Phe Val Met Ala Pro Met Asp
    50                  55                  60

Met Gly Ala Lys His Arg Ala Leu Tyr Glu His Ser Pro Thr Leu Pro
65                  70                  75                  80

Gly Pro Ile Thr Glu Ala Val Ala Ala Ala Ala Lys Thr His Glu Met
                85                  90                  95

Val Val Val Val Gly Val Asn Glu Lys Asp His Gly Ser Leu Tyr Asn
            100                 105                 110

Cys Gln Leu Val Phe Asp Gly Asn Gly Glu Ile Ala Leu Lys Arg Arg
        115                 120                 125

Lys Ile Thr Pro Ser Tyr His Glu Arg Met Val Trp Gly Gln Gly Asp
    130                 135                 140

Gly Thr Gly Ile His Ala Val Asp Thr Ala Val Gly Arg Val Gly Ala
145                 150                 155                 160

Leu Ala Cys Trp Glu His Tyr Asn Pro Leu Ala Arg Tyr Ala Met Met
                165                 170                 175

Ala Asp His Glu Gln Ile His Cys Ser Gln Trp Pro Gly Ser Leu Met
            180                 185                 190

Gly Pro Ile Tyr Ala Glu Gln Gln Glu Val Thr Ile Arg His His Ala
        195                 200                 205

Leu Glu Ser Gly Cys Phe Val Val Asn Ala Thr Gly Trp Leu Asp Ala
    210                 215                 220

Asp Gln Leu Ala Ser Val Ser Glu Asp Pro Gly Ile Gln Lys Gly Leu
225                 230                 235                 240
```

```
Tyr Gly Gly Cys Tyr Thr Ala Ile Ile Ala Pro Glu Gly Ser His Val
                245                 250                 255

Leu Ala Pro Leu Leu Asp Gly Pro Gly Arg Leu Val Ala Asp Ile Asp
            260                 265                 270

Leu Ser Leu Ile Thr Arg Arg Lys Arg Met Met Asp Ser Val Gly His
        275                 280                 285

Tyr Ala Arg Pro Glu Leu Leu Ser Leu Arg Ile Asp Arg Arg Ser His
    290                 295                 300

Ala Ala Gln His Ala Asp Ala Ala Pro Gly Val Gly Ala Val Ser Asp
305                 310                 315                 320

Phe Asp Glu Pro Asp His Gly Glu Pro Glu Pro Tyr Ala Ala Tyr Arg
                325                 330                 335

Asp Ala Ile Ala Arg Ser Ser Thr Gly
            340                 345
```

<210> SEQ ID NO 96
<211> LENGTH: 1035
<212> TYPE: DNA
<213> ORGANISM: Artificial sequence
<220> FEATURE:
<223> OTHER INFORMATION: codon modified sequence

<400> SEQUENCE: 96

```
atgacgcaaa gtcagattct taaagttgcg gcggtgcaga ttaacccagt actggactcc     60

gcagaagcaa ccctggaacg tgtcgtggat gaaatcgcgg ccgcggccgc ggacggcgcg    120

cagctggtcg tttttcccga gaccgcctta ccatactacc cgtatttttc tttcgttctg    180

gccccggtgg aaatcgctgc ccgccaccgt gcggtgtttg agcattcacc gagcgtgccg    240

ggtccgctga ccgatggcgt ggcggcagcg gcgaaatcgc atgaaatggt cgttgtttta    300

ggcatgaacg agcgcgatca cggcagtatc tataactgtc aagtggtgtt tgatggtaac    360

ggtgaaattg ccttgcgtcg tcgcaaaatt acgccgacct ggcatgaacg tatggtgtgg    420

ggtcaaggcg acggcagcgg catccatgct gttgatacgg gcgtgggccg cgtgggcgcg    480

gtcgcgtgct gggaacactg gaatccggtg gcgcgctatg caatgatggc ggatcatgaa    540

cagatccact gctcccagtg gccaggatcc ctgattgggc cgatctttgc ggatcagcag    600

gaaattacca ttcgccatca tgcgattgaa tctggttgct tcgtggttca ggcgaccgcg    660

tggctggatg cagatcagct ggccagcgtt acggaagatc cggcactgca gaaaggcctc    720

tacggtgggt gctataccgc gattattgca ccggatggct ctcatgtggt gggcccgatg    780

atggatgcgc caggccgctt agttgcggat attgatttga gcctgattac taagcgcaaa    840

cgcatggtcg attcgctggg tcattatgcc cgtccggaat tgctgagtct tcgtattgat    900

cggcggagcc atgccgccca gcatgccgac gccgcgccgg gtgtggctgc ggtgactgaa    960

tttgaagagc cggatcatgg tgaacctgaa ccttatgccg cctatcgcga cgcgatcgcg   1020

cgtagctcga ccggg                                                    1035
```

<210> SEQ ID NO 97
<211> LENGTH: 345
<212> TYPE: PRT
<213> ORGANISM: Artificial sequence
<220> FEATURE:
<223> OTHER INFORMATION: translated protein from codon modified sequence

<400> SEQUENCE: 97

```
Met Thr Gln Ser Gln Ile Leu Lys Val Ala Ala Val Gln Ile Asn Pro
```

```
1               5                   10                  15

Val Leu Asp Ser Ala Glu Ala Thr Leu Glu Arg Val Val Asp Glu Ile
            20                  25                  30

Ala Ala Ala Ala Ala Asp Gly Ala Gln Leu Val Val Phe Pro Glu Thr
        35                  40                  45

Ala Leu Pro Tyr Tyr Pro Tyr Phe Ser Phe Val Leu Ala Pro Val Glu
    50                  55                  60

Ile Ala Ala Arg His Arg Ala Val Phe Glu His Ser Pro Ser Val Pro
65                  70                  75                  80

Gly Pro Leu Thr Asp Gly Val Ala Ala Ala Ala Lys Ser His Glu Met
                85                  90                  95

Val Val Val Leu Gly Met Asn Glu Arg Asp His Gly Ser Ile Tyr Asn
            100                 105                 110

Cys Gln Val Val Phe Asp Gly Asn Gly Glu Ile Ala Leu Arg Arg Arg
        115                 120                 125

Lys Ile Thr Pro Thr Trp His Glu Arg Met Val Trp Gly Gln Gly Asp
    130                 135                 140

Gly Ser Gly Ile His Ala Val Asp Thr Gly Val Gly Arg Val Gly Ala
145                 150                 155                 160

Val Ala Cys Trp Glu His Trp Asn Pro Val Ala Arg Tyr Ala Met Met
                165                 170                 175

Ala Asp His Glu Gln Ile His Cys Ser Gln Trp Pro Gly Ser Leu Ile
            180                 185                 190

Gly Pro Ile Phe Ala Asp Gln Gln Glu Ile Thr Ile Arg His His Ala
        195                 200                 205

Ile Glu Ser Gly Cys Phe Val Val Gln Ala Thr Ala Trp Leu Asp Ala
    210                 215                 220

Asp Gln Leu Ala Ser Val Thr Glu Asp Pro Ala Leu Gln Lys Gly Leu
225                 230                 235                 240

Tyr Gly Gly Cys Tyr Thr Ala Ile Ile Ala Pro Asp Gly Ser His Val
                245                 250                 255

Val Gly Pro Met Met Asp Ala Pro Gly Arg Leu Val Ala Asp Ile Asp
            260                 265                 270

Leu Ser Leu Ile Thr Lys Arg Lys Arg Met Val Asp Ser Leu Gly His
        275                 280                 285

Tyr Ala Arg Pro Glu Leu Leu Ser Leu Arg Ile Asp Arg Arg Ser His
    290                 295                 300

Ala Ala Gln His Ala Asp Ala Ala Pro Gly Val Ala Ala Val Thr Glu
305                 310                 315                 320

Phe Glu Glu Pro Asp His Gly Glu Pro Glu Pro Tyr Ala Ala Tyr Arg
                325                 330                 335

Asp Ala Ile Ala Arg Ser Ser Thr Gly
            340                 345
```

<210> SEQ ID NO 98
<211> LENGTH: 1035
<212> TYPE: DNA
<213> ORGANISM: Artificial sequence
<220> FEATURE:
<223> OTHER INFORMATION: codon modified sequence

<400> SEQUENCE: 98

```
atgtcgcaga gccaaatctt aaaagtggcc gcggtccaga tgaacccgat gcttgaaagc      60

gcagaagcga ccatcgaacg cttactggag gaaattgcgg cggcggcagc cgacggggcc     120
```

```
cagttagtgg tttttccgga aaccgcggtt ccgtactacc cgttctttag ctgggtgatt    180

gccccactgg atatggcggc ccggcataag gcggttttcg atcattctcc ctctgttcca    240

ggtcctgtca ctgatgcggt ggctgcagca gcccgctccc acgaagtttt ggttgttatc    300

ggcgtgaatg aacgtgaaca tgcgtcactg tataactgcc agttggtgtt tgatggtaac    360

ggtgaaattg cacttaaacg ccgtaaatta actcctacgt atcacgaaaa actgttgtgg    420

ggtcagggag aaggttcggg cctgcatgcg gtggagaccg cgattgggcg cgtgggcggc    480

ctggcctgct gggaacattg gaatccgctg gcccgctatg ccatgctggg cgatcatgaa    540

cagattcatt gcagtcagtt tccagcttcc ctggtcggcc cgattttcgc ggatcaacag    600

gaaatcaccg tgcgtcatca tgcgctggaa agcgggtgtt ttgtcgtgaa cgcgaccgct    660

tggctggagg cggaacagat tggcacgctg acggaggatc cagcgttgca acgcggtatt    720

tttggcggtt gctataccgc gatcattgcg ccggaaggct cgcacgtgat cggtccggta    780

ctcgagggcc cgggccgcct gatggccgat attgatctca ccatgattac gcgtcgtaaa    840

cgtctgatcg atagtgtggg tcattatgcg cggccggaac tgctgagcct gcgcattgat    900

cgccgtagcc atgcagccca gcacgcggac gcggcaccgg gcattggcgc cgtgagtgac    960

tttgatgaac cggaacatgc cgaaccggat ccgtatgcgg cgtatcgtga cgccattgcg   1020

cgctcctcta ccggc                                                    1035
```

<210> SEQ ID NO 99
<211> LENGTH: 345
<212> TYPE: PRT
<213> ORGANISM: Artificial sequence
<220> FEATURE:
<223> OTHER INFORMATION: translated protein from codon modified sequence

<400> SEQUENCE: 99

```
Met Ser Gln Ser Gln Ile Leu Lys Val Ala Ala Val Gln Met Asn Pro
1               5                   10                  15

Met Leu Glu Ser Ala Glu Ala Thr Ile Glu Arg Leu Leu Glu Glu Ile
            20                  25                  30

Ala Ala Ala Ala Ala Asp Gly Ala Gln Leu Val Val Phe Pro Glu Thr
        35                  40                  45

Ala Val Pro Tyr Tyr Pro Phe Phe Ser Trp Val Ile Ala Pro Leu Asp
    50                  55                  60

Met Ala Ala Arg His Lys Ala Val Phe Asp His Ser Pro Ser Val Pro
65                  70                  75                  80

Gly Pro Val Thr Asp Ala Val Ala Ala Ala Ala Arg Ser His Glu Val
                85                  90                  95

Leu Val Val Ile Gly Val Asn Glu Arg Glu His Ala Ser Leu Tyr Asn
            100                 105                 110

Cys Gln Leu Val Phe Asp Gly Asn Gly Glu Ile Ala Leu Lys Arg Arg
        115                 120                 125

Lys Leu Thr Pro Thr Tyr His Glu Lys Leu Leu Trp Gly Gln Gly Glu
    130                 135                 140

Gly Ser Gly Leu His Ala Val Glu Thr Ala Ile Gly Arg Val Gly Gly
145                 150                 155                 160

Leu Ala Cys Trp Glu His Trp Asn Pro Leu Ala Arg Tyr Ala Met Leu
                165                 170                 175

Gly Asp His Glu Gln Ile His Cys Ser Gln Phe Pro Ala Ser Leu Val
            180                 185                 190

Gly Pro Ile Phe Ala Asp Gln Gln Glu Ile Thr Val Arg His His Ala
```

```
        195                 200                 205

Leu Glu Ser Gly Cys Phe Val Val Asn Ala Thr Ala Trp Leu Glu Ala
    210                 215                 220

Glu Gln Ile Gly Thr Leu Thr Glu Asp Pro Ala Leu Gln Arg Gly Ile
225                 230                 235                 240

Phe Gly Gly Cys Tyr Thr Ala Ile Ile Ala Pro Glu Gly Ser His Val
                245                 250                 255

Ile Gly Pro Val Leu Glu Gly Pro Gly Arg Leu Met Ala Asp Ile Asp
            260                 265                 270

Leu Thr Met Ile Thr Arg Arg Lys Arg Leu Ile Asp Ser Val Gly His
        275                 280                 285

Tyr Ala Arg Pro Glu Leu Leu Ser Leu Arg Ile Asp Arg Arg Ser His
    290                 295                 300

Ala Ala Gln His Ala Asp Ala Ala Pro Gly Ile Gly Ala Val Ser Asp
305                 310                 315                 320

Phe Asp Glu Pro Glu His Ala Glu Pro Asp Pro Tyr Ala Ala Tyr Arg
                325                 330                 335

Asp Ala Ile Ala Arg Ser Ser Thr Gly
            340                 345


<210> SEQ ID NO 100
<211> LENGTH: 954
<212> TYPE: DNA
<213> ORGANISM: Smithella sp.
<220> FEATURE:
<223> OTHER INFORMATION: Smithella sp. SDB

<400> SEQUENCE: 100

atgaaaaacc agaccaaagt tgctgctatc cagctggcta ccaaaatcgg tgactctaac     60

accaacatcg ctggttgcga acgtctggct ctgatggcta tcaaaaacgg tgctcgttgg    120

atcgctctgc cggaattctt caccaccggt gtttcttgga aaccggaaat cgcttcttct    180

atccagaccg ttgacggtgc tgctgcttct ttcatgtgcg acttctctgc taaacaccag    240

gttgttctgg gtggttcttt cctgtgccgt ctgtctgacg gttctgttcg taaccgttac    300

cagtgctacg ctaacggttc tctgatcggt cagcacgaca aagacctgcc gaccatgtgg    360

gaaaactact tctacgaagg tggtgacccg atggactctg gtgttctggg tacctacaac    420

aacatccgta tcggtgctgc tgtttgctgg gaattcatgc gtaccatgac cgctcgtcgt    480

ctgcgtaaca aagttgacgt tatcatcggt ggttcttgct ggtggtctat cccgaccaac    540

ttcccggttt tcctgcagaa actgtgggaa ccggctaacc actactgctc tctggctgct    600

atccaggact ctgctcgtct gatcggtgct ccggttatcc acgctgctca ctgcggtgaa    660

atcgaatgcc cgatgccggg tctgccgatc aaataccgtg gttacttcga aggtaacgct    720

tctatcgttg acgcttctgg taaagttctg gctcagcgtt ctgctgaaca gggtgaaggt    780

atcgtttgcg ctgacatcct gctggaagct cagccgacca tcgaagctat cccggaccgt    840

ttctggctgc gttctcgtgg tttcctgccg accttcgctt ggcaccacca gcgttggctg    900

ggtcgtcgtt ggtacaaacg taacgttcgt cagaaaaaaa acgaactgca ccac          954


<210> SEQ ID NO 101
<211> LENGTH: 318
<212> TYPE: PRT
<213> ORGANISM: Smithella sp.
<220> FEATURE:
<223> OTHER INFORMATION: Smithella sp. SDB
```

<400> SEQUENCE: 101

Met Lys Asn Gln Thr Lys Val Ala Ala Ile Gln Leu Ala Thr Lys Ile
1               5                   10                  15

Gly Asp Ser Asn Thr Asn Ile Ala Gly Cys Glu Arg Leu Ala Leu Met
            20                  25                  30

Ala Ile Lys Asn Gly Ala Arg Trp Ile Ala Leu Pro Glu Phe Phe Thr
        35                  40                  45

Thr Gly Val Ser Trp Lys Pro Glu Ile Ala Ser Ser Ile Gln Thr Val
    50                  55                  60

Asp Gly Ala Ala Ala Ser Phe Met Cys Asp Phe Ser Ala Lys His Gln
65                  70                  75                  80

Val Val Leu Gly Gly Ser Phe Leu Cys Arg Leu Ser Asp Gly Ser Val
                85                  90                  95

Arg Asn Arg Tyr Gln Cys Tyr Ala Asn Gly Ser Leu Ile Gly Gln His
            100                 105                 110

Asp Lys Asp Leu Pro Thr Met Trp Glu Asn Tyr Phe Tyr Glu Gly Gly
        115                 120                 125

Asp Pro Met Asp Ser Gly Val Leu Gly Thr Tyr Asn Asn Ile Arg Ile
    130                 135                 140

Gly Ala Ala Val Cys Trp Glu Phe Met Arg Thr Met Thr Ala Arg Arg
145                 150                 155                 160

Leu Arg Asn Lys Val Asp Val Ile Ile Gly Gly Ser Cys Trp Trp Ser
                165                 170                 175

Ile Pro Thr Asn Phe Pro Val Phe Leu Gln Lys Leu Trp Glu Pro Ala
            180                 185                 190

Asn His Tyr Cys Ser Leu Ala Ala Ile Gln Asp Ser Ala Arg Leu Ile
        195                 200                 205

Gly Ala Pro Val Ile His Ala Ala His Cys Gly Glu Ile Glu Cys Pro
    210                 215                 220

Met Pro Gly Leu Pro Ile Lys Tyr Arg Gly Tyr Phe Glu Gly Asn Ala
225                 230                 235                 240

Ser Ile Val Asp Ala Ser Gly Lys Val Leu Ala Gln Arg Ser Ala Glu
                245                 250                 255

Gln Gly Glu Gly Ile Val Cys Ala Asp Ile Leu Leu Glu Ala Gln Pro
            260                 265                 270

Thr Ile Glu Ala Ile Pro Asp Arg Phe Trp Leu Arg Ser Arg Gly Phe
        275                 280                 285

Leu Pro Thr Phe Ala Trp His His Gln Arg Trp Leu Gly Arg Arg Trp
    290                 295                 300

Tyr Lys Arg Asn Val Arg Gln Lys Lys Asn Glu Leu His His
305                 310                 315

<210> SEQ ID NO 102
<211> LENGTH: 963
<212> TYPE: DNA
<213> ORGANISM: Bradyrhizobium diazoefficiens

<400> SEQUENCE: 102
atgatggata gtaaccgccc gaatacctat aaagcagccg tggtgcaggc agccagcgat 60
ccgaccagca gcctggttag tgcacagaaa gccgcagccc tgattgaaaa agccgccggt 120
gcaggtgcac gtctggttgt gtttccggaa gcctttattg gtggttatcc gaaaggtaat 180
agctttggtg ccccggtggg catgcgtaaa ccggaaggtc gtgaagcatt tcgtctgtat 240
tgggaagcag caattgatct ggatggcgtt gaagtggaaa ccattgccgc agcagcagca 300

```
gcgaccggtg cctttaccgt tattggctgt attgaacgtg aacagggcac cctgtattgc    360

accgcactgt tttcgatgg cgcccgtggt ctggttggta aacatcgtaa actgatgccg    420

accgccggcg aacgcctgat ttggggcttt ggtgacggta gcaccatgcc ggtgtttgaa    480

accagtctgg gtaatattgg cgcagttatt tgctgggaaa attatatgcc gatgctgcgc    540

atgcacatgt atagtcaggg cattagtatc tattgtgccc cgaccgcaga tgatcgtgat    600

acctggctgc cgaccatgca gcatattgca ctggaaggcc gctgctttgt tctgaccgcc    660

tgccagcatc tgaaacgtgg cgcatttccg gccgattatg aatgcgcact gggcgcagat    720

ccggaaaccg tgctgatgcg cggtggtagt gcaattgtga atccgctggg taaagttctg    780

gccggcccgt gctttgaagg cgaaaccatt ctgtatgcag atattgcact ggatgaagtt    840

acccgtggta aatttgattt tgatgcagca ggccattata gtcgtccgga tgtgtttcag    900

ctggttgtgg atgatcgtcc gaaacgcgcc gttagcaccg tgagcgccgt gcgtgcccgc    960

aat                                                                  963
```

```
<210> SEQ ID NO 103
<211> LENGTH: 321
<212> TYPE: PRT
<213> ORGANISM: Bradyrhizobium diazoefficiens

<400> SEQUENCE: 103

Met Met Asp Ser Asn Arg Pro Asn Thr Tyr Lys Ala Ala Val Val Gln
1               5                   10                  15

Ala Ala Ser Asp Pro Thr Ser Ser Leu Val Ser Ala Gln Lys Ala Ala
            20                  25                  30

Ala Leu Ile Glu Lys Ala Ala Gly Ala Gly Ala Arg Leu Val Val Phe
        35                  40                  45

Pro Glu Ala Phe Ile Gly Gly Tyr Pro Lys Gly Asn Ser Phe Gly Ala
    50                  55                  60

Pro Val Gly Met Arg Lys Pro Glu Gly Arg Glu Ala Phe Arg Leu Tyr
65                  70                  75                  80

Trp Glu Ala Ala Ile Asp Leu Asp Gly Val Glu Val Glu Thr Ile Ala
                85                  90                  95

Ala Ala Ala Ala Ala Thr Gly Ala Phe Thr Val Ile Gly Cys Ile Glu
            100                 105                 110

Arg Glu Gln Gly Thr Leu Tyr Cys Thr Ala Leu Phe Phe Asp Gly Ala
        115                 120                 125

Arg Gly Leu Val Gly Lys His Arg Lys Leu Met Pro Thr Ala Gly Glu
    130                 135                 140

Arg Leu Ile Trp Gly Phe Gly Asp Gly Ser Thr Met Pro Val Phe Glu
145                 150                 155                 160

Thr Ser Leu Gly Asn Ile Gly Ala Val Ile Cys Trp Glu Asn Tyr Met
                165                 170                 175

Pro Met Leu Arg Met His Met Tyr Ser Gln Gly Ile Ser Ile Tyr Cys
            180                 185                 190

Ala Pro Thr Ala Asp Asp Arg Asp Thr Trp Leu Pro Thr Met Gln His
        195                 200                 205

Ile Ala Leu Glu Gly Arg Cys Phe Val Leu Thr Ala Cys Gln His Leu
    210                 215                 220

Lys Arg Gly Ala Phe Pro Ala Asp Tyr Glu Cys Ala Leu Gly Ala Asp
225                 230                 235                 240

Pro Glu Thr Val Leu Met Arg Gly Gly Ser Ala Ile Val Asn Pro Leu
```

```
                245                 250                 255

Gly Lys Val Leu Ala Gly Pro Cys Phe Glu Gly Glu Thr Ile Leu Tyr
            260                 265                 270

Ala Asp Ile Ala Leu Asp Glu Val Thr Arg Gly Lys Phe Asp Phe Asp
        275                 280                 285

Ala Ala Gly His Tyr Ser Arg Pro Asp Val Phe Gln Leu Val Val Asp
    290                 295                 300

Asp Arg Pro Lys Arg Ala Val Ser Thr Val Ser Ala Val Arg Ala Arg
305                 310                 315                 320

Asn


<210> SEQ ID NO 104
<211> LENGTH: 951
<212> TYPE: DNA
<213> ORGANISM: Aquimarina atlantica

<400> SEQUENCE: 104

atgaaagacc agctgctgac cgttgctctg gctcagatct ctccggtttg gctggacaaa      60

accgctacca tcaaaaaaat cgaaaactct atcgctgaag ctgcttctaa aaaagctgaa     120

ctgatcgttt tcggtgaatc tctgctgccg ggttacccgt tctgggtttc tctgaccgac     180

ggtgctaaat tcgactctaa aatccagaaa gaaatccacg ctcactacgc tcagaactct     240

atcgttatcg aaaacggtga cctggacacc atctgcgaac tggctgctga atgcaacatc     300

gctatctacc tgggtatcat cgaacgtccg atcgaccgtg gtggtcactc tctgtacgct     360

tctctggttt acatcgacca gaaaggtgaa atcaaatctg ttcaccgtaa actgcagccg     420

acctacgaag aacgtctgac ctgggctccg ggtgacggta acggtctgct ggttcacccg     480

ctgaaagctt tcaccgttgg tggtctgaac tgctgggaaa actggatgcc gctgccgcgt     540

gctgctctgt acggtcaggg tgaaaacctg cacatcgctg tttggccggg ttctgactac     600

aacaccaaag acatcacccg tttcatcgct cgtgaatctc gttcttacgt tatctctgtt     660

tcttctctga tgcgtaccga agacttcccg aaaaccaccc cgcacctgga cgaaatcctg     720

aaaaaagctc cggacgttct gggtaacggt ggttcttgca tcgctggtcc ggacggtgaa     780

tgggttatga aaccggttct gcacaaagaa ggtctgctga tcgaaaccct ggacttctct     840

aaagttctgc aggaacgtca gaacttcgac ccggttggtc actactctcg tccggacgtt     900

acccagctgc acgttaaccg taaacgtcag tctaccgttc gtttcgacga a              951


<210> SEQ ID NO 105
<211> LENGTH: 317
<212> TYPE: PRT
<213> ORGANISM: Aquimarina atlantica

<400> SEQUENCE: 105

Met Lys Asp Gln Leu Leu Thr Val Ala Leu Ala Gln Ile Ser Pro Val
1               5                   10                  15

Trp Leu Asp Lys Thr Ala Thr Ile Lys Lys Ile Glu Asn Ser Ile Ala
            20                  25                  30

Glu Ala Ala Ser Lys Lys Ala Glu Leu Ile Val Phe Gly Glu Ser Leu
        35                  40                  45

Leu Pro Gly Tyr Pro Phe Trp Val Ser Leu Thr Asp Gly Ala Lys Phe
    50                  55                  60

Asp Ser Lys Ile Gln Lys Glu Ile His Ala His Tyr Ala Gln Asn Ser
65                  70                  75                  80
```

```
Ile Val Ile Glu Asn Gly Asp Leu Asp Thr Ile Cys Glu Leu Ala Ala
                85                  90                  95

Glu Cys Asn Ile Ala Ile Tyr Leu Gly Ile Ile Glu Arg Pro Ile Asp
            100                 105                 110

Arg Gly Gly His Ser Leu Tyr Ala Ser Leu Val Tyr Ile Asp Gln Lys
        115                 120                 125

Gly Glu Ile Lys Ser Val His Arg Lys Leu Gln Pro Thr Tyr Glu Glu
    130                 135                 140

Arg Leu Thr Trp Ala Pro Gly Asp Gly Asn Gly Leu Leu Val His Pro
145                 150                 155                 160

Leu Lys Ala Phe Thr Val Gly Gly Leu Asn Cys Trp Glu Asn Trp Met
                165                 170                 175

Pro Leu Pro Arg Ala Ala Leu Tyr Gly Gln Gly Glu Asn Leu His Ile
            180                 185                 190

Ala Val Trp Pro Gly Ser Asp Tyr Asn Thr Lys Asp Ile Thr Arg Phe
        195                 200                 205

Ile Ala Arg Glu Ser Arg Ser Tyr Val Ile Ser Val Ser Ser Leu Met
    210                 215                 220

Arg Thr Glu Asp Phe Pro Lys Thr Thr Pro His Leu Asp Glu Ile Leu
225                 230                 235                 240

Lys Lys Ala Pro Asp Val Leu Gly Asn Gly Gly Ser Cys Ile Ala Gly
                245                 250                 255

Pro Asp Gly Glu Trp Val Met Lys Pro Val Leu His Lys Glu Gly Leu
            260                 265                 270

Leu Ile Glu Thr Leu Asp Phe Ser Lys Val Leu Gln Glu Arg Gln Asn
        275                 280                 285

Phe Asp Pro Val Gly His Tyr Ser Arg Pro Asp Val Thr Gln Leu His
    290                 295                 300

Val Asn Arg Lys Arg Gln Ser Thr Val Arg Phe Asp Glu
305                 310                 315
```

<210> SEQ ID NO 106
<211> LENGTH: 945
<212> TYPE: DNA
<213> ORGANISM: Arthrobacter sp.
<220> FEATURE:
<223> OTHER INFORMATION: Arthrobacter sp. Soil736

<400> SEQUENCE: 106

```
atgcgtatcg ctgctatcca ggctaccccg gttatcctgg acgctgaagc ttctgtttct     60

aaagctctgc gtctgctggg tgaagctgct ggtcagggtg ttaaactggc tgttttcccg    120

gaaaccttca tcccgctgta cccgtctggt gtttgggctt accaggctgc tcgtttcgac    180

ggtttcgacg aaatgtggac ccgtctgtgg gacaactctg ttgacgttcc gggtccgcag    240

atcgaccgtt tcatcaaagc ttgcgctgaa cacgacatct actgcgttct gggtgttaac    300

gaacgtgaat ctgctcgtcc gggttctctg tacaacacca tgatcctgct gggtccggaa    360

ggtctgctgt ggaaacaccg taaactgatg ccgaccatgc acgaacgtct gttccacggt    420

gttggttacg gtcaggacct gaacgttatc gaaaccccgg ttggtcgtgt tggtggtctg    480

atctgctggg aaaaccgtat gccgctggct cgttacgctg tttaccgtca gggtgttcag    540

atctgggctg ctccgaccgc tgacgactct gacggttgga tctctaccat gtctcacatc    600

gctatcgaat ctggtgcttt cgttgtttct gctccgcagt acatcccgcg ttctgctttc    660

ccggacgact tcccggttca gctgccggac gacggtcagg ctctgggtcg tggtggtgct    720
```

```
gctatcttcg aaccgctgca gggtcgtgct atcgctggtc cgctgtacga ccaggaaggt    780

atcgttgttg ctgacgttga cctgggtcgt tctctgaccg ctaaacgtat cttcgacgtt    840

gttggtcact actctcgtga agacgttctg tacccgccgg ctccgaccaa ccacgctccg    900

gaaggtccgg ctttctggcc gcgtacccgt ccgctgctgg gtaac                    945


<210> SEQ ID NO 107
<211> LENGTH: 315
<212> TYPE: PRT
<213> ORGANISM: Arthrobacter sp.
<220> FEATURE:
<223> OTHER INFORMATION: Arthrobacter sp. Soil736

<400> SEQUENCE: 107

Met Arg Ile Ala Ala Ile Gln Ala Thr Pro Val Ile Leu Asp Ala Glu
1               5                   10                  15

Ala Ser Val Ser Lys Ala Leu Arg Leu Leu Gly Glu Ala Ala Gly Gln
            20                  25                  30

Gly Val Lys Leu Ala Val Phe Pro Glu Thr Phe Ile Pro Leu Tyr Pro
        35                  40                  45

Ser Gly Val Trp Ala Tyr Gln Ala Ala Arg Phe Asp Gly Phe Asp Glu
    50                  55                  60

Met Trp Thr Arg Leu Trp Asp Asn Ser Val Asp Val Pro Gly Pro Gln
65                  70                  75                  80

Ile Asp Arg Phe Ile Lys Ala Cys Ala Glu His Asp Ile Tyr Cys Val
                85                  90                  95

Leu Gly Val Asn Glu Arg Glu Ser Ala Arg Pro Gly Ser Leu Tyr Asn
            100                 105                 110

Thr Met Ile Leu Leu Gly Pro Glu Gly Leu Leu Trp Lys His Arg Lys
        115                 120                 125

Leu Met Pro Thr Met His Glu Arg Leu Phe His Gly Val Gly Tyr Gly
    130                 135                 140

Gln Asp Leu Asn Val Ile Glu Thr Pro Val Gly Arg Val Gly Gly Leu
145                 150                 155                 160

Ile Cys Trp Glu Asn Arg Met Pro Leu Ala Arg Tyr Ala Val Tyr Arg
                165                 170                 175

Gln Gly Val Gln Ile Trp Ala Ala Pro Thr Ala Asp Asp Ser Asp Gly
            180                 185                 190

Trp Ile Ser Thr Met Ser His Ile Ala Ile Glu Ser Gly Ala Phe Val
        195                 200                 205

Val Ser Ala Pro Gln Tyr Ile Pro Arg Ser Ala Phe Pro Asp Asp Phe
    210                 215                 220

Pro Val Gln Leu Pro Asp Asp Gly Gln Ala Leu Gly Arg Gly Gly Ala
225                 230                 235                 240

Ala Ile Phe Glu Pro Leu Gln Gly Arg Ala Ile Ala Gly Pro Leu Tyr
                245                 250                 255

Asp Gln Glu Gly Ile Val Val Ala Asp Val Asp Leu Gly Arg Ser Leu
            260                 265                 270

Thr Ala Lys Arg Ile Phe Asp Val Val Gly His Tyr Ser Arg Glu Asp
        275                 280                 285

Val Leu Tyr Pro Pro Ala Pro Thr Asn His Ala Pro Glu Gly Pro Ala
    290                 295                 300

Phe Trp Pro Arg Thr Arg Pro Leu Leu Gly Asn
305                 310                 315
```

<210> SEQ ID NO 108
<211> LENGTH: 951
<212> TYPE: DNA
<213> ORGANISM: Pseudomonas mandelii
<220> FEATURE:
<223> OTHER INFORMATION: Pseudomonas mandelii JR-1

<400> SEQUENCE: 108
atggaaaacg ctatgaccaa agttgctatc atccagcgtc cgccggttct gctggaccgt 60
tctgctacca tcgctcgtgc tgttcagtct gttgctgaag ctgctgctgc tggtgcttct 120
ctgatcgttc tgccggaatc tttcatcccg ggttacccgt cttggatctg gcgtctggct 180
gctggtaaag acggtgctgt tatgggtcag ctgcacaccc gtctgctggc taacgctgtt 240
gacatcgcta acggtgacct gggtgaactg tgcgaagctg ctcgtgttca cgctgttacc 300
atcgtttgcg gtatcaacga atgcgaccgt tctaccggtg gtggtaccct gtacaactct 360
gttgttgtta tcggtgctga cggtgctgtt ctgaaccgtc accgtaaact gatgccgacc 420
aacccggaac gtatggttca cggtttcggt gacgcttctg gtctgcgtgc tgttgacacc 480
ccggttggtc gtgttggtgc tctgatctgc tgggaaaact acatgccgct ggctcgttac 540
tctctgtacg ctcagggtgt tgaaatctac atcgctccga cctacgacac cggtgaaggt 600
tggatctcta ccatgcgtca catcgctctg gaaggtcgtt gctgggttct gggttctggt 660
accgctctgc gtggttctga catcccggaa gacttcccgg ctcgtatgca gctgttcgct 720
gacccggacg aatggatcaa cgacggtgac tctgttgttg tttctccgca gggtcgtgtt 780
gttgctggtc cgctgcaccg tgaagctggt atcctgtacg ctgacatcga cgttgctctg 840
gttgctccgg ctcgtcgtgc tctggacgtt accggtcact acgctcgtcc ggacatcttc 900
gaactgcacg ttcgtcgttc tccggctatc ccggttcact acatcgacga a 951

<210> SEQ ID NO 109
<211> LENGTH: 317
<212> TYPE: PRT
<213> ORGANISM: Pseudomonas mandelii
<220> FEATURE:
<223> OTHER INFORMATION: Pseudomonas mandelii JR-1

<400> SEQUENCE: 109

Met Glu Asn Ala Met Thr Lys Val Ala Ile Ile Gln Arg Pro Pro Val
1 5 10 15

Leu Leu Asp Arg Ser Ala Thr Ile Ala Arg Ala Val Gln Ser Val Ala
20 25 30

Glu Ala Ala Ala Ala Gly Ala Ser Leu Ile Val Leu Pro Glu Ser Phe
35 40 45

Ile Pro Gly Tyr Pro Ser Trp Ile Trp Arg Leu Ala Ala Gly Lys Asp
50 55 60

Gly Ala Val Met Gly Gln Leu His Thr Arg Leu Leu Ala Asn Ala Val
65 70 75 80

Asp Ile Ala Asn Gly Asp Leu Gly Glu Leu Cys Glu Ala Ala Arg Val
85 90 95

His Ala Val Thr Ile Val Cys Gly Ile Asn Glu Cys Asp Arg Ser Thr
100 105 110

Gly Gly Gly Thr Leu Tyr Asn Ser Val Val Val Ile Gly Ala Asp Gly
115 120 125

Ala Val Leu Asn Arg His Arg Lys Leu Met Pro Thr Asn Pro Glu Arg
130 135 140

Met Val His Gly Phe Gly Asp Ala Ser Gly Leu Arg Ala Val Asp Thr

```
145                 150                 155                 160

Pro Val Gly Arg Val Gly Ala Leu Ile Cys Trp Glu Asn Tyr Met Pro
                165                 170                 175

Leu Ala Arg Tyr Ser Leu Tyr Ala Gln Gly Val Glu Ile Tyr Ile Ala
            180                 185                 190

Pro Thr Tyr Asp Thr Gly Glu Gly Trp Ile Ser Thr Met Arg His Ile
        195                 200                 205

Ala Leu Glu Gly Arg Cys Trp Val Leu Gly Ser Gly Thr Ala Leu Arg
    210                 215                 220

Gly Ser Asp Ile Pro Glu Asp Phe Pro Ala Arg Met Gln Leu Phe Ala
225                 230                 235                 240

Asp Pro Asp Glu Trp Ile Asn Asp Gly Asp Ser Val Val Val Ser Pro
                245                 250                 255

Gln Gly Arg Val Val Ala Gly Pro Leu His Arg Glu Ala Gly Ile Leu
            260                 265                 270

Tyr Ala Asp Ile Asp Val Ala Leu Val Ala Pro Ala Arg Arg Ala Leu
        275                 280                 285

Asp Val Thr Gly His Tyr Ala Arg Pro Asp Ile Phe Glu Leu His Val
    290                 295                 300

Arg Arg Ser Pro Ala Ile Pro Val His Tyr Ile Asp Glu
305                 310                 315
```

<210> SEQ ID NO 110
<211> LENGTH: 975
<212> TYPE: DNA
<213> ORGANISM: Pseudomonas sp
<220> FEATURE:
<223> OTHER INFORMATION: Pseudomonas sp. RIT357

<400> SEQUENCE: 110

```
atgaccagca aacgtgaaaa aaccgtggcc attgtgcaga tgccggcagc actgctggat     60

cgcgccgaaa gtatgcgccg cgcagccgaa catattaaga aagcagccct gcaagaagca    120

cagctggtta tttttccgga aacctggctg agttgttatc cggcctgggt gtttggtatg    180

gccggttggg atgatgcaca ggcaaaaagc tggtatgcaa aactgctggc agatagtccg    240

gttattggtc agccggaaga tatgcatgat gatctggcag aactgcgtga agccgcccgc    300

gtgaatgccg tgaccgtggt tatgggcatg aatgaacgta gtcgtcatca tggtggtagc    360

ctgtataata gtctggttac cattggtccg gatggtgcaa ttctgaatgt tcatcgtaaa    420

ctgaccccga cccataccga acgtaccgtt tgggcaaatg gtgacgcagc aggtctgcgc    480

gtggttgata ccgtggttgg tcgtgtgggt ggcctggttt gctgggaaca ttggcatccg    540

ctggcccgcc aggccctgca tgctcaagat gaacagattc atgttgcagc ctggccggat    600

atgccggaaa tgcatcatgt ggccgcccgc agctatgcat ttgaaggtcg ttgttttgtt    660

ctgtgtgcag gccagtatct ggcagcaggc gatgtgccgg cagaactgct ggccgcatat    720

cgccgtggcg ttggtggtaa agccctggaa gaagatgttc tgtttaatgg tggtagtggc    780

gttattgcac cggatggtag ttgggtgacc gcaccgctgt ttggcgaacc gggtattatt    840

ctggccacca ttgatctggc ccagattgat gcccagcatc atgatctgga tgtggcaggc    900

cattatctgc gtccggatgt gtttgaactg agtattgatc gccgcgttcg caccggtctg    960

accctgcgtg atgca                                                     975
```

<210> SEQ ID NO 111
<211> LENGTH: 325

<212> TYPE: PRT
<213> ORGANISM: Pseudomonas sp.
<220> FEATURE:
<223> OTHER INFORMATION: Pseudomonas sp. RIT357

<400> SEQUENCE: 111

```
Met Thr Ser Lys Arg Glu Lys Thr Val Ala Ile Val Gln Met Pro Ala
1               5                   10                  15

Ala Leu Leu Asp Arg Ala Glu Ser Met Arg Arg Ala Ala Glu His Ile
            20                  25                  30

Lys Lys Ala Ala Leu Gln Glu Ala Gln Leu Val Ile Phe Pro Glu Thr
        35                  40                  45

Trp Leu Ser Cys Tyr Pro Ala Trp Val Phe Gly Met Ala Gly Trp Asp
    50                  55                  60

Asp Ala Gln Ala Lys Ser Trp Tyr Ala Lys Leu Leu Ala Asp Ser Pro
65                  70                  75                  80

Val Ile Gly Gln Pro Glu Asp Met His Asp Asp Leu Ala Glu Leu Arg
                85                  90                  95

Glu Ala Ala Arg Val Asn Ala Val Thr Val Val Met Gly Met Asn Glu
            100                 105                 110

Arg Ser Arg His His Gly Gly Ser Leu Tyr Asn Ser Leu Val Thr Ile
        115                 120                 125

Gly Pro Asp Gly Ala Ile Leu Asn Val His Arg Lys Leu Thr Pro Thr
    130                 135                 140

His Thr Glu Arg Thr Val Trp Ala Asn Gly Asp Ala Ala Gly Leu Arg
145                 150                 155                 160

Val Val Asp Thr Val Val Gly Arg Val Gly Gly Leu Val Cys Trp Glu
                165                 170                 175

His Trp His Pro Leu Ala Arg Gln Ala Leu His Ala Gln Asp Glu Gln
            180                 185                 190

Ile His Val Ala Ala Trp Pro Asp Met Pro Glu Met His His Val Ala
        195                 200                 205

Ala Arg Ser Tyr Ala Phe Glu Gly Arg Cys Phe Val Leu Cys Ala Gly
    210                 215                 220

Gln Tyr Leu Ala Ala Gly Asp Val Pro Ala Glu Leu Leu Ala Ala Tyr
225                 230                 235                 240

Arg Arg Gly Val Gly Gly Lys Ala Leu Glu Glu Asp Val Leu Phe Asn
                245                 250                 255

Gly Gly Ser Gly Val Ile Ala Pro Asp Gly Ser Trp Val Thr Ala Pro
            260                 265                 270

Leu Phe Gly Glu Pro Gly Ile Ile Leu Ala Thr Ile Asp Leu Ala Gln
        275                 280                 285

Ile Asp Ala Gln His His Asp Leu Asp Val Ala Gly His Tyr Leu Arg
    290                 295                 300

Pro Asp Val Phe Glu Leu Ser Ile Asp Arg Arg Val Arg Thr Gly Leu
305                 310                 315                 320

Thr Leu Arg Asp Ala
                325
```

<210> SEQ ID NO 112
<211> LENGTH: 924
<212> TYPE: DNA
<213> ORGANISM: Nocardia brasiliensis
<220> FEATURE:
<223> OTHER INFORMATION: Nocardia brasiliensis NBRC 14402

<400> SEQUENCE: 112

```
atgcgtattg cagcagcaca ggcccgtccg gcatggctgg accctaccgc tggtaccaaa     60

attgtggtgg attggctgac caaagcagcc gccgcaggtg cagaactggt tgcatttccg    120

gaaacctttc tgagtggcta tccgatttgg ctggcccgta ccggtggtgc acgctttgat    180

aatccggcac agaaagccgc atacgcttat tatctgggcg ccgcagtgac cctggatggt    240

ccgcagctgg ataccgtgcg caccgcagca ggtgacctgg gcgttttctg ttatctgggc    300

attaccgaac gtgttcgtgg taccgtttat tgcaccctgg tggccattga tccggatcgt    360

ggcattgtgg gtgcccatcg caaactgatg ccgacccatg aagaacgtat ggtttggggc    420

attggcgatg gtaatggcct gcgtgcccat gattttggcg tttttcgtgt tagtggcctg    480

agttgttggg aaaattggat gccgcaggcc cgccatgccc tgtatgcaga tggtaccacc    540

ctgcatgtta gcacctggcc gggtagtatt cgtaatacca aagatattac ccgttttatt    600

gccctggaag gtcgtgtgta tagcctggcc gtgggtgccg tgctggatta tgcagatgtg    660

ccgaccgatt ttccgctgta tgaagaactg agcgcactgg ataaaccggc cggctatgat    720

ggcggcagtg ccgtggcagc cccggatggt acctggctgg ttgaaccggt ggtgggcacc    780

gaacgcctga ttctggcaga tttggaccct gccgaagtgg caaaagaacg tcagaatttt    840

gatccgaccg gccattatgc acgcccggat atttttagtg tgaccgtgaa tcgccatcgt    900

cgtaccccgg caacctttct ggat                                            924


<210> SEQ ID NO 113
<211> LENGTH: 308
<212> TYPE: PRT
<213> ORGANISM: Nocardia brasiliensis
<220> FEATURE:
<223> OTHER INFORMATION: Nocardia brasiliensis NBRC 14402

<400> SEQUENCE: 113

Met Arg Ile Ala Ala Ala Gln Ala Arg Pro Ala Trp Leu Asp Pro Thr
1               5                   10                  15

Ala Gly Thr Lys Ile Val Val Asp Trp Leu Thr Lys Ala Ala Ala Ala
            20                  25                  30

Gly Ala Glu Leu Val Ala Phe Pro Glu Thr Phe Leu Ser Gly Tyr Pro
        35                  40                  45

Ile Trp Leu Ala Arg Thr Gly Gly Ala Arg Phe Asp Asn Pro Ala Gln
    50                  55                  60

Lys Ala Ala Tyr Ala Tyr Tyr Leu Gly Ala Ala Val Thr Leu Asp Gly
65                  70                  75                  80

Pro Gln Leu Asp Thr Val Arg Thr Ala Ala Gly Asp Leu Gly Val Phe
                85                  90                  95

Cys Tyr Leu Gly Ile Thr Glu Arg Val Arg Gly Thr Val Tyr Cys Thr
            100                 105                 110

Leu Val Ala Ile Asp Pro Asp Arg Gly Ile Val Gly Ala His Arg Lys
        115                 120                 125

Leu Met Pro Thr His Glu Glu Arg Met Val Trp Gly Ile Gly Asp Gly
    130                 135                 140

Asn Gly Leu Arg Ala His Asp Phe Gly Val Phe Arg Val Ser Gly Leu
145                 150                 155                 160

Ser Cys Trp Glu Asn Trp Met Pro Gln Ala Arg His Ala Leu Tyr Ala
                165                 170                 175

Asp Gly Thr Thr Leu His Val Ser Thr Trp Pro Gly Ser Ile Arg Asn
            180                 185                 190
```

```
Thr Lys Asp Ile Thr Arg Phe Ile Ala Leu Glu Gly Arg Val Tyr Ser
        195                 200                 205

Leu Ala Val Gly Ala Val Leu Asp Tyr Ala Asp Val Pro Thr Asp Phe
    210                 215                 220

Pro Leu Tyr Glu Glu Leu Ser Ala Leu Asp Lys Pro Ala Gly Tyr Asp
225                 230                 235                 240

Gly Gly Ser Ala Val Ala Ala Pro Asp Gly Thr Trp Leu Val Glu Pro
                245                 250                 255

Val Val Gly Thr Glu Arg Leu Ile Leu Ala Asp Leu Asp Pro Ala Glu
            260                 265                 270

Val Ala Lys Glu Arg Gln Asn Phe Asp Pro Thr Gly His Tyr Ala Arg
        275                 280                 285

Pro Asp Ile Phe Ser Val Thr Val Asn Arg His Arg Arg Thr Pro Ala
    290                 295                 300

Thr Phe Leu Asp
305


<210> SEQ ID NO 114
<211> LENGTH: 975
<212> TYPE: DNA
<213> ORGANISM: Defluviimonas alba

<400> SEQUENCE: 114

atgccgacca aaccggttat ccgtgctgct gctgttcaga tcgctccgga cctgatctct      60

cgtgctggta ccatggttaa agttctgaac gctatcgctg acgctgctga caaaggtgct     120

gaattcatcg ttttcccgga aaccttcgtt ccgttctacc cgtacttctc tttcgttctg     180

ccgccggttc agcagggtcc ggaacacctg cgtctgtacg aagaagctgt tgttgttccg     240

tctccggaaa cccgtgctgt tgctgaagct gctcgtaacc gtgctgttgt tgttgttctg     300

ggtgttaacg aacgtgacca gggttctctg tacaacaccc agctgatctt cgacgctgac     360

ggtaccctgg ctctgaaacg tcgtaaaatc accccgacct accacgaacg tatgatctgg     420

ggtcagggtg acggtgctgg tctgaaagtt gttcagacct ctgttggtcg tgttggtgct     480

ctggcttgct gggaacacta caacccgctg gctcgttacg ctctgatggc tcagcacgaa     540

gaaatccacg ctgctcagtt cccgggttct ctggttggtc cgatcttcgg tgaacagatc     600

gaagttacca tgcgtcacca cgctctggaa gctggttgct tcgttgttaa cgctaccggt     660

tggctgaccg aagaacaggt tgctatcatc cacccggacc cgaaactgca gaaaggtctg     720

cgtgacggtt gcatgacctg catcatcacc ccggaaggtc gtcacgctgc tccgccgctg     780

acccacggtg aaggtatcgt tatcgctgac ctggacatga aactgatcac caaacgtaaa     840

cgtatgatgg actctgttgg tcactacgct cgtccggaag ttctgcgtct gatccacgac     900

acccgtccga ccgctccgcg tgaagaatgg gctccggcta tcgacaccgt tgctgctaaa     960

gaaccgtctg acgct                                                      975


<210> SEQ ID NO 115
<211> LENGTH: 325
<212> TYPE: PRT
<213> ORGANISM: Defluviimonas alba

<400> SEQUENCE: 115

Met Pro Thr Lys Pro Val Ile Arg Ala Ala Ala Val Gln Ile Ala Pro
1               5                   10                  15

Asp Leu Ile Ser Arg Ala Gly Thr Met Val Lys Val Leu Asn Ala Ile
            20                  25                  30
```

-continued

```
Ala Asp Ala Ala Asp Lys Gly Ala Glu Phe Ile Val Phe Pro Glu Thr
        35                  40                  45

Phe Val Pro Phe Tyr Pro Tyr Phe Ser Phe Val Leu Pro Pro Val Gln
    50                  55                  60

Gln Gly Pro Glu His Leu Arg Leu Tyr Glu Glu Ala Val Val Val Pro
65                  70                  75                  80

Ser Pro Glu Thr Arg Ala Val Ala Glu Ala Ala Arg Asn Arg Ala Val
                85                  90                  95

Val Val Val Leu Gly Val Asn Glu Arg Asp Gln Gly Ser Leu Tyr Asn
            100                 105                 110

Thr Gln Leu Ile Phe Asp Ala Asp Gly Thr Leu Ala Leu Lys Arg Arg
        115                 120                 125

Lys Ile Thr Pro Thr Tyr His Glu Arg Met Ile Trp Gly Gln Gly Asp
    130                 135                 140

Gly Ala Gly Leu Lys Val Val Gln Thr Ser Val Gly Arg Val Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Ala Ala Gln Phe Pro Gly Ser Leu Val
            180                 185                 190

Gly Pro Ile Phe Gly Glu Gln Ile Glu Val Thr Met Arg His His Ala
        195                 200                 205

Leu Glu Ala Gly Cys Phe Val Val Asn Ala Thr Gly Trp Leu Thr Glu
    210                 215                 220

Glu Gln Val Ala Ile Ile His Pro Asp Pro Lys Leu Gln Lys Gly Leu
225                 230                 235                 240

Arg Asp Gly Cys Met Thr Cys Ile Ile Thr Pro Glu Gly Arg His Ala
                245                 250                 255

Ala Pro Pro Leu Thr His Gly Glu Gly Ile Val Ile Ala Asp Leu Asp
            260                 265                 270

Met Lys Leu Ile Thr Lys Arg Lys Arg Met Met Asp Ser Val Gly His
        275                 280                 285

Tyr Ala Arg Pro Glu Val Leu Arg Leu Ile His Asp Thr Arg Pro Thr
    290                 295                 300

Ala Pro Arg Glu Glu Trp Ala Pro Ala Ile Asp Thr Val Ala Ala Lys
305                 310                 315                 320

Glu Pro Ser Asp Ala
                325
```

METHOD FOR PRODUCTION OF 4-CYANO BENZOIC ACID OR SALTS THEREOF

CROSS-REFERENCE TO RELATED APPLICATIONS

This application is a U.S. National Phase Application of International Patent Application No. PCT/EP2020/051288, filed Jan. 20, 2020, which claims priority to European Patent Application No. 19153038.5, filed Jan. 22, 2019, and which claims priority to European Patent Application No. 19209627.9, filed Nov. 18, 2019, and which claims priority to European Patent Application No. 20152502.9, filed Jan. 17, 2020, the entire contents of which are hereby incorporated by reference herein.

REFERENCE TO AN ELECTRONIC SEQUENCE LISTING

The contents of the electronic sequence listing (2021-07-19 Sequence-Listing 27843-1794.txt; Size: 237,461 bytes; and Date of Creation: Jul. 19, 2021) is herein incorporated by reference in its entirety.

FIELD OF THE INVENTION

The invention is directed to methods for the production of 4-cyano benzoic acid, ammonium 4-cyano benzoic acid or salts thereof from terephthalonitrile using nitrilase as catalyst and compositions comprising 4-cyano benzoic acid.

DESCRIPTION OF THE INVENTION

Nitrilases are a class of enzymes that catalyse the hydration of a nitrile to yield a carboxylic acid. Over the past five decades, various nitrilase-producing organisms, including bacteria, filamentous fungi, yeasts, and plants were described and some of these microbial cell factories were utilized for the commercial production of carboxylic acids in industrial scale. The success of nicotinic acid and (R)-mandelic acid industrial production using nitrilase proved the great economic potential of nitrilase (Gong et al. Microbial Cell Factories 2012, 11, 142-145).

4-cyanobenzoic acid is a common building block for the synthesis of different fungicides belonging to the oxadiazole benzamides class.

The selective enzymatic hydration of terephthalonitrile to produce (ammonium) 4-cyanobenzoic acid has been described in the prior art, however, the number of nitrilases catalysing this reaction is limited and often the production rate and purity of (ammonium) 4-cyanobenzoic acid is hardly sufficient for industrial applications.

Both, the enzymatic and chemical hydrolysis of terephthalonitrile to (ammonium) 4-cyanobenzoic acid, have already been reported in the literature. Enzymatic hydration of nitriles to produce carboxylic acids can be achieved either by a nitrilase or through a biocatalytic cascade involving a nitrile hydratase followed by an amidase.

*Rhodococcus rhodochrous, Rhodococcus equi* and *Aspergillus niger* have been used as whole cell biocatalyst through the nitrile hydratase-amidase cascade (Martinkova et al. Biotech. Lett. 1995, 11, 1219-1222; Bengis-Garber et al. Tetrahedron Lett., 1988, 29, 2589-2590; Šnajdrová et al. J. Mol. Cat. B: Enz. 2004 29 227-232). In these reports, very low concentrations of terephthalonitrile (2-4 mM) were converted to 4-cyanobenzoic acid in high yields (70-95%). Attempts to increase the substrate concentration (25 mM) led to lower yields (62%) (Crosby J. Chem. Soc. Perkin Trans. 1994, 1, 1679-1686). A nitrilase from *Rhodococcus rhodochrous* was also isolated, purified and used as a catalyst for the direct hydrolysis of the nitrile to carboxylic acid (Kobayashi et al. Appl. Microbiol. Biotechnol. 1988, 29, 231-233) in low concentration (6 mM). Recently a patent (CN107641622, 2018) has been published claiming the use of different nitrilases (from *Pantoea* sp., *Arabidopsis thaliana, Acidovorax facilis, Leptolyngbya* sp., *Brassica oleracea* and *Camelina sativa*) to produce (ammonium) 4-cyanobenzoic acid in high concentration (100 g/L) and yield (86-95%). In this patent, the biotransformation is carried out in a mixture of phosphate buffer and DMSO (90:10) using relatively a high concentration of enzyme.

It is also possible to selectively hydrolyse terephthalonitrile chemically using sodium hydroxide at 80° C. followed by sodium nitrite, acetic acid and acetic anhydride addition. 4-cyanobenzoic acid can be isolated in 72% yield and 95% purity (U.S. Pat. No. 6,433,211).

This invention provides nitrilases catalysing the reaction from terephthalonitrile to (ammonium) 4-benzoic acid, especially nitrilases that are catalysing this reaction in high substrate concentration with high yield and purity.

The nitrilases of the invention catalyze the conversion of terephthalonitrile to 4-cyanobenzoic acid as the main reaction. Further hydrolysis of the second nitrile group results in terephthalic acid as an unwanted byproduct. Excessive amounts of terephthalic acid shall be avoided as terephthalic acid removal in later process steps is difficult. Reduction of the terephthalic acid content in the reaction mixture thus improves the economic viability of the process as it leads to a reduction for cost of goods and less process operations.

Therefore this invention further provides compositions having a high 4-benzoic acid and a low terephthalic acid content.

DETAILED DESCRIPTION OF THE INVENTION

It is one aim of the invention to provide nitrilases having higher activity, preferably higher specific activity and resulting in higher product concentration in shorter time in the aqueous medium, preferably after shorter incubation time than described in the prior art.

Hence one embodiment of the invention is an isolated nitrilase capable of catalysing the reaction from terephthalonitrile to (ammonium) 4-cyano benzoic acid in an aqueous medium comprising water, nitrilase and terephthalonitrile and/or (ammonium) 4-cyano benzoic acid, wherein the concentration of (ammonium) 4-cyano benzoic acid in the aqueous medium after incubation is at least 5% or 5.5% (w/w), preferably at least 6% or 6.5%, preferably 7% or 7.5%, preferable 8% or 8.5%, preferably 9% or 9.5%, preferably at least 10%, 10.5%, 11%, 11.5%, 12%, 12.5%, more preferably at least 13% or 13.5%, even more preferably at least 14% or 14.5%, most preferably at least 15% and the concentration of terephthalonitrile is below 1.0% (w/w), preferably below 0.9%, 0.8%, 0.7%, more preferably below 0.6%, most preferably below 0.5%.

In another embodiment of the invention, the isolated nitrilase is comprising a sequence selected from the group consisting of

- The amino acid molecule of SEQ ID NO: 2, 4, 6 and 8, and
- An amino acid molecule having at least 40% identity to the amino acid molecule of SEQ ID NO: 2, 4, 6 or 8 or a functional fragment thereof, and An amino acid molecule encoded by a nucleic acid molecule of SEQ ID NO: 1, 3, 5 or 7 or a functional fragment thereof, and An amino acid molecule encoded by a nucleic acid molecule having at least 40% identity to SEQ ID NO: 1, 3, 5 or 7 or a functional fragment thereof, and An amino acid molecule encoded by a nucleic acid molecule hybridizing under stringent conditions to a fragment of at least 250 bases complementary to SEQ ID NO: 1, 3, 5 or 7 or a functional fragment thereof, wherein the amino acid molecule as defined in b., d. and e. is catalysing the reaction from terephthalonitrile to (ammonium) 4-cyano benzoic acid in an aqueous medium and wherein the concentration of 4-cyano benzoic acid in the aqueous medium after incubation is at least 9% or 9.5% (w/w), preferably at least 10%, 10.5%, 11%, 11.5%, 12%, 12.5%, more preferably at least 13% or 13.5%, even more preferably at least 14% or 14.5%, most preferably at least 15% and the concentration of terephthalonitrile is below 1.0% (w/w), preferably below 0.9%, 0.8%, 0.7%, more preferably below 0.6%, most preferably below 0.5%.

A further embodiment of the invention is a process for producing 4-cyano benzoic acid or salt thereof comprising the steps of i. Providing an aqueous medium comprising water, one or more nitrilase and terephthalonitrile,
ii. Incubating the aqueous medium and
iii. Optionally isolating the 4-cyano benzoic acid or salt thereof from the reaction mixture, wherein the one or more nitrilase is capable of catalysing the reaction from terephthalonitrile to ammonium 4-cyano benzoic acid in an aqueous medium comprising water, nitrilase and terephthalonitrile and/or ammonium 4-cyano benzoic acid, wherein the concentration of 4-cyano benzoic acid in the aqueous medium after incubation is at least 5% or 5.5% (w/w), preferably at least 6% or 6.5%, preferably at least 7% or 7.5%, preferably at least 8% or 8.5%, preferably 9% or 9.5% (w/w), preferably at least 10%, 10.5%, 11%, 11.5%, 12%, 12.5%, more preferably at least 13% or 13.5%, even more preferably at least 14% or 14.5%, most preferably at least 15% and the concentration of terephthalonitrile is below 1.0% (w/w), preferably below 0.9%, 0.8%, 0.7%, more preferably below 0.6%, most preferably below 0.5%.

In one embodiment of the process of the invention the nitrilase is comprising a sequence selected from the group consisting of a. The amino acid molecule of SEQ ID NO: 2, 4, 6 and 8, and
b. An amino acid molecule having at least 55% identity to the amino acid molecule of SEQ ID NO: 2, 4, 6 or 8 or a functional fragment thereof, and
c. An amino acid molecule encoded by a nucleic acid molecule of SEQ ID NO: 1, 3, 5 or 7 or a functional fragment thereof, and
d. An amino acid molecule encoded by a nucleic acid molecule having at least 70% identity to SEQ ID NO: 1, 3, 5 or 7 or a functional fragment thereof, and
e. An amino acid molecule encoded by a nucleic acid molecule hybridizing under stringent conditions to a fragment of at least 250 bases complementary to SEQ ID NO: 1, 3, 5 or 7 or a functional fragment thereof, wherein the amino acid molecule as defined in b., d. and e. is catalysing the reaction from terephthalonitrile to ammonium 4-cyano benzoic acid in an aqueous medium comprising water, nitrilase and terephthalonitrile and/or ammonium 4-cyano benzoic acid, wherein the concentration of 4-cyano benzoic acid in the aqueous medium after incubation is at least 5% or 5.5% (w/w), preferably at least 6% or 6.5%, preferably at least 7% or 7.5%, preferably at least 8% or 8.5%, preferably at least 9% or 9.5% (w/w), preferably at least 10%, 10.5%, 11%, 11.5%, 12%, 12.5%, more preferably at least 13% or 13.5%, even more preferably at least 14% or 14.5%, most preferably at least 15% and the concentration of terephthalonitrile is below 1.0% (w/w), preferably below 0.9%, 0.8%, 0.7%, more preferably below 0.6%, most preferably below 0.5%.

One embodiment of the invention is a process for producing (ammonium) 4-cyano benzoic acid comprising the steps of providing an aqueous medium comprising water or a buffer having a pH of 4 to 9, one or more nitrilases and terephthalonitrile, incubating the aqueous medium and optionally isolating the (ammonium) 4-cyano benzoic acid from the reaction mixture, wherein the one or more nitrilase is selected from the group consisting of an amino acid molecule of SEQ ID NO: 2, 4, 6, 8, 10, 12, 14, 16, 20 and 22, or a functional fragment thereof, and an amino acid molecule having at least 40% identity to the amino acid molecule of SEQ ID NO: SEQ ID NO: 2, 4, 6, 8, 10, 12, 14, 16, 20 or 22 or a functional fragment thereof, and, an amino acid molecule encoded by a nucleic acid molecule of SEQ ID NO 1, 3, 5, 7, 9, 11, 13, 15, 19 or 21 or a functional fragment thereof, and an amino acid molecule encoded by a nucleic acid molecule having at least 40% identity to SEQ ID NO: 1, 3, 5, 7, 9, 11, 13, 15, 19 or 21 or a functional fragment thereof, and an amino acid molecule encoded by a nucleic acid molecule hybridizing under stringent conditions to a fragment of at least 250 bases complementary to SEQ ID NO 1, 3, 5, 7, 9, 11, 13, 15, 19 or 21 or a functional fragment thereof, wherein the amino acid molecule as defined in ii., iv. and v. have the activity of converting terephthalonitrile to (ammonium) 4-cyano benzoic acid and wherein the concentration of (ammonium) 4-cyano benzoic acid in the aqueous medium after incubation is at least 5% or 5.5% (w/w), preferably at least 6% or 6.5%, preferably at least 7% or 7.5%, preferably at least 8% or 8.5%, preferably at least 9% or 9.5% (w/w), preferably at least 10%, 10.5%, 11%, 11.5%, 12%, 12.5%, more preferably at least 13% or 13.5%, even more preferably at least 14% or 14.5%, most preferably at least 15% and the concentration of terephthalonitrile is below 1.0% (w/w), preferably below 0.9%, 0.8%, 0.7%, more preferably below 0.6%, most preferably below 0.5%.

In table 1 examples for functional variants of the amino acid molecules of SEQ ID 2, 4, 6, 8, 10, 12, 14, 18, 20 and 22 are listed having a certain identity to the respective SEQ ID. Further the SEQ ID of the respective nucleic acid are listed encoding the respective functional variant amino acid molecule.

TABLE 1

| Seq. ID | Donor | SEQ ID amino acid | SEQ ID nucleic acid | Identity |
|---|---|---|---|---|
| 2 | *Comamonas testosteroni* | 29 | 28 | 90% |
| | | 31 | 30 | 85% |
| | | 33 | 32 | 80% |
| 4 | Unknown prokaryotic organism | 35 | 34 | 90% |
| | | 37 | 36 | 85% |
| | | 39 | 38 | 80% |
| 6 | *Agrobacterium rubi* | 41 | 40 | 90% |
| | | 43 | 42 | 85% |
| | | 45 | 44 | 80% |
| 8 | *Candidatus* Dadabacteria bacterium CSP1-2 | 47 | 46 | 90% |
| | | 49 | 48 | 85% |
| | | 51 | 50 | 80% |
| 10 | *Tepidicaulis marinus* | 53 | 52 | 90% |
| | | 55 | 54 | 85% |
| | | 57 | 56 | 80% |
| 12 | *Sphingomonas wittichii* RW1 | 59 | 58 | 90% |
| | | 61 | 60 | 85% |
| | | 63 | 62 | 80% |
| 14 | *Rhizobium* sp. YK2 | 65 | 64 | 90% |
| | | 67 | 66 | 85% |
| | | 69 | 68 | 80% |
| | | 83 | 70 | 90% |
| | | 85 | 72 | 85% |
| | | 87 | 74 | 80% |
| 16 | Synechococcus sp. CC9605 | 71 | 76 | 90% |
| | | 73 | 78 | 85% |
| | | 75 | 80 | 80% |
| | *Tatumella morbirosei* | 77 | 82 | 90% |
| | | 79 | 84 | 85% |
| | | 81 | 86 | 80% |
| 20 | *Flavihumibacter solisilvae* | 89 | 88 | 90% |
| | | 91 | 90 | 85% |
| | | 93 | 92 | 80% |
| 22 | *Salinisphaera shabanensis* E1L3A | 95 | 94 | 90% |
| | | 97 | 96 | 85% |
| | | 99 | 98 | 80% |

The aqueous medium may be a solution or a suspension or a solution and a suspension, wherein any of the substances comprised in said aqueous medium may be fully or partially dissolved and/or partially or fully suspended.

The aqueous medium preferably further comprises a divalent cation, for example $Mg^{2+}$, $Mn^{2+}$, $Ca^{2+}$, $Fe^{2+}$, $Zn^{2+}$ or $Co^{2+}$. Preferably the divalent cation is $Mg^{2+}$ or $Mn^{2+}$, most preferably, the divalent cation is $Mg^{2+}$.

The divalent cation may have a concentration of 1 mM to 500 mM, for example 10 mM to 450 mM. Preferably the concentration of the divalent cation is between 20 mM and 400 mM, preferably between 30 mM and 300 mM, more preferably between 40 mM and 250 mM, more preferably between 40 mM and 200 mM, most preferably between 40 mM and 150 mM.

In a preferred embodiment of the process for producing (ammonium) 4-cyano benzoic acid, the incubation is performed at 10° C. to 50° C., preferably at 15° C. to 40° C., more preferably at 20° C. to 40° C., even more preferably at 24° C. to 37° C., even more preferably at 28° C. to 36° C., even more preferably at 29° C. to 24° C., most preferably at 30° C. to 33° C.

In a preferred embodiment, the incubation is performed for 30 minutes to 48 hours, preferably for 1 hour to 36 hours, more preferably for 2 hours to 24 hours, most preferably for 3 hours to 15 hours.

In a preferred embodiment of the process for producing (ammonium) 4-cyano benzoic acid, the method is carried out using a batch process.

At the start of the process of the invention, the aqueous medium may comprise at least 0.05% terephthalonitrile, preferably at least 0.1% terephthalonitrile, more preferably at least 0.5% terephthalonitrile, most preferably at least 1.0% terephthalonitrile (w/w). Throughout the incubation the concentration of terephthalonitrile may be kept at a concentration of about 0.5% to 1.5%, preferably about 1.0% terephthalonitrile by continuous feeding of terephthalonitrile.

Alternatively, the concentration of terephthalonitrile in the aqueous medium may be between including 1 wt % to 30 wt % at the start of the incubation, preferably between including 5 wt % to 10 wt %, even more preferably between including 6 wt % to 9 wt %, most preferably between including 7 wt % to 8.5 wt %.

The incubation time of the aqueous medium may be at least 2 h, at least 5 h, at least 10 h or at least 12 h. Preferably the incubation time is at least 18 h, for example about 24 h or about 30 h. More preferably the incubation time is about 36 h or about 42 h. Most preferably, the incubation time is about 48 h. Depending on the nitrilase used and the reaction rate of said nitrilase, the incubation time may also exceed 48 h.

The aqueous medium may be incubated at at least 15° C., at least 20° C., at least 24° C. or at least 28° C. Preferably the aqueous medium is incubated between including 27° C. and 38° C. Most preferably the aqueous medium is incubated at 30° C. The aqueous medium may also be incubated at 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

In a preferred embodiment, the method is carried out using a batch process.

In a preferred embodiment of the process for producing (ammonium) 4-cyano benzoic acid, an acid, for example HCl, $H_2SO_4$, $H_3PO_4$ or the like is added to the aqueous medium after incubation in order to transfer the resulting (ammonium) 4-cyano benzoic acid to the respective acid which leads to precipitation of the acid facilitating fast and easy isolation of the product.

The nitrilase used in the process of the invention may be isolated from the organism naturally expressing said nitrilase. Alternatively, the nitrilase may be added to the aqueous medium by adding cells comprising said nitrilase or by adding a suspension comprising inactivated, for example disrupted cells. In another embodiment of the invention, the nitrilase may be produced in recombinant organisms, preferably microorganisms, expressing the nitrilase of the invention from a heterologous construct. The nitrilase so produced may be isolated from the recombinant organism and added to the aqueous medium or the nitrilase may be added by inactivating, for example disrupting the cells and adding the suspension.

The cells or suspension comprising inactivated cells may be at least partially concentrated for example by drying before being added to the aqueous medium used in the methods of the invention or to the composition of the invention.

The nitrilase may be (partly) immobilized for instance entrapped in a gel or it may be used for example as a free cell suspension. For immobilization well known standard methods can be applied like for example entrapment cross linkage such as glutaraldehyde-polyethyleneimine (GA-PEI) crosslinking, cross linking to a matrix and/or carrier binding etc., including variations and/or combinations of the aforementioned methods. Alternatively, the nitrilase enzyme may be extracted and for instance may be used directly in the process for preparing the ammonium salt or the acid. When using inactivated or partly inactivated cells, such cells may be inactivated by thermal or chemical treatment.

A further embodiment of the invention is an isolated nitrilase comprising a sequence selected from the group consisting of an amino acid molecule of SEQ ID NO: 2, 4, 6, 8, 10, 12, 14, 16, 20 and 22 or a functional fragment thereof, and

- an amino acid molecule having at least 40% identity to the amino acid molecule of SEQ ID NO: SEQ ID NO: 2, 4, 6, 8, 10, 12, 14, 16, 20 or 22 or a functional fragment thereof, and,
- an amino acid molecule encoded by a nucleic acid molecule of SEQ ID NO 1, 3, 5, 7, 9, 11, 13, 15, 19 or 21 or a functional fragment thereof, and
- an amino acid molecule encoded by a nucleic acid molecule having at least 40% identity to SEQ ID NO: 1, 3, 5, 7, 9, 11, 13, 15, 19 or 21 or a functional fragment thereof, and
- an amino acid molecule encoded by a nucleic acid molecule hybridizing under stringent conditions to a fragment of at least 250 bases complementary to SEQ ID NO 1, 3, 5, 7, 9, 11, 13, 15, 19 or 21 or a functional fragment thereof,
- wherein the amino acid molecule as defined in b., d. and e. is catalysing the reaction from terephthalonitrile to (ammonium) 4-cyano benzoic acid in an aqueous medium.

A further embodiment of the invention is a recombinant construct comprising a nitrilase wherein the nitrilase is selected from the group consisting of an amino acid molecule of SEQ ID NO: 2, 4, 6, 8, 10, 12, 14, 16, 20 and 22 or a functional fragment thereof, and

- an amino acid molecule having at least 40% identity to the amino acid molecule of SEQ ID NO: SEQ ID NO: 2, 4, 6, 8, 10, 12, 14, 16, 20 or 22 or a functional fragment thereof, and,
- an amino acid molecule encoded by a nucleic acid molecule of SEQ ID NO 1, 3, 5, 7, 9, 11, 13, 15, 19 or 21 or a functional fragment thereof, and
- an amino acid molecule encoded by a nucleic acid molecule having at least 40% identity to SEQ ID NO: 1, 3, 5, 7, 9, 11, 13, 15, 19 or 21 or a functional fragment thereof, and
- an amino acid molecule encoded by a nucleic acid molecule hybridizing under stringent conditions to a fragment of at least 250 bases complementary to SEQ ID NO 1, 3, 5, 7, 9, 11, 13, 15, 19 or 21 or a functional fragment thereof,
- wherein the amino acid molecule as defined in ii., iv. and v. is catalysing the reaction from terephthalonitrile to (ammonium) 4-cyano benzoic acid in an aqueous medium.

Said recombinant construct may be integrated into the genome of an organism for producing and isolating the respective nitrilase or the nitrilase may be expressed from a vector such as a plasmid or viral vector that is introduced into an organism for producing and isolating said nitrilase.

The nitrilase in the recombinant construct may be functionally linked to a heterologous promoter, a heterologous terminator or any other heterologous genetic element.

A further embodiment of the invention is a recombinant vector, such a s an expression vector or a viral vector comprising said recombinant construct.

A recombinant microorganism comprising said recombinant construct or said recombinant vector is also an embodiment of the invention.

In some embodiments, the recombinant microorganism is a prokaryotic cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp and so forth.

In some embodiments, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as

*Schwanniomyces occidentalis, Arxula* spec, such as *Arxula adeninivorans, Ogataea* spec such as *Ogataea minuta, Klebsiella* spec, such as *Klebsiella pneumonia.*

A microorganism of the genus *Comamonas testosteroni, Agrobacterium rubi, Candidatus* Dadabacteria bacterium, *Tepidicaulis marinus, Sphingomonas wittichii, Rhizobium* spec., *Synechococcus* sp. CC9605, *Tatumella morbirosei, Flavihumibacter solisilvae* or *Salinisphaera shabanensis* E1L3A expressing any of the nitrilases of the invention is another embodiment of the invention.

A further embodiment of the invention is a method for producing a nitrilase, comprising the steps of a) providing a recombinant microorganism expressing at least one of the nitrilases of the invention or a microorganism naturally expressing a nitrilase of the invention, and b) cultivating said microorganism under conditions allowing for the expression of said nitrilase gene, and c) optionally isolating the nitrilase of the invention from said microorganism.

Another embodiment of the invention is a composition comprising water, a nitrilase, terephthalonitrile and/or (ammonium) 4-cyano benzoic acid wherein the nitrilase is selected from the group consisting of an amino acid molecule of SEQ ID NO: 2, 4, 6, 8, 10, 12, 14, 16, 20 and 22 or a functional fragment thereof, and an amino acid molecule having at least 40% identity to the amino acid molecule of SEQ ID NO: SEQ ID NO: 2, 4, 6, 8, 10, 12, 14, 16, 20 or 22, and, an amino acid molecule encoded by a nucleic acid molecule of SEQ ID NO 1, 3, 5, 7, 9, 11, 13, 15, 19 or 21 or a functional fragment thereof, and an amino acid molecule encoded by a nucleic acid molecule having at least 40% identity to SEQ ID NO: 1, 3, 5, 7, 9, 11, 13, 15, 19 or 21 or a functional fragment thereof, and an amino acid molecule encoded by a nucleic acid molecule hybridizing under stringent conditions to a fragment of at least 250 bases complementary to SEQ ID NO 1, 3, 5, 7, 9, 11, 13, 15, 19 or 21 or a functional fragment thereof, wherein the amino acid molecule as defined in ii., iv. and v. is catalysing the reaction from terephthalonitrile to (ammonium) 4-cyano benzoic acid in an aqueous medium.

Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W Amino acid molecules and nucleic acid molecules having a certain identity to any of the sequences of SEQ ID NO 1 to 22 include nucleic acid molecules and amino acid molecules having 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to any of SEQ ID NO:1 to 22.

Preferably, the nitrilase amino acid sequences having a certain identity to the nitrilases of SEQ ID NO: 2, 4, 6, 8, 10, 12, 14, 20 and 22 comprise some, preferably predominantly, more preferably only conservative amino acid substitutions. Conservative substitutions are those where one amino acid is exchanged with a similar amino acid. For determination of %-similarity the following applies, which is also in accordance with the BLOSUM62 matrix, which is one of the most used amino acids similarity matrix for database searching and sequence alignments:

Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

A functional fragment of the amino acid molecules selected from SEQ ID NO: 2, 4, 6, 8, 10, 12, 14, 20 and 22 comprises at least 100 amino acids, preferably at least 150 amino acids, more preferably at least 200 amino acids, more preferably at least 250 amino acids, most preferably at least 300 amino acids.

A further embodiment of the invention is a composition consisting of 95.0 wt % to 99.5 wt % 4-cyano benzoic acid, preferably 95.0 wt % to 99.25 wt %, preferably 95.0 wt % to 99.0 wt %, more preferably 96.0 wt % to 99.5 wt %, more preferably 97.0 wt % to 99.5 wt %, more preferably 97.25 wt % to 99.5 wt %, more preferably 97.5 wt % to 99.5 wt %, more preferably 97.75 wt % to 99.5 wt %, even more preferably 96.0 wt % to 99.25 wt %, more preferably 97.0 wt % to 99.0 wt %, more preferably 97.25 wt % to 99.0 wt %, more preferably 97.5 wt % to 98.5 wt %, even more preferably 97.75 wt % to 98.25 wt %, even more preferably 97.9 wt % to 98.1 wt %, even more preferably 97.0 wt % to 99.5 wt %, most preferably 97.3 wt % to 99.25 wt %, 0.0 wt % to 0.5 wt % terephtalic acid, preferably 0.0 wt % to 0.45 wt %, more preferably 0.0 wt % to 4.0 wt %, even more preferably 0.0 wt % to 0.35 wt %, even more preferably 0.0 wt % to 0.3 wt %, even more preferably 0.1 wt % to to 0.5 wt % terephtalic acid, preferably 0.1 wt % to 0.45 wt %, even more preferably 0.1 wt % to 0.4 wt %, even more preferably 0.1 wt % to 0.35 wt %, even more preferably 0.1 wt % to 0.3 wt %, even more preferably 0.2 wt % to 0.5 wt % terephtalic acid, even more preferably 0.2 wt % to 0.45 wt %, even more preferably 0.2 wt % to 0.4 wt %, even more preferably 0.2 wt % to 0.35 wt %, even more preferably 0.2 wt % to 0.3 wt %, even more preferably 0.3 wt % to 0.5 wt % terephtalic acid, even more preferably 0.3 wt % to 0.45 wt %, even more preferably 0.3 wt % to 0.4 wt %, even more preferably 0.3 wt % to 0.35 wt %, even more preferably 0.3 wt % to 0.325 wt %, most preferably 0.275 wt % to 0.325 wt %, 0.2 wt % to 1.5 wt % chloride, preferably 0.2 wt % to 1.25 wt %, more preferably 0.2 wt % to 1.0 wt %, more preferably 0.3 wt % to 1.5 wt % chloride, preferably 0.3 wt % to 1.25 wt %, more preferably 0.3 wt % to 1.0 wt %, more preferably 0.25 wt % to 1.5 wt % chloride, preferably 0.25 wt % to 1.25 wt %, more preferably 0.25 wt % to 1.0 wt %, up to 0.3 wt % water, preferably up to 0.2 wt % water, preferably up to 0.1 wt % water, preferably up to 0.05 wt % water, preferably 0.05 wt % to 0.2 wt % water, preferably 0.075 wt % to 0.2 wt %, more preferably 0.1 wt % to 0.2 wt %, even more preferably 0.05 wt % to 0.3 wt % water, preferably 0.075 wt % to 0.3 wt %, more preferably 0.1 wt % to 0.3 wt %, and optionally up to 4.8 wt % other components. The other components comprise for example ammonium, phosphate, terephthalonitrile or contaminants from the fermentation process. In total, the components sum up to 100%.

A further embodiment of the invention is a composition consisting of 95.0 wt % to 97.0 wt % 4-cyano benzoic acid, preferably 95.25 wt % to 97.0 wt %, preferably 95.5 wt % to 97.0 wt %, preferably 95.75 wt % to 97.0 wt % 4-cyano benzoic acid, more preferably 95.0 wt % to 96.75 wt %, more preferably 95.0 wt % to 96.5 wt %, more preferably 95.0 wt % to 96.25 wt % 4-cyano benzoic acid, even more preferably 95.25 wt % to 96.75 wt %, more preferably 95.5 wt % to 96.5 wt %, more preferably 95.75 wt % to 96.25 wt % 4-cyano benzoic acid, 0.0 wt % to 0.5 wt % terephtalic acid, preferably 0.0 wt % to 0.45 wt %, more preferably 0.0 wt % to 4.0 wt %, even more preferably 0.0 wt % to 0.35 wt %, even more preferably 0.0 wt % to 0.3 wt %, even more preferably 0.1 wt % to to 0.5 wt % terephtalic acid, preferably 0.1 wt % to 0.45 wt %, even more preferably 0.1 wt % to 0.4 wt %, even more preferably 0.1 wt % to 0.35 wt %, even more preferably 0.1 wt % to 0.3 wt %, even more preferably 0.2 wt % to 0.5 wt % terephtalic acid, even more preferably 0.2 wt % to 0.45 wt %, even more preferably 0.2 wt % to 0.4 wt %, even more preferably 0.2 wt % to 0.35 wt %, even more preferably 0.2 wt % to 0.3 wt %, even more preferably 0.3 wt % to 0.5 wt % terephtalic acid, even more preferably 0.3 wt % to 0.45 wt %, even more preferably 0.3 wt % to 0.4 wt %, even more preferably 0.3 wt % to 0.35 wt %, even more preferably 0.3 wt % to 0.325 wt %, most preferably 0.275 wt % to 0.325 wt % terephtalic acid, 0.3 wt % to 1.5 wt % ammonium, preferably 0.35 wt % to 1.25 wt %, more preferably 0.4 wt % to 1.0 wt %, even more preferably 0.5 wt % to 0.75 wt %, even more preferably 0.55 wt % to 0.7 wt %, most preferably 0.55 wt % to 0.65 wt % ammonium, 2.0 wt % to 0.4 wt % sulfate, preferably 2.25 wt % to 0.375 wt %, more preferably 2.5 wt % to 3.5 wt %, even more preferably 2.75 wt % to 3.25 wt %, most preferably 2.9 wt % to 3.2 wt % sulfate 0.4 wt % to 1.0 wt % natrium, preferably 0.5 wt % to 0.9 wt %, more preferably 0.6 wt % to 0.8 wt %, even more preferably 0.65 wt % to 0.75 wt % natrium and optionally up to 2.3 wt % other components. The other components comprise for example water, chloride, phosphate, terephthalonitrile or contaminants from the fermentation process. In total, the components sum up to 100%.

A further embodiment of the invention is a method for making an aqueous solution containing at least 5% or 5.5% (w/w), preferably at least 6% or 6.5%, preferably at least 7% or 7.5%, preferably at least 8% or 8.5%, preferably at least 9% or 9.5% (w/w), preferably at least 10%, 10.5%, 11%, 11.5%, 12%, 12.5%, more preferably at least 13% or 13.5%, even more preferably at least 14% or 14.5%, most preferably at least 15% (ammonium) 4-cyano benzoic acid and the concentration of terephthalonitrile is below 1.0% (w/w), preferably below 0.9%, 0.8%, 0.7%, more preferably below 0.6%, most preferably below 0.5%. And the concentration of terephtalic acid is below 0.5 wt %, preferably below 0.45 wt %, more preferably below 0.4 wt %, even more preferably below 0.35 wt % even more preferably the concentration is 0.29 wt % to 0.31 wt %, comprising the steps of Providing an aqueous medium comprising water, one or more nitrilase and terephthalonitrile and Incubating the aqueous medium, Wherein the nitrilase is capable of catalysing the reaction from terephthalonitrile to 4-cyano benzoic acid in an aqueous medium.

In one embodiment of the method of the invention the aqueous medium further comprises a divalent cation. The divalent cation may for example be one or more of $Mg^{2+}$, $Mn^{2+}$, $Ca^{2+}$, $Fe^{2+}$, Zn2+ or Co2+.

The divalent cation may have a concentration of 1 mM to 500 mM, for example 10 mM to 450 mM. Preferably the concentration of the divalent cation is between 20 mM and 400 mM, preferably between 30 mM and 300 mM, more preferably between 40 mM and 250 mM, more preferably between 40 mM and 200 mM, most preferably between 40 mM and 150 mM.

In a preferred embodiment of the process for producing (ammonium) 4-cyano benzoic acid, the incubation is performed at 10° C. to 50° C., preferably at 15° C. to 40° C., more preferably at 20° C. to 40° C., even more preferably at 24° C. to 37° C., even more preferably at 28° C. to 36° C., even more preferably at 29° C. to 24° C., most preferably at 30° C. to 33° C.

In a preferred embodiment, the incubation is performed for 30 minutes to 48 hours, preferably for 1 hour to 36 hours, more preferably for 2 hours to 24 hours, most preferably for 3 hours to 15 hours.

At the start of the method of the invention, the aqueous medium may comprise at least 0.05% terephthalonitrile, preferably at least 0.1% terephthalonitrile, more preferably at least 0.5% terephthalonitrile, most preferably at least 1.0% terephthalonitrile (w/w). Throughout the incubation the concentration of terephthalonitrile may be kept at a concentration of about 0.5% to 1.5%, preferably about 1.0% terephthalonitrile by continuous feeding of terephthalonitrile.

Alternatively, the concentration of terephthalonitrile in the aqueous medium may be between including 1 wt % to 30 wt % at the start of the incubation, preferably between including 5 wt % to 10 wt %, even more preferably between including 6 wt % to 9 wt %, most preferably between including 7 wt % to 8.5 wt %.

The incubation time of the aqueous medium may be at least 2 h, at least 5 h, at least 10 h or at least 12 h. Preferably the incubation time is at least 18 h, for example about 24 h or about 30 h. More preferably the incubation time is about 36 h or about 42 h. Most preferably, the incubation time is about 48 h. Depending on the nitrilase used and the reaction rate of said nitrilase, the incubation time may also exceed 48 h.

The aqueous medium may be incubated at at least 15° C., at least 20° C., at least 24° C. or at least 28° C. Preferably the aqueous medium is incubated between including 27° C. and 38° C. Most preferably the aqueous medium is incubated at 30° C. The aqueous medium may also be incubated at 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

In one embodiment of the method of the invention the pH-value of the aqueous medium is adjusted to below 5 by adding acid to the aqueous medium during or after incubation.

In one embodiment of the method of the invention the product is isolated by filtration or centrifugation after incubation.

In one embodiment of the method of the invention the nitrilase is produced by fermentation.

Definitions

It is to be understood that this invention is not limited to the particular methodology or protocols. It is also to be understood that the terminology used herein is for the purpose of describing particular embodiments only and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as start codon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, densitometric measurement of nucleic acid concentration in a gel, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional fragment: The term "functional fragment" refers to any nucleic acid or amino acid sequence which comprises merely a part of the full length nucleic acid or full length amino acid sequence, respectively, but still has the same or similar activity and/or function. In one embodiment, the fragment comprises at least 70%, at least 80%, at least 85%, at least 90%, at least 95%, at least 96%, at least 97%, at least 98%, at least 99% of the original sequence. In one embodiment, the functional fragment comprises contiguous nucleic acids or amino acids compared to the original nucleic acid or original amino acid sequence, respectively.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., Sambrook J, Fritsch E F and Maniatis T (1989); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitrocellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered.

Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA hybrids (Meinkoth and Wahl, Anal. Biochem., 138: 267-284, 1984):

$$Tm=81.5° C.+16.6\times\log[Na+]a+0.41x\%[G/Cb]-500x[Lc]-1-0.61x\% \text{ formamide}$$

DNA-RNA or RNA-RNA hybrids:

$$Tm=79.8+18.5(\log 10[Na+]a)+0.58(\% G/Cb)+11.8(\% G/Cb)2-820/Lc$$

oligo-DNA or oligo-RNAd hybrids:

For <20 nucleotides: Tm=2 (In)

For 20-35 nucleotides: Tm=22+1.46 (In)

a or for other monovalent cation, but only accurate in the 0.01-0.4 M range.

b only accurate for % GC in the 30% to 75% range.

c L=length of duplex in base pairs.

d Oligo, oligonucleotide; In, effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 μg/ml denatured, fragmented salmon sperm DNA, 0.5% sodium pyrophosphate, followed by the washing at 65° C. in 0.3×SSC.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

"Identity": "Identity" when used in respect to the comparison of two or more nucleic acid or amino acid molecules means that the sequences of said molecules share a certain degree of sequence similarity, the sequences being partially identical.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

```
Seq A: AAGATACTG length: 9 bases

Seq B: GATCTGA length: 7 bases
```

Hence, the shorter sequence is sequence B.

Producing a pairwise global alignment which is showing both sequences over their complete lengths results in

```
Seq A: AAGATACTG-
         ||| |||
Seq B: --GAT-CTGA
```

The "|" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
         ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

After aligning two sequences, in a second step, an identity value is determined from the alignment produced. For purposes of this description, percent identity is calculated by %-identity=(identical residues/length of the alignment region which is showing the respective sequence of this invention over its complete length)*100. Thus, sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity". According to the example provided above, %-identity is: for Seq A being the sequence of the invention (6/9)*100=66.7%; for Seq B being the sequence of the invention (6/8)*100=75%.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single- or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Nitrilase: The term "nitrilase" as used herein refers to an enzyme catalyzing the reaction from terephthalonitrile to 4-cyano benzoic acid and/or the reaction from terephthalonitrile to ammonium 4-cyano benzoic acid. It also encompasses enzymes that are catalyzing additional reactions despite those mentioned before.

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single- or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or-5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with at least one recombinant nucleic acid molecule.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, dsRNA) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

An example of such a recombinant nucleic acid molecule is a plasmid into which a heterologous DNA-sequence has been inserted or a gene or promoter which has been mutated compared to the gene or promoter from which the recombinant nucleic acid molecule derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

FIGURES

FIG. 1 shows the reaction catalyzed by the nitrilases of the invention.

Figure 2:
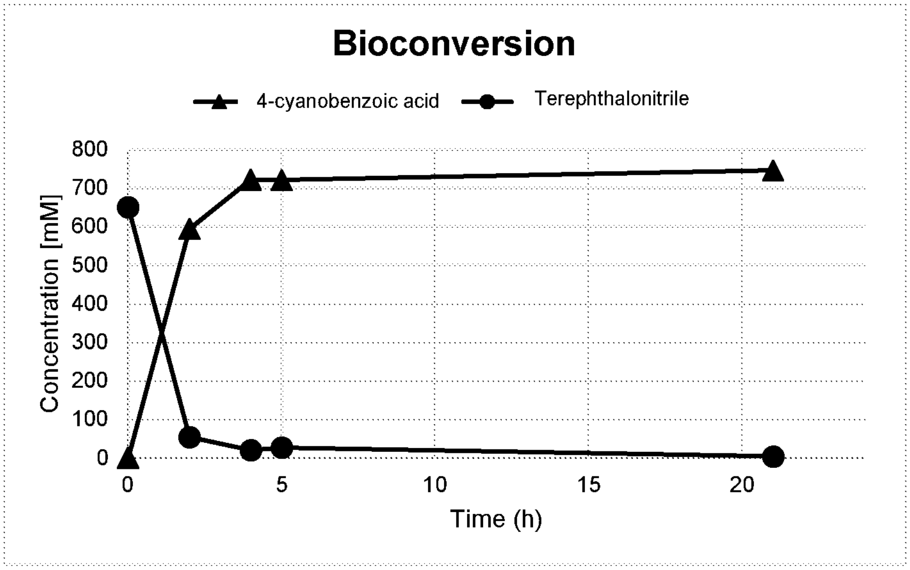

FIG. 2: Bioconversion of terephthalonitrile by heterologous *E. coli* cells expressing the nitrilase from *Comamonas testosteroni* (Seq. ID 2).

EXAMPLES

Example 1

89 potential nitrilases were screened for activity of conversion terephthalonitril to 4-cyanobenzoic acid. Donor organism and SEQ ID of the amino acid sequence of 18 nitrilases active in screening and one non-functional nitrilase are listed in Table 1. The coding region of the nitrilases were optimized for expression in *E. coli*, these sequences synthesized and cloned in the expression vector pDHE (Stueckler et al. (2010) Tetrahedron 66(3-2)).

*E. coli* strains were transformed with the expression vectors, expression of the nitrilases induced and the culture harvested and tested for activity as described below.

TABLE 1

Donor Organism, SEQ ID, and 4-cyanobenzoic acid formation of 18 active nitrilases.

| Seq. ID | Donor Organism | 4-cyanobenzoic acid [mM] |
|---|---|---|
| 10 | *Tepidicaulis marinus* | 88 |
| 101 | *Smithella* sp. SDB | 2 |
| 4 | Unknown prokaryotic organism | 328 |
| 103 | *Bradyrhizobium diazoefficiens* | 35 |
| 105 | *Aquimarina atlantica* | 2 |
| 107 | *Arthrobacter* sp. Soil736 | 7 |
| 12 | *Sphingomonas wittichii* RW1 | 126 |
| 111 | *Pseudomonas* sp. RIT357 | 87 |
| 113 | *Nocardia brasiliensis* NBRC 14402 | 22 |
| 109 | *Pseudomonas mandelii* JR-1 | 14 |
| 8 | *Candidatus* Dadabacteria bacterium CSP1-2 | 268 |
| 22 | *Salinisphaera shabanensis* E1L3A | 81 |
| 16 | *Synechococcus* sp. CC9605 | 158 |
| 14 | *Rhizobium* sp. YK2 | 192 |
| 6 | *Agrobacterium rubi* | 293 |
| 20 | *Flavihumibacter solisilvae* | 106 |
| 115 | *Defluviimonas alba* | 60 |
| 2 | *Comamonas testosteroni* | 704 |
| 24 | *Erythrobacter* sp. JL475 | 0 |

128 mg of terephthalonitrile were weighed to a 1.5 mL Eppendorf tube and mixed with 50 mM phosphate buffer solution at pH 7. To start the reaction, 50-100 μL of *E. coli* cell suspension containing different nitrilases were added and the mixture shaken at 37° C. The final terephthalonitrile concentration in the reaction tube was 1 M. After 48 hours, the entire reaction mixture was diluted in DMSO. A sample of this solution was withdrawn, diluted in water and subjected to HPLC analysis. The results are reported as concentration of 4-cyanobenzoic acid present in the 1 mL reaction mixture prior to dilution with DMSO.

Example 2

1100 mL water and 100 g of terephthalonitrile were placed in a reactor.

The biocatalyst was used in the form of a concentrate cell suspension containing the nitrilase from *Comamonas testosteroni* (Seq. ID 2) and it was added to the reactor, whereby the bioconversion started. The temperature was kept at 37° C. and the reactor was mixed by an overhead-stirrer. The mixture was stirred for 21 h and samples for the analysis of 4-cyanobenzoic acid were taken from the reactor. The time course of terephthalonitrile conversion and 4-cyanobenzoic acid formation is given in FIG. 2.

After the bioconversion, the reaction mixture was removed from the reactor and filtered through Celite535 to remove the heterologous *E. coli* cells expressing the nitrilase. Acid, in this case sulfuric acid, was added to precipitate 4-cyanobenzoic acid, which was separated from the aqueous reaction mixture by filtration. The wet product was dried until a constant weight was reached. 111.5 g 4-cyanobenzoic acid were recovered.

Example 3

128 mg of terephthalonitrile were weighed to a 1.5 mL Eppendorf tube and mixed with water or 50 mM phosphate buffer solution at pH 7. To start the reaction, 50-100 μL of *E. coli* cell suspension containing different nitrilases were added and the mixture shaken at 37° C. The final terephthalonitrile concentration in the reaction tube was 1 M. After 24 hours, the entire reaction mixture was diluted in DMSO. A sample of this solution was withdrawn, diluted in water and subjected to HPLC analysis. The results are reported as concentration of 4-cyanobenzoic acid present in the 1 mL reaction mixture prior to dilution with DMSO.

TABLE 2

4-cyanobenzoic acid formation from the nitrilases with the sequence IDs 4 (Unknown prokaryotic organism), 8 (*Candidatus* Dadabacteria bacterium CSP1-2), 6 (*Agrobacterium rubi*), and 2 (*Comamonas testosteroni*) and from the six nitrilases described in CN107641622A Ara Nit (*Arabidopsis thaliana*), Bras Nit (*Brassica oleracea*), Can Nit (*Camelia sativa*), Panto Nit (*Pantoea* sp. AS-PWVM4), Acid Nit (*Acidovorax facilis* 72W), Lepto Nit (*Leptolyngbya* sp.). Either water or an aqueous buffered solution (50 mM potassium phosphate buffer, pH 7) was used as reaction medium. 4-cyanobenzoic acid formation is given in mM as analysed after the incubation phase and also as mM/OD600 for normalization of the produced amount to the applied heterologous E. coli biomass in each reaction.

| | 4-cyanobenzoic acid [mM] | | 4-cyanobenzoic acid [mM/OD600] | |
|---|---|---|---|---|
| Seq. ID | Water | Buffer | Water | Buffer |
| 4 | 297 | 341 | 44 | 50 |
| 8 | 284 | 294 | 24 | 24 |
| 6 | 275 | 345 | 26 | 32 |
| 2 | 752 | 655 | 136 | 118 |
| Ara Nit | 46 | 56 | 5 | 6 |
| Bras Nit | 79 | 82 | 7 | 7 |
| Can Nit | 50 | 38 | 5 | 4 |
| Panto Nit | 198 | 229 | 22 | 26 |
| Acid Nit | 105 | 136 | 13 | 17 |
| Lepto Nit | 178 | 222 | 15 | 19 |

Example 4

The effect of the addition of $Mg^{2+}$ ions to the reaction mixture was investigated. 128 mg of terephthalonitrile were weighed to a 1.5 mL Eppendorf tube and mixed with water. $MgSO_4$ was added from a 1 M stock solution in water yielding different final concentrations of $MgSO_4$ in the reaction. To start the reaction, 100 μL of an *E. coli* cell suspension containing the nitrilase from *Comamonas testosteroni* (Seq ID No. 2) were added and the mixture was shaken at 1000 rpm in an Eppendorf Thermomixer at 37° C. The final terephthalonitrile concentration in the reaction tube was 1 M. After 23 hours, the entire reaction mixture was diluted in DMSO. A sample of this solution was withdrawn, diluted in water and subjected to HPLC analysis. The results are reported as concentration of 4-cyanobenzoic acid present in the 1 mL reaction mixture prior to dilution with DMSO.

TABLE 3

4-cyanobenzoic acid formation from the nitrilase with the sequence ID 2 (*Comamonas testosteroni*) when different $MgSO_4$ concentrations are used in the biocatalytic reaction.

| $MgSO_4$ [mM] | 4-cyanobenzoic acid [mM] | Residual Terephthalonitrile [mM] | Sum [mM] |
|---|---|---|---|
| 0 | 855 | 186 | 1041 |
| 10 | 931 | 162 | 1093 |
| 25 | 958 | 51 | 1009 |
| 40 | 1038 | 66 | 1104 |
| 50 | 955 | 19 | 973 |
| 100 | 1075 | 0 | 1075 |
| 125 | 1003 | 0 | 1003 |
| 150 | 1026 | 0 | 1026 |
| 175 | 1012 | 0 | 1012 |
| 200 | 1016 | 0 | 1016 |
| 250 | 1042 | 7 | 1049 |

The highest 4-cyanobenzoic acid concentration was achieved when 100 or more mM MgSO4 is added to the reaction. In these cases, complete conversion of the terephthalonitrile was observed.

Example 5

The effect of the addition of $Mg^{2+}$ ions to the reaction mixture was investigated in combination with higher terephthalonitrile concentrations. 128 mg or 256 mg of terephthalonitrile were weighed to a 1.5 mL Eppendorf tube and mixed with water. $MgSO_4$ was added from a 1 M stock solution in water yielding 100 or 200 mM $MgSO_4$, respectively, in the reaction mixture. To start the reaction, 100 μL of an *E. coli* cell suspension containing the nitrilase from *Comamonas testosteroni* (Seq ID No. 2) were added and the mixture was shaken at 1000 rpm in an Eppendorf Thermomixer at 37° C. The final terephthalonitrile concentration in the reaction tube was 1 M or 2 M, respectively. After previously defined time points, the entire reaction mixture was diluted in DMSO. Samples of this solutions were withdrawn, diluted in water and subjected to HPLC analysis. The results are reported as concentration of 4-cyanobenzoic acid present in the 1 mL reaction mixture prior to dilution with DMSO.

TABLE 4

4-cyanobenzoic acid formation from the nitrilase with the sequence ID 2 (*Comamonas testosteroni*) when different $MgSO_4$ concentrations and different terephthalonitrile concentrations are used in the biocatalytic reaction.

| Terephthalonitrile [mM] | $MgSO_4$ [mM] | Reaction Time [h] | 4-cyanobenzoic acid [mM] | Residual Terephthalonitrile [mM] |
|---|---|---|---|---|
| 1000 | 100 | 0.5 | 392 | 643 |
| | | 1 | 651 | 450 |
| | | 2 | 1028 | 99 |
| | | 4 | 1104 | 6 |
| | | 6 | 1054 | 11 |
| | | 23 | 1072 | 0 |
| 2000 | 100 | 0.5 | 381 | 1075 |
| | | 1 | 649 | 927 |
| | | 2 | 932 | 854 |
| | | 4 | 1015 | 867 |
| | | 6 | 1038 | 894 |
| | | 23 | 1083 | 860 |
| 1000 | 200 | 0.5 | 370 | 711 |
| | | 1 | 616 | 445 |
| | | 2 | 973 | 70 |
| | | 4 | 1059 | 3 |
| | | 6 | 1078 | 5 |
| | | 23 | 1080 | 0 |
| 2000 | 200 | 0.5 | 355 | 1072 |
| | | 1 | 569 | 902 |
| | | 2 | 1033 | 877 |
| | | 4 | 1307 | 783 |
| | | 6 | 1314 | 795 |
| | | 23 | 1355 | 805 |

The highest product concentration was achieved when the reaction mixture is supplemented with 200 mM $MgSO_4$ and 2 M terephthalonitrile. Complete conversion of 2 M terephthalonitrile, however, was not achieved.

Example 6

The effect of the temperature on the reaction performance was investigated in the presence of absence of MgSO4. Approximately 128 mg of terephthalonitrile were weighed to a 1.5 mL Eppendorf tube and mixed with water. $MgSO_4$ was added from a 1 M stock solution in water yielding 0 or 100 mM $MgSO_4$, respectively, in the reaction mixture. To start the reaction, 100 μL of an *E. coli* cell suspension containing the nitrilase from *Comamonas testosteroni* (Seq ID No. 2) were added and the mixture was shaken at 1000 rpm in an Eppendorf Thermomixer at different temperatures (i.e., 20° C., 25° C., 30° C., 37° C.). The final terephthalonitrile concentration in the reaction tube was approximately 1 M. After previously defined time points, the entire reaction mixture was diluted in DMSO. Samples of this solutions were withdrawn, diluted in water and subjected to HPLC analysis. The results are reported as concentration of 4-cyanobenzoic acid present in the 1 mL reaction mixture prior to dilution with DMSO.

TABLE 5

4-cyanobenzoic acid formation from the nitrilase with the sequence ID 2 (*Comamonas testosteroni*) at different temperatures in the presence or absence of $MgSO_4$ in the biocatalytic reaction.

| Temperature [° C.] | $MgSO_4$ [mM] | Reaction Time [h] | 4-cyanobenzoic acid [mM] | Residual Terephthalonitrile [mM] |
|---|---|---|---|---|
| 20 | 0 | 0.5 | 118 | 634 |
| | | 1 | 256 | 622 |
| | | 2 | 549 | 520 |
| | | 22 | 1079 | 0 |
| 20 | 100 | 0.5 | 76 | 680 |
| | | 1 | 176 | 752 |
| | | 2 | 407 | 650 |
| | | 22 | 1034 | 0 |
| 25 | 0 | 0.5 | 217 | 714 |
| | | 1 | 438 | 561 |
| | | 2 | 761 | 326 |
| | | 22 | 1072 | 0 |
| 25 | 100 | 0.5 | 182 | 675 |
| | | 1 | 364 | 656 |
| | | 2 | 706 | 350 |
| | | 22 | 1043 | 0 |
| 30 | 0 | 0.5 | 321 | 701 |
| | | 1 | 531 | 520 |

TABLE 5-continued 4-cyanobenzoic acid formation from the nitrilase with the sequence ID 2 (*Comamonas testosteroni*) at different temperatures in the presence or absence of $MgSO_4$ in the biocatalytic reaction.

| Temperature [° C.] | $MgSO_4$ [mM] | Reaction Time [h] | 4-cyanobenzoic acid [mM] | Residual Terephthalonitrile [mM] |
|---|---|---|---|---|
| | | 2 | 812 | 216 |
| | | 22 | 1045 | 0 |
| 30 | 100 | 0.5 | 246 | 744 |
| | | 1 | 497 | 568 |
| | | 2 | 897 | 181 |
| | | 22 | 1090 | 0 |
| 37 | 0 | 0.5 | 611 | 442 |
| | | 2 | 853 | 245 |
| | | 23 | 855 | 186 |
| 37 | 100 | 0.5 | 480 | 648 |
| | | 1 | 1049 | 58 |
| | | 2 | 1075 | 0 |

At a reaction temperature of 37° C., full conversion of 1 M terephthalonitrile was only achieved when the reaction mixture was supplemented with $MgSO_4$. This implies that the beneficial effect of $Mg^{2+}$ addition is more pronounced at higher reaction temperatures.

Example 7

The applied biocatalyst (*E. coli* cell suspension containing the nitrilase from *Comamonas testosterone* (Seq ID No. 2) principally catalyzes the conversion of terephthalonitrile to 4-cyanobenzoic acid as the main reaction.

The reaction conditions during the biocatalytic conversion can be adjusted in order to minimize excessive terephthalic acid formation. 8.14 g terephthalonitrile were added to 91.36 g deionized water in a 100 mL working volume EasyMax 102 reactor (Eppendorf, Germany). The temperature was adjusted to 33° C. and the stirrer speed was set to 400 rpm. Mixing was mediated by an impeller stirrer. 0.5 g of an *E. coli* cell suspension in potassium phosphate buffer containing the nitrilase from *Comamonas testosteroni* (Seq ID No. 2) were added to start the bioconversion. Samples were withdrawn for analysis of 4-cyanobenzoic acid and terephthalic acid at regular intervals. After 10.5 h the reaction was terminated, and cells were removed by filtration over Celite535. The final 4-cyanobenzoic acid content was 93 g/kg and the final terephthalic acid content was 0.2 g/kg. This corresponds to full conversion of the applied terephthalonitrile to these two products of the biocatalytic reaction. The fraction of 4-cyanobenzoic acid relative to the total product amount was 99.8%. 0.2% of the total product fraction was terephthalic acid. The terephthalic acid fraction is dependent on the mixing efficiency, the amount of biocatalyst added to the reaction and the temperature.

TABLE 6

Reaction conditions and reaction parameter for the bioconversion of terephthalonitrile.

| Parameter | Unit | Data |
|---|---|---|
| Reaction temperature | [° C.] | 33 |
| Reaction scale | [kg] | 0.1 |
| TDN | [g] | 8.136 |
| Biomass concentration | [gBDW/kg] | 0.183 |
| Initial specific initial activity | [kU/gBDW] | 5.2 |
| Full conversion | YES/NO | YES |
| Total reaction duration | [h] | 10.5 |
| Final 4-CBA concentration | [g/kg] | 93.02 |
| Final TA concentration | [g/kg] | 0.20 |
| Mass fraction 4-CBA of total product | [%] | 99.79 |
| Specific yield Yp/x | [g4-CBA/gBDW] | 508 |
| Conversion | [%] | 100 |

TDN: terephthalonitrile, BDW: biomass dry weight, 4-CBA: 4-cyanobenzoic acid, TA: terephthalic acid. The initial specific activity of the catalyst is determined in the first hour of reaction and is given in kU. 1 kU corresponds to 1 mmol of 4-cyanobenzoic acid formed per minute.

Example 8

3515 g water and 445 g terephthalonitrile were placed in a reactor. The biocatalyst was used in the form of a concentrated cell suspension containing the nitrilase from *Comamonas testosteroni* (Seq. ID 2) and added to the reactor, whereby the bioconversion started. The temperature was kept at 30° C. and the reactor was mixed by an overhead-stirrer. The mixture was stirred for 23 h. After the bioconversion, the pH was adjusted with NaOH to pH 9.4 and the reaction mixture was removed from the reactor. An ultrafiltration on a Sartoflow Advance (Sartorius) machine was performed using a membrane with a molecular weight cut-off of 10 kDa to remove the heterologous *E. coli* cells expressing the nitrilase. The resulting filtrate was split into two portions. 1748 g of the resulting filtrate were diluted with 1500 g water and the pH was adjusted to pH 2.2 by titration with 32 wt-% hydrochloric acid to precipitate the 4-cyanobenzic acid. Another 500 g of water were added to facilitate mixing during the addition of the hydrochloric acid solution. The suspension was filtered and washed with 1×1500 g water. The wet product was dried until a constant weight was reached. 193 g crystalline product were recovered and analyzed by HPLC and for chloride as well as water content (portion 1). 2029 g of the resulting filtrate were diluted with 1500 g water and the pH was adjusted to pH 1.89 by titration with 32 wt-% hydrochloric acid to precipitate the 4-cyanobenzic acid. Another 250 g of water were added to facilitate mixing during the addition of the hydrochloric acid solution. The suspension was filtered and washed with 2×1500 g water. The wet product was dried until a constant weight was reached. 223 g crystalline product were recovered and analyzed by HPLC and for chloride as well as water content (portion 2) The amount of water used for washing of the filter cake is decisive for the resulting product purity. Larger washing volume reduce the amount of residual chloride and other unwanted components in the final product. The fraction missing to give a sum of 100% is composed of ammonium and sodium and contaminants from the preceding biotransformation such as phosphate.

TABLE 7

Chemical composition of the product when hydrochloric acid is used for the precipitation of 4-cyanobenzoic acid.

| Compound | Content in portion 1 | Content in portion 2 |
|---|---|---|
| 4-cyanobenzoic acid | 97.3 [wt-%] | 99.0 [wt-%] |
| Terephthalic acid | 0.3 [wt-%] | 0.3 [wt-%] |
| Chloride (IC) | 1.0 [wt-%] | 0.3 [wt-%] |
| Water | 0.1 [wt-%] | 0.1 [wt-%] |

IC: ion chromatography

Example 9

881 g water and 108.9 g terephthalonitrile were placed in a reactor. The biocatalyst was used in the form of a concentrate cell suspension containing the nitrilase from *Comamonas testosteroni* (Seq. ID 2) and added to the reactor, whereby the bioconversion started. The temperature was kept at 30° C. and the reactor was mixed by an overhead-stirrer. The mixture was stirred for 24 h.

612 g of the filtrate was diluted with 1000 g water and the pH was adjusted to pH 2.1 by titration with 98 wt-% sulfuric acid to precipitate the 4-cyanobenzic acid. The suspension was filtered and washed with 250 g water. The wet product was dried until a constant weight was reached. 56 g crystalline product were recovered and analyzed by HPLC for 4-cyanobenzoic acid and for ammonium, sulfate, and sodium content.

TABLE 8

Chemical composition of the product when sulfuric acid is used for the precipitation of 4-cyanobenzoic acid.

| Compound | Content |
|---|---|
| 4-cyanobenzoci acid (HPLC) | 96.00 [wt-%] |
| Terephthalic acid | Not determined |
| Ammonium (IC) | 0.60 [wt-%] |
| Sulfate (IC) | 3.10 [wt-%] |
| Na (Elementary analysis) | 0.70 [wt-%] |
| Water | Not determined |

IC: ion chromatography.

What is claimed is:

1. A process for producing 4-cyano benzoic acid or salt thereof comprising the steps of i) Providing an aqueous medium comprising water, one or more nitrilase and terephthalonitrile, ii) Incubating the aqueous medium and iii) Optionally isolating the 4-cyano benzoic acid or salt thereof from the aqueous medium after incubation, wherein the one or more nitrilase is capable of catalysing the reaction from terephthalonitrile to ammonium 4-cyano benzoic acid in an aqueous medium comprising water, nitrilase and terephthalonitrile and optionally ammonium 4-cyano benzoic acid, wherein the concentration of ammonium 4-cyano benzoic acid in the aqueous medium after incubation is at least 5% (w/w) and the concentration of terephthalonitrile is below 1.0% (w/w);

wherein the nitrilase comprises a sequence selected from the group consisting of a) a polypeptide having 100% identity to the amino acid sequence of SEQ ID NO: 2, 4, 6 or 8, b) a polypeptide having at least 90% identity to the amino acid sequence of SEQ ID NO: 2, 4, 6 or 8, c) a polypeptide encoded by a nucleic acid sequence having 100% identity to the nucleic acid sequence of SEQ ID NO: 1, 3, 5 or 7, and d) a polypeptide encoded by a nucleic acid sequence having at least 90% identity to the nucleic acid sequence of SEQ ID NO: 1, 3, 5 or 7, wherein the polypeptide as defined in b), c), and d) catalyzes the reaction from terephthalonitrile to ammonium 4-cyano benzoic acid in an aqueous medium.

2. The process of claim 1 wherein after incubation the aqueous medium comprises below 0.5% (w/w) terephthalic acid.

3. A process for producing 4-cyano benzoic acid or salt thereof comprising the steps of i) Providing an aqueous medium comprising water, one or more nitrilase and terephthalonitrile, ii) Incubating the aqueous medium and iii) Optionally isolating the 4-cyano benzoic acid or salt thereof from the aqueous medium after incubation, wherein the one or more nitrilase is selected from the group consisting of a) a polypeptide having 100% identity to the amino acid sequence of SEQ ID NO: 2, 4, 6, 8, 10, 12, 14, 16, 20 or 22, b) a polypeptide having at least 90% identity to the amino acid sequence of SEQ ID NO: 2, 4, 6, 8, 10, 12, 14, 16, 20 or 22, c) a polypeptide encoded by a nucleic acid sequence having 100% identity to the nucleic acid sequence of SEQ ID NO 1, 3, 5, 7, 9, 11, 13, 15, 19 or 21, and d) a polypeptide encoded by a nucleic acid sequence having at least 90% identity to the nucleic acid sequence of SEQ ID NO: 1, 3, 5, 7, 9, 11, 13, 15, 19 or 21, wherein the polypeptide as defined in b), c), and d) has an activity of converting terephthalonitrile to ammonium 4-cyano benzoic acid in an aqueous medium.

4. The process of claim 3 wherein the aqueous medium further comprises a divalent cation.

5. The process of claim 4 wherein the divalent cation is $Mg^{2+}$, $Mn^{2+}$, $Ca^{2+}$, $Fe^{2+}$, $Zn^{2+}$ or $Co^{2+}$.

6. The process of claim 3 wherein the terephthalonitrile is added to the aqueous medium before incubation in a concentration of between 1% and 30% w/w.

7. The process of claim 3 wherein a pH-value of the aqueous medium is adjusted to below 5 by adding acid to the aqueous medium during or after incubation.

8. The process of claim 3 wherein the 4-cyano benzoic acid or salt thereof is isolated by filtration or centrifugation after incubation.

9. The process of claim 3 wherein the aqueous medium is incubated for at least 2h.

10. The process of claim 3 wherein the aqueous medium is incubated between 15 and 50° C.

11. The process of claim 3 wherein the nitrilase is produced by fermentation.

12. A method for making an aqueous solution containing at least 5% (w/w) ammonium 4-cyano benzoic acid, below 1.0% (w/w) terephthalonitrile, and below 0.5% (w/w) terephthalic acid, comprising the steps of I) Providing an aqueous medium comprising water, one or more nitrilase and terephthalonitrile and II) Incubating the aqueous medium, wherein the nitrilase is capable of catalysing a reaction from terephthalonitrile to 4-cyano benzoic acid in an aqueous medium, wherein the aqueous medium further comprises a divalent cation;

wherein the nitrilase comprises a sequence selected from the group consisting of a) a polypeptide having 100% identity to the amino acid sequence of SEQ ID NO: 2, 4, 6 or 8, b) a polypeptide having at least 90% identity to the amino acid sequence of SEQ ID NO: 2, 4, 6 or 8, c) a polypeptide encoded by a nucleic acid sequence having 100% identity to the nucleic acid sequence of SEQ ID NO: 1, 3, 5 or 7, and d) a polypeptide encoded by a nucleic acid sequence having at least 90% identity to the nucleic acid sequence of SEQ ID NO: 1, 3, 5 or 7, wherein the polypeptide as defined in b), c), and d) catalyzes the reaction from terephthalonitrile to ammonium 4-cyano benzoic acid in an aqueous medium.

13. The method of claim 12 wherein the divalent cation is $Mg^{2+}$, $Mn^{2+}$, $Ca^{2+}$, $Fe^{2+}$, $Zn^{2+}$ or $Co^{2+}$.

14. The method of claim 12 wherein the terephthalonitrile is added to the aqueous medium before incubation in a concentration of between 1% and 30% w/w.

15. The method of claim 12 wherein a pH-value of the aqueous medium is adjusted to below 5 by adding acid to the aqueous medium during or after incubation.

16. The method of claim 12 wherein the method further comprises isolating the 4-cyano benzoic acid by filtration or centrifugation after incubation.

17. The method of claim 12 wherein the aqueous medium is incubated for at least 2h.

18. The method of claim 12 wherein the aqueous medium is incubated between 15 and 50° C.

19. The method of claim 12 wherein the nitrilase is produced by fermentation.

20. The process of claim 1 wherein the nitrilase comprises a sequence selected from the group consisting of a) a polypeptide having 100% identity to the amino acid sequence of SEQ ID NO: 2, 4, 6 or 8, and b) a polypeptide encoded by a nucleic acid sequence having 100% identity to the nucleic acid sequence of SEQ ID NO: 1, 3, 5 or 7.

21. The process of claim 1 wherein the nitrilase comprises a sequence selected from the group consisting of a) a polypeptide having 100% identity to the amino acid sequence of SEQ ID NO: 2, 4, 6 or 8, b) a polypeptide having at least 95% identity to the amino acid sequence of SEQ ID NO: 2, 4, 6 or 8, c) a polypeptide encoded by a nucleic acid sequence having 100% identity to the nucleic acid sequence of SEQ ID NO: 1, 3, 5 or 7, and d) a polypeptide encoded by a nucleic acid sequence having at least 95% identity to the nucleic acid sequence of SEQ ID NO: 1, 3, 5 or 7.

22. The process of claim 3 wherein the one or more nitrilase is selected from the group consisting of a) a polypeptide having 100% identity to the amino acid sequence of SEQ ID NO: 2, 4, 6, 8, 10, 12, 14, 16, 20 or 22, and b) a polypeptide encoded by a nucleic acid sequence having 100% identity to the nucleic acid sequence of SEQ ID NO 1, 3, 5, 7, 9, 11, 13, 15, 19 or 21.

23. The process of claim 3 wherein the one or more nitrilase is selected from the group consisting of a) a polypeptide having 100% identity to the amino acid sequence of SEQ ID NO: 2, 4, 6, 8, 10, 12, 14, 16, 20 or 22, b) a polypeptide having at least 95% identity to the amino acid sequence of SEQ ID NO: 2, 4, 6, 8, 10, 12, 14, 16, 20 or 22, c) a polypeptide encoded by a nucleic acid sequence having 100% identity to the nucleic acid sequence of SEQ ID NO 1, 3, 5, 7, 9, 11, 13, 15, 19 or 21, and d) a polypeptide encoded by a nucleic acid sequence having at least 95% identity to the nucleic acid sequence of SEQ ID NO: 1, 3, 5, 7, 9, 11, 13, 15, 19 or 21.

24. The process of claim 12 wherein the nitrilase comprises a sequence selected from the group consisting of a) a polypeptide having 100% identity to the amino acid sequence of SEQ ID NO: 2, 4, 6 or 8, and b) a polypeptide encoded by a nucleic acid sequence having 100% identity to the nucleic acid sequence of SEQ ID NO: 1, 3, 5 or 7.

25. The process of claim 12 wherein the nitrilase comprises a sequence selected from the group consisting of a) a polypeptide having 100% identity to the amino acid sequence of SEQ ID NO: 2, 4, 6 or 8, b) a polypeptide having at least 95% identity to the amino acid sequence of SEQ ID NO: 2, 4, 6 or 8, c) a polypeptide encoded by a nucleic acid sequence having 100% identity to the nucleic acid sequence of SEQ ID NO: 1, 3, 5 or 7, and d) a polypeptide encoded by a nucleic acid sequence having at least 95% identity to the nucleic acid sequence of SEQ ID NO: 1, 3, 5 or 7.

* * * * *